United States Patent
Ramkumar

(10) Patent No.: US 11,554,148 B2
(45) Date of Patent: Jan. 17, 2023

(54) AAV-MEDIATED BMI1 GENE TRANSFER FOR TREATING MACULAR DEGENERATION

(71) Applicant: OCULOGENEX INC., La Habra, CA (US)

(72) Inventor: Hema Lakshmi Ramkumar, Seal Beach, CA (US)

(73) Assignee: OCULOGENEX INC., La Habra, CA (US)

( * ) Notice: Subject to any disclaimer, the term of this patent is extended or adjusted under 35 U.S.C. 154(b) by 0 days.

(21) Appl. No.: 17/379,997

(22) Filed: Jul. 19, 2021

(65) Prior Publication Data

US 2022/0047655 A1 Feb. 17, 2022

Related U.S. Application Data

(63) Continuation-in-part of application No. PCT/US2021/037137, filed on Jun. 12, 2021.

(60) Provisional application No. 63/087,781, filed on Oct. 5, 2020, provisional application No. 63/038,810, filed on Jun. 13, 2020.

(51) Int. Cl.
| | |
|---|---|
| *A61K 35/761* | (2015.01) |
| *A61K 48/00* | (2006.01) |
| *C12N 15/86* | (2006.01) |
| *A61K 9/00* | (2006.01) |

(52) U.S. Cl.
CPC .......... *A61K 35/761* (2013.01); *A61K 9/0019* (2013.01); *A61K 48/00* (2013.01); *C12N 15/86* (2013.01)

(58) Field of Classification Search
None
See application file for complete search history.

(56) References Cited

U.S. PATENT DOCUMENTS

2011/0123509 A1* 5/2011 Jantz .................. C12N 9/22
530/409

OTHER PUBLICATIONS

Bruewer (PLOS One, 8(4): e60218, p. 1-7, 2013). (Year: 2013).*

* cited by examiner

*Primary Examiner* — Anoop K Singh
*Assistant Examiner* — Magdalene K Sgagias
(74) *Attorney, Agent, or Firm* — Entralta P.C.; James F. Fleming; Peter D. Weinstein

(57) ABSTRACT

The present invention relates generally to gene therapy for treating ailments that can affect vision such as retinal degeneration, retinal dystrophy, macular degeneration, macular dystrophy, ischemic retinopathies, and glaucoma. Embodiments include systems and treatments that use AAV-mediated gene therapy or non AAV-mediated DNA, mRNA, or protein therapy to target all retinal cells. An AAV virion can be introduced (e.g., via intravitreal or subretinal injection) into an eye of an individual, or systemically, to express a heterologous gene product such as BMI1 protein (B lymphoma Mo-MLV insertion region 1 homolog).

6 Claims, 14 Drawing Sheets

Specification includes a Sequence Listing.

AAV-MEDIATED BMI1 GENE TRANSFER FOR TREATING MACULAR DEGENERATION

CROSS REFERENCE TO RELATED APPLICATIONS

The present application is a Continuation in Part of PCT/US21/37137 which claims priority to U.S. provisional patent application No. 63/087,781 filed on Oct. 5, 2020 and U.S. provisional patent application No. 63/038,810 filed on Jun. 13, 2020. Each of these applications is incorporated by reference herein in their entirety.

REFERENCE TO SEQUENCE LISTING

The entire content of the following electronic submission of the sequence listing via the USPTO EFS-WEB server, as authorized and set forth in MPEP § 1730 II.B.2(a)(C), is incorporated herein by reference in its entirety for all purposes. The sequence listing is identified on the electronically filed text file as follows: File Name: NM2-001US_ST25; Date of Creation: Sep. 15, 2021; Size (bytes): 7.29 KB

TECHNICAL FIELD

The present disclosure relates generally to ophthalmic treatments, and more specifically to gene therapy systems and methods for treating retinal and macular degeneration and dystrophy and optic nerve diseases.

BACKGROUND

In a normal eye, photoreceptors form the outermost layer of the retina. They convert light into electrical signals, which are sent to neurons in the retina's middle layer known as bipolar cells. Bipolar cells send visual information to the inner layer, made up of ganglion cells, which then connect to the brain via the optic nerve.

Retinopathy is any damage to the retina of the eyes which may cause vision impairment. Retinopathy often refers to retinal vascular disease, or damage to the retina caused by abnormal blood flow. Retinopathy is often secondary to diseases such as diabetes or hypertension. Other conditions that affect the retina and can impact vision include retinal degeneration, retinal dystrophy, macular degeneration and macular dystrophy.

Retinal Degeneration

Retinal degeneration is a retinopathy that includes deterioration of the retina caused by the progressive death of its cells. There are several reasons for retinal degeneration, including artery or vein occlusion, diabetic retinopathy, R.L.F./R.O.P. (retrolental fibroplasia/retinopathy of prematurity), or disease (usually hereditary). Retinal degeneration can lead to impaired vision, night blindness, retinal detachment, light sensitivity, tunnel vision, and loss of central or peripheral vision to total loss of vision.

Advanced retinal degeneration can lead to photoreceptor cell death. Without proper function of the photoreceptor cells, vision is not possible. Irreversible loss of these cells has been attributed as a cause of blindness in many retinal degenerative disorders, including retinitis pigmentosa (RP).

Retinal Dystrophy

Retinal dystrophies are chronic and progressive disorders of visual function. "Dystrophy" refers to a condition that a person is born with, "Retinal" refers to the retina. The retinal dystrophies are a clinically and genetically heterogeneous group of eye disorders that are characterized by degeneration of different cell types within the retina. Retinal cell types involved in retinal dystrophies include the rods and cones. In general, retinal dystrophies are classified according to the types of cells within the retina that are primarily affected, the age of onset of first symptoms, the progression of visual impairment over time and the presence or absence of other medical features. Specific subtypes of retinal dystrophy include rod-cone dystrophies such as retinitis pigmentosa (RT), cone-rod or cone dystrophies such as achromatopsia, and macular dystrophies such as Stargardt disease.

Macular Degeneration

Macular degeneration is typically classified as dry or wet. Age-related macular degeneration (AMD) is the leading cause of vision loss in people over the age of 50 years old. It occurs when a part of the retina called the macula is damaged and can lead to the loss of central vision.

The wet form of macular degeneration is less common but more serious. Wet AMD occurs when new, abnormal blood vessels grow under the retina. These vessels may leak blood or other fluids, causing scarring of the macula. Vision loss occurs faster with wet AMD and patients may not realize they have AMD until their vision is very blurry. If detected early, wet AMD can be treated with intraocular injections of anti-VEGF medications.

Macular Dystrophy

Macular dystrophy is a relatively rare eye condition. It is linked to inherited genetic mutations rather than age. Macular dystrophy causes deterioration of the most sensitive part of the central retina (macula), which has the highest concentration of light-sensitive cells (photoreceptors). It is caused by a pigment that builds up in the macula's cells. Over time, this substance can damage cells that play a key role in clear central vision.

Conventional treatment options for patients affected by degenerative ocular conditions are limited. There are no treatments that are currently available to treat retinal degeneration and dystrophy. Intravitreal anti-angiogenic therapies can temporarily inactivate actively growing abnormal blood vessels from AMD. Similarly, there is no cure or known treatment to stop the progression of macular degeneration or dystrophies. Management usually includes regular eye exams to monitor progression of the disease and for complications such as choroidal neovascularization (CNV). Patients can lose all their central vision from advanced dry AMD when geographic atrophy develops. There is no treatment or cure for this condition. Wet AMD can be treated with regular injections into the eyes. Patients can partially recover vision as the blood vessels shrink and the fluid under the retina absorbs, allowing retinal cells to regain some function. Because of the limited options to treat retinopathies, a need exists for an improved treatments and therapies.

Gene transfer has become recognized as a promising tool for treatment of diseases at both the cellular and molecular levels. Recently, the application of gene therapy for the treatment of human diseases, either inherited (e.g., adenosine deaminase (ADA) deficiency) or acquired (e.g., cancer or infectious disease), has received considerable attention. With the advent of improved gene transfer techniques and the identification of an expanding library of defective gene-related diseases, gene therapy has rapidly evolved from a treatment theory to a practical reality.

Viral vectors are tools commonly used by molecular biologists to deliver genetic material into cells. This process can be performed inside a living organism (in vivo) or in cell culture (in vitro). Viruses have evolved specialized molecular mechanisms to efficiently transport their genomes inside the cells they infect. Delivery of genes, or other genetic material, by a vector is termed transduction and the infected cells are described as transduced.

The present invention discloses systems and treatments that use AAV-mediated gene therapy to target retinal pigment epithelium (RPE) cells and photoreceptor cells. For instance, AAV1, AAV2, AAV4, AAV5 and AAV8 serotypes are known to have specificity for RPE cells, while AAV2, AAV5 and AAV8 have specificity for photoreceptor cells in the eye. An AAV virion can be introduced (e.g., via intravitreal, subretinal, sub-internal limiting membrane, or suprachoroidal injection) into an eye of an individual to express a heterologous gene product such as BMI1 protein (B lymphoma Mo-MLV insertion region 1 homolog). Also provided are methods of treating pharmaceutical compositions thereof, and articles of manufacture.

SUMMARY

The following summary is provided to facilitate an understanding of some of the innovative features unique to the disclosed embodiment and is not intended to be a full description. A full appreciation of the various aspects of the embodiments disclosed herein can be gained by taking into consideration the entire specification, claims, drawings, and abstract as a whole.

The invention includes compositions and methods for treating an eye ailment (e.g. retinal degeneration, retinal dystrophy, macular degeneration, macular dystrophy, glaucoma) in the eye of a subject using an adeno-associated virus (AAV) viral particle.

In one aspect, a pharmaceutical composition for preventing, arresting progression of or ameliorating a retinopathy comprising a viral vector and a pharmaceutically acceptable carrier. The viral vector particle can be AAV type 8 and comprise a nucleic acid sequence encoding BMI1 protein. Other AAVs can include an AAV type 2.

In another aspect, a method of targeting retinal pigment epithelium (RPE) cells for gene correction therapy in a subject in need thereof is provided. The method includes administering to the subject an effective concentration of a composition comprising any of the recombinant adeno-associated virus (AAV) described herein and a pharmaceutically acceptable carrier.

In yet another aspect, a method of preventing, arresting progression of, or ameliorating vision loss associated with retinal degeneration in a subject is provided. The method includes administering to the subject an effective concentration of a composition comprising any recombinant adeno-associated virus (AAV) described herein and a pharmaceutically acceptable carrier.

In yet another aspect, a method of preventing, arresting progression of, or ameliorating vision loss associated with retinal dystrophy in a subject is provided. The method includes administering to the subject an effective concentration of a composition comprising any recombinant adeno-associated virus (AAV) described herein and a pharmaceutically acceptable carrier.

In yet another aspect, a method of preventing, arresting progression of, or ameliorating vision loss associated with macular degeneration in a subject is provided. The method includes administering to the subject an effective concentration of a composition comprising any recombinant adeno-associated virus (AAV) described herein and a pharmaceutically acceptable carrier.

In yet another aspect, a method of preventing, arresting progression of, or ameliorating vision loss associated with macular dystrophy in a subject is provided. The method includes administering to the subject an effective concentration of a composition comprising any recombinant adeno-associated virus (AAV) described herein and a pharmaceutically acceptable carrier.

In a further aspect, a patient is administered intravitreally, intravenously, subretinally, or retrobulbarly an AAV that has the BMI1 gene within its genome. In a further aspect, administration of this BMI1 containing AAV increases the expression of BMI1 in the retinal ganglion cells. This increased protection reduces the severity of glaucoma, ischemic optic neuropathies and/or retinopathies.

The method includes administering to the subject an effective concentration of a composition comprising any recombinant adeno-associated virus (AAV) described herein and a pharmaceutically acceptable carrier.

In another aspect, a host or target cell transfected with an AAV or nucleic acid molecule as described herein is provided.

Definitions

Reference in this specification to "one embodiment/aspect" or "an embodiment/aspect" means that a particular feature, structure, or characteristic described in connection with the embodiment/aspect is included in at least one embodiment/aspect of the disclosure. The use of the phrase "in one embodiment/aspect" or "in another embodiment/aspect" in various places in the specification are not necessarily all referring to the same embodiment/aspect, nor are separate or alternative embodiments/aspects mutually exclusive of other embodiments/aspects. Moreover, various features are described which may be exhibited by some embodiments/aspects and not by others. Similarly, various requirements are described which may be requirements for some embodiments/aspects but not other embodiments/aspects. Embodiment and aspect can in certain instances be used interchangeably.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. It will be appreciated that the same thing can be said in more than one way.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461,463 (CCPA 1976) (emphasis in the original); see also MPEP § 2111.03. Thus, the term "consisting essentially of" when used in a claim of this invention is not intended to be interpreted to be equivalent to "comprising." Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al., (1983) *J Virology* 45:555; Chiarini et al., (1998) *J. Virology* 71:6823; Chiarini et al., (1999) *J. Virology* 73:1309; Bantel-Schaal et al., (1999) *J. Virology* 73:939; Xiao et al., (1999) *J. Virology* 73:3994; Muramatsu et al., (1996) *Virology* 221:208; Shade et al., (1986) *J. Viral.* 58:921; Gao et al., (2002) *Proc. Nat. Acad. Sci. USA* 99:11854; Moris et al., (2004) *Virology* 33-:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences.

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of a heterologous nucleic acid(s) of interest.

As used here, "systemic tropism" and "systemic transduction" (and equivalent terms) indicate that the virus capsid or virus vector of the invention exhibits tropism for and/or transduces tissues throughout the body (e.g., brain, eye, lung, skeletal muscle, heart, liver, kidney and/or pancreas). In embodiments of the invention, systemic transduction of the eye or ocular system is observed. In other embodiments, systemic transduction of cardiac muscle tissues is achieved.

As used herein, "selective tropism" or "specific tropism" means delivery of virus vectors to and/or specific transduction of certain target cells and/or certain tissues.

A vector for use in gene therapy can include a virus. In an embodiment, a virus is a retrovirus, herpes simplex virus or an adenovirus.

Physical methods for introduction of a nucleotide sequence encoding a BMI1 gene include intraocular injection of a naked DNA. Additional methods include electroporation, sonoporation and using a gene gun, which shoots DNA coated gold particles into the cell using high pressure gas. Other methods include magnetofection and hydrodynamic delivery.

DNA delivery can be improved through the use of lipoplexes, polymersomes, polyplexes, dendrimers, inorganic nanoparticles and cell-penetrating peptides.

Unless indicated otherwise, "efficient transduction" or "efficient tropism," or similar terms, can be determined by reference to a suitable control (e.g., at least about 50%, 60%, 70%, 80%, 85%, 90%, 95%, 100%, 125%, 150%, 175%, 200%, 250%, 300%, 350%, 400%, 500% or more of the transduction or tropism, respectively, of the control). In particular embodiments, the virus vector efficiently transduces or has efficient tropism for neuronal cells and cardiomyocytes. Suitable controls will depend on a variety of factors including the desired tropism and/or transduction profile.

Similarly, it can be determined if a virus "does not efficiently transduce" or "does not have efficient tropism" for a target tissue, or similar terms, by reference to a suitable control. In particular embodiments, the virus vector does not efficiently transduce (i.e., has does not have efficient tropism) for liver, kidney, gonads and/or germ cells. In particular embodiments, transduction (e.g., undesirable transduction) of tissue(s) (e.g., liver) is 25% or less, is 20% or less, 10% or less, 5% or less, 1% or less, 0.1% or less of the level of transduction of the desired target tissue(s) (e.g., skeletal muscle, diaphragm muscle, cardiac muscle and/or cells of the central nervous system).

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only and is not intended to further limit the scope and meaning of the disclosure or of any exemplified term. Likewise, the disclosure is not limited to various embodiments given in this specification.

The term "subject" or "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human. In an embodiment, a "subject" of diagnosis or treatment is a prokaryotic or a eukaryotic cell, a tissue culture, a tissue, or an animal, e.g. a mammal, including a human.

The term "AAV" refers to adeno-associated virus and may be used to refer to the virus itself or derivatives thereof. The term covers all subtypes and both naturally occurring and recombinant forms, except where required otherwise. Adeno-associated virus (AAV), a member of the Parvovirus family, is a small nonenveloped, icosahedral virus with single-stranded linear DNA genomes of 4.7 kilobases (kb) to 6 kb. AAV is assigned to the genus, Dependovirus, because the virus was discovered as a contaminant in purified adenovirus stocks. AAV's life cycle includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer. There are twelve AAV serotypes, with AAV1, AAV2, AAV4, AAV5 and AAV8. There are also different variants of AAVs, including chimerics or psuedotypes, haploids, polyploids and self-complimentary.

In an embodiment, an AAV is a variant, derivative, modified or other AAV that differs from the wild-type AAV strain of the same serotype. An example of a variant of AAV2 is AAV2.7m8, which is an engineered capsid with a 10-amino acid insertion (the 7m8 peptide) in adeno-associated virus (AAV) surface variable region VIII (VR-VIII) resulting in the alteration of an antigenic region of AAV2 and the ability to efficiently transduce retina cells following intravitreal administration or other cells such as inner or outer ear hair cells. Another example is AAV8BP2 and AAV9-7m8. The 7m8 peptide can also be inserted into AAV5 and AAV8. A further example is AAV2.7m8-Nr2e3.

In an embodiment, "an effective amount" refers, without limitation, to the amount of the defined component sufficient to achieve the desired therapeutic result. In an embodiment, that result can be effective cancer treatment.

In an embodiment, as used herein, the terms "treating," "treatment" and the like are used herein, without limitation, to mean obtaining a desired pharmacologic and/or physiologic effect. The effect may be prophylactic in terms of completely or partially preventing a disorder or sign or symptom thereof, and/or may be therapeutic in terms of amelioration of the symptoms of the disease or infection, or a partial or complete cure for a disorder and/or adverse effect attributable to the disorder.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In representative embodiments an "isolated" nucleotide is enriched by at least about 10-fold, 100-fold, 1000-fold, 10,000-fold or more as compared with the starting material. If DNA is the polynucleotide, the DNA can be a B-DNA, A-DNA, D-DNA, Z-DNA, naked DNA and cDNA. If RNA is the polynucleotide, the RNA can be an mRNA, rRNA, 7 SL RNA, SRP RNA, tRNA, tmRNA, snRNA, snoRNA, SmY RNA, scaRNA, gRNA, YRNA, TERC, SL RNA, aRNA, asRNA, cis-NAT, crRNA, lncRNA, miRNA, piRNA, siRNA, shRNA, tasiRNA, rasiRNA, 7sK RNA, sRNA, 5S rRNA, 5.8 SrRNA, SSU rRNA, LUS rRNA, NoRC RNA, 6S RNA, SsrS RNA, asmiRNA, crRNA, CRISPR RNA, diRNA, endo-siRNA, exRNA, lincRNA, lncRNA, mrpNRA, nat-siRNA, snRNA, shRNA, circRNA, cfRNA, pre-mRNA, YRNA or eRNA.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In representative embodiments an "isolated" polypeptide is enriched by at least about 10-fold, 100-fold, 1000-fold, 10,000-fold or more as compared with the starting material.

An "isolated cell" refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

As used herein, the term "recombinant" refers to polypeptides or polynucleotides that do not exist naturally and which may be created by combining polynucleotides or polypeptides in arrangements that would not normally occur together. The term can refer to a polypeptide produced through a biological host, selected from a mammalian expression system, an insect cell expression system, a yeast expression system, and a bacterial expression system.

As used herein, by "isolate" or "purify" (or grammatical equivalents) a virus vector or virus particle or population of virus particles, it is meant that the virus vector or virus particle or population of virus particles is at least partially separated from at least some of the other components in the starting material. In representative embodiments an "isolated" or "purified" virus vector or virus particle or population of virus particles is enriched by at least about 10-fold, 100-fold, 1000-fold, 10,000-fold or more as compared with the starting material.

A "therapeutic polypeptide" is a polypeptide that can alleviate, reduce, prevent, delay and/or stabilize symptoms that result from an absence or defect in a protein in a cell or subject and/or is a polypeptide that otherwise confers a benefit to a subject, e.g., anti-cancer effects or improvement in transplant survivability or induction of an immune response.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some preventative benefit is provided to the subject.

The terms "heterologous nucleotide sequence" and "heterologous nucleic acid molecule" are used interchangeably herein and refer to a nucleic acid sequence that is not naturally occurring in the virus. Generally, the heterologous nucleic acid molecule or heterologous nucleotide sequence comprises an open reading frame that encodes a polypeptide and/or nontranslated RNA of interest (e.g., for delivery to a cell and/or subject).

The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

An "AAV virus" or "AAV viral particle" or "rAAV vector particle" refers to a viral particle composed of at least one AAV capsid protein (typically by all of the capsid proteins of a wild-type AAV) and an encapsulated polynucleotide rAAV vector. If the particle comprises a heterologous polynucleotide (i.e. a polynucleotide other than a wild-type AAV genome, such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virus or viral particle is one that comprises a polynucleotide component that it is capable of delivering into a cell for which the viral species is tropic. The term does not necessarily imply any replication capacity of the virus. As used herein, an "infectious" virus or viral particle is one that can access a target cell, can infect a target cell, and can express a heterologous nucleic acid in a target cell. Thus, "infectivity" refers to the ability of a viral particle to access a target cell, infect a target cell, and express a heterologous nucleic acid in a target cell. Infectivity can refer to in vitro infectivity or in vivo infectivity. Assays for counting infectious viral particles are described elsewhere in this disclosure and in the art. Viral infectivity can be expressed as the ratio of infectious viral particles to total viral particles. Total viral particles can be expressed as the number of viral genome copies. The ability of a viral particle to express a heterologous nucleic acid in a cell can be referred to as "transduction." The ability of a viral particle to express a heterologous nucleic acid in a cell can be assayed using a number of techniques, including assessment of a marker gene, such as a green fluorescent protein (GFP) assay (e.g., where the virus comprises a nucleotide sequence encoding GFP), where GFP is produced in a cell infected with the viral particle and is detected and/or measured; or the measurement of a produced protein, for example by an enzyme-linked immunosorbent assay (ELISA).

A "replication-competent" virus (e.g. a replication-competent AAV) refers to a phenotypically wild-type virus that is infectious and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per 104 rAAV particles, less than about 1 rcAAV per $10^8$ rAAV particles, less than about 1 rcAAV per $10^{12}$ rAAV particles, or no rcAAV).

The virus vectors of the invention can further be "targeted" virus vectors (e.g., having a directed tropism) and/or a "hybrid" parvovirus (i.e., in which the viral TRs and viral capsid are from different parvoviruses) as described in international patent publication WO 00/28004 and Chao et al., (2000) *Molecular Therapy* 2:619.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

Further, the viral capsid or genomic elements can contain other modifications, including insertions, deletions and/or substitutions.

A "chimeric" capsid protein as used herein means an AAV capsid protein that has been modified by substitutions in one or more (e.g., 2, 3, 4, 5, 6, 7, 8, 9, 10, etc) amino acid residues in the amino acid sequence of the capsid protein relative to wild type, as well as insertions and/or deletions of one or more (e.g., 2, 3, 4, 5, 6, 7, 8, 9, 10, etc) amino acid residues in the amino acid sequence relative to wild type. In some embodiments, complete or partial domains, functional regions, epitopes, etc., from one AAV serotype can replace the corresponding wild type domain, functional region, epitope, etc. of a different AAV serotype, in any combination, to produce a chimeric capsid protein of this invention. Production of a chimeric capsid protein can be carried out according to protocols well known in the art and a large number of chimeric capsid proteins are described in the literature as well as herein that can be included in the capsid of this invention.

The term "variant" as used herein includes modifications or chemical equivalents of the amino acid and nucleotide sequences disclosed herein that perform substantially the same function as the proteins or nucleic acid molecules disclosed herein in substantially the same way. For example, variants of proteins disclosed herein include, without limitation, conservative amino acid substitutions. Variants of proteins disclosed herein also include additions and deletions to the proteins disclosed herein. In addition, variant peptides and variant nucleotide sequences include analogs and chemical derivatives thereof.

"Conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For example, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The protein encoded by the BMI1 gene can have amino acid additions, deletions, or substitutions. A modified amino acid sequence is a sequence that is different from the native amino acid sequence due to a deletion, an insertion, a non-conservative or conservative substitution or combinations thereof of one or more amino acid residues. In one embodiment, the modification is a point mutation. In one aspect, the modified therapeutic peptide does not have a naturally occurring sequence.

The amino acid substitutions may be conservative or non-conservative. A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The most commonly occurring exchanges are Ala/Ser, Val/Ile, Asp/Glu, Thr/Ser, Ala/Gly, Ala/Thr, Ser/Asn, Ala/Val, Ser/Gly, Ala/Pro, Lys/Arg, Asp/Asn, Leu/Ile, Leu/Val, Ala/Glu and Asp/Gly, in both directions. Amino acid exchanges in proteins and peptides, which do not generally alter the activity of the proteins or peptides, are known in the art (H. Neurath, R. L. Hill, The Proteins, Academic Press, New York, 1979).

The term "derivative of a protein" refers to a protein having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

In one embodiment, a modified therapeutic protein disclosed herein can have an addition, deletion or substitution in the amino acid sequence of the protein for any amino acid. In another embodiment, a modified therapeutic protein disclosed herein can have 1-13 amino acid additions, deletions, or substitutions. In one aspect, the therapeutic protein has at least 1, at least 2, at least 3, at least 4, at least 5, at least 6, at least 7, at least 8, at least 9, at least 10, at least 11, at least 12 or at least 13 amino acid additions, substitutions, or deletions. Substitutions can be conservative or non-conservative. In another aspect, the therapeutic protein can have at most 13, at most 12, at most 11, at most 10, at most 9, at most 8, at most 7, at most 6, at most 5, at most 4, at most 3, at most 2, or at most 1 amino acid additions, substitutions, or deletions. In yet another aspect, the therapeutic protein can have 1-13, 1-12, 1-10, 1-9, 1-8, 1-7, 1-6, 1-5, 1-4, 1-3, 1-2, 2-4, 2-13, 2-12, 2-10, 2-9, 2-8, 2-7, 2-6, 2-5, 2-4, 2-3, 3-4, 3-13, 3-12, 3-10, 3-9, 3-8, 3-7, 3-6, 3-5, 3-4, 4-12, 4-10, 4-9, 4-8, 4-7, 4-6, 4-5, 5-12, 5-10, 5-9, 5-8, 5-7, 5-6, 5-5, 6-12, 6-10, 6-9, 6-8, 6-7, 7-13, 7-12, 7-10, 7-9, 7-8, 8-13, 8-12, 8-10, 8-9, 9-13, 9-12, 9-10, 10-12, 11-13, 11-12 or 12-13 amino acid additions, substitutions or deletions.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to the full length of the reference sequence, usually about 25 to 100, or 50 to about 150, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=-4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=-4, and a comparison of both strands.

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "gene" refers to a polynucleotide containing at least one open reading frame that is capable of encoding a particular protein after being transcribed and translated.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

The term "control element" or "control sequence" refers to a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

The term "operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

The term "expression vector" refers to a vector comprising a region which encodes a polypeptide of interest and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally occurring, wild-type AAV, and the encoded heterologous gene product is a gene product not normally encoded by a naturally occurring, wild-type AAV.

As used herein, the term "homologous recombination" means a type of genetic recombination in which nucleotide sequences are exchanged between two similar or identical molecules of DNA. Homologous recombination also produces new combinations of DNA sequences. These new combinations of DNA represent genetic variation. Homologous recombination is also used in horizontal gene transfer to exchange genetic material between different strains and species of viruses.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be affected, for example, by transfecting a cell with a recombinant plasmid or other polynucleotide through any process known in the art, such as electroporation, calcium phosphate precipitation, or contacting with a polynucleotide-liposome complex. Genetic alteration may also be affected, for example, by transduction or infection with a DNA or RNA virus or viral vector. Generally, the genetic element is introduced into a chromosome or mini chromosome in the cell; but any alteration that changes the phenotype and/or genotype of the cell and its progeny is included in this term.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher et al., *J. Biol. Chem.* 273(52):35095-35101 (1998).

As used herein, the term "gene editing," "Genome editing," or "genome engineering" means a type of genetic engineering in which DNA is inserted, deleted or replaced in the genome of a living organism using engineered nucleases, or "molecular scissors". These nucleases create site-specific double-strand breaks (DSBs) at desired locations in the genome.

As used herein, the term "gene delivery" means a process by which foreign DNA is transferred to host cells for applications of gene therapy.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced which is also inheritable by progeny of the altered cell.

An "isolated" plasmid, nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

The term "retinal pigment epithelium," "RPE" or "Muller" cells refers to a single layer of epithelial cells lining the posterior segment of the eye. The layer is located between the light-sensing photoreceptor cells and the choriocapillaris. Similar to other epithelial cell types, RPE cells are polarized.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

As used herein, "gene replacement therapy" refers to administration to the recipient of exogenous genetic material encoding a therapeutic agent and subsequent expression of the administered genetic material in situ. This includes injection into the eye's vitreous. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material, which has a beneficial effect on the mammalian recipient. Thus, "therapeutic agent" embraces both therapeutic and prophylactic molecules having nucleic acid or protein components.

The term "ailment" refers to a disease, illness or medical condition. An ailment can be, for example, an ophthalmic ailment such as retinal degeneration, retinal dystrophy, macular degeneration or macular dystrophy.

A number of genetic eye diseases are known. Therapeutic agents effective against these diseases are also known, since it is the protein/enzyme known to be deficient in these disorders. In certain embodiments, the disease or condition is retinal degeneration, retinal dystrophy, macular degeneration or macular dystrophy.

The term "BMI1", "Bmi1", "Bmi-1" or "BMI-1 gene" refers to "B lymphoma Mo-MLV insertion region 1 homolog." Studies suggest that overexpression of BMI1 plays an important role in several types of cancer.

The term "Polycomb complex protein BMI1," "polycomb group RING finger protein 4," "PCGF4," "RING finger protein 51" or "RNF51" refers to a protein that in humans is encoded by the Bmi1 gene (B cell-specific Moloney murine leukemia virus integration site 1). Polycomb group (PcG) proteins are chromatin-modifying proteins that play an important role in development. They also regulate cell proliferation, senescence, and tumorigenesis. Polycomb group (PcG) protein BMI1 is an important regulator of cell proliferation.

The term "Mel-18," "polycomb group ring finger 2," or "PCGF2" refers to a closely related PcG protein. The Mel-18 gene product is structurally similar to Bmi1. Studies suggest that Bmi1 and Mel-18 regulate overlapping and unique sets of genes.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The terms "sequence identity" "percent sequence identity" or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g., of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length and may be up to about 700 amino acids. Examples of suitable fragments are described herein.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. In the examples, AAV alignments are performed using the published AAV2 or AAV1 sequences as a reference point. However, one of skill in the art can readily select another AAV sequence as a reference. Alignments are performed using any of a variety of publicly or commercially available Multiple Sequence Alignment Programs. Examples of such programs include, "Clustal W", "CAP Sequence Assembly", "MAP", and "MEME", which are accessible through Web Servers on the internet.

The term "serotype" is a distinction with respect to an AAV having a capsid which is serologically distinct from other AAV serotypes. Serologic distinctiveness is determined on the basis of the lack of cross-reactivity between antibodies to the AAV as compared to other AAV.

The term "exogenous genetic material" refers to a nucleic acid or an oligonucleotide, either natural or synthetic, that is not naturally found in the cells; or if it is naturally found in the cells, it is not transcribed or expressed at biologically significant levels by the cells. Thus, "exogenous genetic material" includes, for example, a non-naturally occurring nucleic acid that can be transcribed into anti-sense RNA, as well as a "heterologous gene" (i.e., a gene encoding a protein which is not expressed or is expressed at biologically insignificant levels in a naturally occurring cell of the same type).

Alternatively, the amino acid can be a modified amino acid residue and/or can be an amino acid that is modified by post-translation modification (e.g., acetylation, amidation, formylation, hydroxylation, methylation, phosphorylation or sulfatation). A non-naturally occurring amino acid can be an "unnatural" amino acid, which can be used to chemically link molecules of interest to the AAV capsid protein or other type of viral vector.

As used herein, the term "homologous recombination" means a type of genetic recombination in which nucleotide sequences are exchanged between two similar or identical molecules of DNA. Homologous recombination also produces new combinations of DNA sequences that can represent a genetic variation. Homologous recombination is also used in horizontal gene transfer to exchange genetic material between different strains and species of viruses.

As used herein, the term "gene editing," "Genome editing," or "genome engineering" means a type of genetic engineering in which DNA is inserted, deleted or replaced in the genome of a living organism using engineered nucleases, or "molecular scissors." These nucleases create site-specific double-strand breaks (DSBs) at desired locations in the genome.

As used herein, the term "gene delivery" means a process by which foreign DNA is transferred to host cells for applications of gene therapy. As used herein, the term "CRISPR" stands for Clustered Regularly Interspaced Short Palindromic Repeats, which are the hallmark of a bacterial defense system that forms the basis for CRISPR-Cas9 genome editing technology.

In some embodiments, the AAV particle of this invention can be synthetic viral vector designed to display a range of desirable phenotypes that are suitable for different in vitro and in vivo applications. Thus, in one embodiment, the present invention provides an AAV particle comprising an adeno-associated virus (AAV).

In the certain embodiments, the mammalian recipient has a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material, which has a beneficial effect on the mammalian recipient. Thus, "therapeutic agent" embraces both therapeutic and prophylactic molecules having nucleic acid (e.g., antisense RNA) and/or protein components.

DETAILED DESCRIPTION OF EMBODIMENTS

Figure 1A:
FIGS. 1A-1C show a picture of a young healthy retina (FIG. 1A), a picture of an eye with moderate dry macular degeneration (FIG. 1B), and a picture of advanced dry macular degeneration with sub-foveal geographic atrophy (FIG. 1C).

The particular configurations discussed in the following description are non-limiting examples that can be varied and are cited merely to illustrate at least one embodiment and are not intended to limit the scope thereof.

The present invention provides a method of treating an ailment such as an eye/ocular disease in a mammal by administering a viral vector described herein to the mammal. In certain embodiments, the mammal is human. In certain embodiments, the disease is retinal degeneration, retinal dystrophy, macular degeneration or macular dystrophy.

Polycomb group proteins form large multimeric complexes that silence specific target genes by modifying chromatin organization. The Polycomb group protein BMI1 is a component of the polycomb repressive complex1 (PRC1) which promotes chromatin compaction and gene repression through its mono-ubiquitin ligase activity on histone H2A at lysine 119. In an embodiment of the invention, BMI1 protein is transduced into ocular cells of a patient affected by an ailment (e.g. retinal degeneration, retinal dystrophy, macular degeneration, or macular dystrophy). The Applicants have found that expression of BMI1 protein in retinal pigment epithelium (RPE) cells can alleviate retinopathies. Specifically, its expression can prevent, arrest the progression of and/or ameliorate signs and symptoms of retinal and/or macular degeneration. In some cases, vision loss associated with a retinopathy can be prevented or restored.

BMI1 protein includes native or naturally occurring BMI1 protein and any derivative or variant of a BMI1 protein. This includes BMI1 proteins with additions, deletions and substitutions of amino acids. This also includes BMI1 proteins with additions, deletions and substitutions of one or more nucleotides in the nucleic acid sequence encoding a BMI1 protein.

Embodiments include the introduction and expression of BMI1 protein in retinal pigment epithelium (RPE) cells. Transduction can be achieved by a vector such as an adeno-associated virus (AAV) vector, an adenoviral vector, a retrovirus, or a lentivirus vector based on human immunodeficiency virus or feline immunodeficiency virus. Examples of such AAVs can be found, for example, in Davidson et al., PNAS (2000) 97:3428-3432. The AAV and lentiviruses can confer lasting expression while the adenovirus can provide transient expression.

An expression vector can include a promoter for controlling transcription of the heterologous gene. The promoter can be an inducible or constitutive promoter. The expression system is suitable for administration to the mammalian recipient. The expression system can include a plurality of non-immortalized genetically modified cells, each cell containing at least one recombinant gene encoding at least one therapeutic agent.

The cell expression system can be formed in vivo. According to another aspect, a method for treating a mammalian recipient in vivo is provided. The method includes introducing an expression vector for expressing a heterologous gene product into a cell of the patient in situ, such as via intraocular administration. To form the expression system in vivo, an expression vector for expressing the therapeutic agent is introduced in vivo into the mammalian recipient.

AAV Vectors

Adeno associated virus (AAV) is a small (20 nm), non-pathogenic virus that can be useful in treating human diseases. A construct is generated that surrounds a promoter linked to a target gene with AAV inverted terminal repeat (ITR) sequences.

In one embodiment, a viral vector of the disclosure is an AAV vector. An "AAV" vector refers to an adeno-associated virus and can be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are many known serotypes of primate AAVs (e.g., AAV1, AAV2, AAV3, AAV4, AAV5, AAV6, AAV7, AAV8, AAV9, AAV 10, AAV-Rh74, and AAVRh10, and modified capsids of these serotypes). The abbreviation "rAAV" refers to recombinant adeno-associated virus, also referred to as a recombinant AAV vector (or "rAAV vector").

An "AAV virus" or "AAV viral particle" refers to a viral particle composed of at least one AAV capsid protein (preferably by all of the capsid proteins of a wild-type AAV) and an encapsulated polynucleotide. If the particle comprises heterologous polynucleotide (i.e., a polynucleotide other than a wild-type AAV genome such as a transgene to be delivered to a mammalian cell), it is typically referred to as "rAAV".

In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

Other Vectors

The present invention also includes other non-AAV vectors for use in treating a disease of the eye with the BMI1 protein. These include retroviruses, parvoviruses, lentiviruses, adenoviruses and herpes simplex viruses. Each of these non-AAV vectors allow for similar transfer of a gene, like BMI1 into a cell through either insertion of the nucleic acid of the gene into the host cell's genome or through episomal expression of a nucleic acid molecule, like a plasmid that does not integrate into the host cell's genome. It is understood that for each of the non-AAV vectors identified below, one of skill in the art would know how to create a vector for expression of a gene like BMI1 in a host cell.

Parvovirus Vectors

A non-AAV viral vector that can be used in the present invention are Parvovirus vectors.

Parvovirus vectors are relatively small DNA animal viruses that contain a linear, single-stranded DNA genome. Parvoviruses include autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, mouse minute virus, bovine parvovirus, canine parvovirus, chicken parvovirus, feline panleukopenia virus, feline parvovirus, goose parvovirus, and B19 virus. Other autonomous parvoviruses are known to those skilled in the art.

A parvovirus vector of the present invention may be a "hybrid" parvovirus. A parvovirus may have a "chimeric" capsid that contains sequences from different parvoviruses or other viruses or a "targeted" capsid (e.g., a directed tropism). A parvovirus may also have a polyploid capsid wherein the different capsid proteins are derived from different serotypes of parvovirus or even different viruses. Duplexed parvovirus vector genome may contain sufficient packaging sequences for encapsidation within the selected parvovirus capsid.

Adenoviral Vectors

Another non-AAV viral vector are Adenoviral vectors. An adenoviral vector is effective in transducing many, but not all mammalian cell types. Additionally, adenoviral vectors have the advantage of having the DNA of the vector remain episomal, without integration into the host genome.

Letiviral Vectors

Another non-AAV viral vector are Lentiviruses, which are a species of retroviruses that insert their genetic material into dividing and non-dividing cells, with the result that the genetic material is integrated into the host genome, allowing for continued expression. Lentivirus vectors have the ability to infect non-dividing cells and can insert their genetic material into their host cells' genome. Lentivirus vectors have been used to treat disease like Diabetes mellitus, Murine haemophilia A, prostate cancer, chronic granulomatous disease, rheumatoid arthritis and vascular diseases.

*L. monocytogenes*

*L. monocytogenes* is an intracellular bacterium that can be used to deliver a gene encoding a protein into a cell.

Poxvirus Vectors

A further non-AAV viral vector of the present invention are Poxvirus vectors. Among the Poxvirus vectors are vaccinia virus (VACV) and myxoma virus (MYXV), both of which can be used as viral vectors for the transmission of a gene into a cell. Vaccinia virus (VV) vectors are known to transduce a wide range of cells and result in transient expression. Poxvirus vectors have a substantial genome that can have large portions replaced, so that insertion of large DNA fragments up to 25 kb in size are possible. Other Poxvirus vectors such as modified vaccinia ankara (MVA) or fowl pox virus, which do not replicate completely in mammalian cells, can also be used to transduce cells.

Herpes Simplex Virus

Another non-AAV viral vector are Herpes Simplex Virus vectors or HSV vectors. They possess a double stranded linear genome of 150 kb. HSV shows tropism for a wide variety of cell types with high infectivity for both dividing and nondividing cells. HSV expresses over 80 different genes, many of which are not essential for its replication cycle. HSV therefore has the potential to carry a substantial payload, allowing the insertion of multiple or very large transgenes in highly defective vectors described below. The latent HSV genome does not integrate into cellular DNA, but remains episomal as a closed circular molecule, thus avoiding the risks of insertional mutagenesis.

Nonviral/Nonbacterial Gene Delivery Methods

Nonviral/Nonbacterial gene delivery methods use synthetic or natural compounds or physical forces to deliver a piece of DNA or RNA into a cell. Cell or tissue specificity with these methods can be achieved by harnessing cell-specific functionality in the design. Methods include needle and jet injection to transfer a gene into a cell. Jet injection includes use of a gene gun, also called ballistic DNA transfer or DNA-coated particle bombardment. Another method for transferring a gene into a cell is sonoporation, which uses ultrasound waves to create plasma membrane defects by acoustic cavitation. Sonoporation can be done in combination with contrast agents or microbubbles.

Gene transfer into cells can also be accomplished using cationic lipids. Cationic lipids have a structure consisting of a positively charged hydrophilic head and a hydrophobic tail that are connected via a linker structure. The most commonly seen hydrophilic head groups are primary, secondary, tertiary amines, or quaternary ammonium salts. However, guanidino, imidazole, pyridinium, phosphorus, and arsenic groups have also been developed. Cationic polymers can also be used for gene transfer into cells. Upon mixing with DNA or RNA, these polymers form nanosized complexes, often called polyplexes. Typically, polyplexes are more stable than lipoplexes.

Gene transfer can also be done using inorganic nanoparticles that are normally prepared from metals (e.g., iron, gold, silver), inorganic salts, or ceramics (e.g., phosphate or carbonate salts of calcium, magnesium, or silicon). The metal ion-based salts produce complexes with typical size range of 10-100 nm in diameter. The surface of these nanoparticles can be coated to facilitate DNA binding or targeted gene delivery. The small particle size offers several advantages including that they usually bypass most of the physiological and cellular barriers and produce higher gene expression. Nanoparticles have the ability to efficiently transfect postmitotic cells. Additionally, they tend to show no or low toxicity and are inert to immune responses. Supraparamagnetic iron oxide-based nanoparticles can also provide magnetic responsiveness in a magnetic field and can provide magnetic field—guided targeted delivery of the DNA.

Methods for Introducing Genetic Material into Cells

The present invention also provides a method to deliver an agent to the eye of a subject, by transducing ocular cells with a viral vector so that the transduced ocular cells express the therapeutic agent and deliver the agent to the eye of the subject. In certain embodiments, the agent is BMI1 protein. In certain embodiments, the ocular cells are retinal pigment epithelium (RPE) cells.

The exogenous genetic material (e.g., a cDNA encoding one or more therapeutic proteins) is introduced into the cell ex vivo or in vivo by genetic transfer methods, such as transfection or transduction, to provide a genetically modified cell. Various expression vectors (i.e., vehicles for facilitating delivery of exogenous genetic material into a target cell) are known to one of ordinary skill in the art.

As used herein, "transfection of cells" refers to the acquisition by a cell of new genetic material by incorporation of added DNA. Thus, transfection refers to the insertion of nucleic acid into a cell using physical or chemical methods. Several transfection techniques are known to those of ordinary skill in the art including calcium phosphate DNA co-precipitation; DEAE-dextran; electroporation; cationic liposome-mediated transfection; and tungsten particle-facilitated microparticle bombardment. Strontium phosphate DNA co-precipitation is another possible transfection method.

In contrast, "transduction of cells" refers to the process of transferring nucleic acid into a cell using a DNA or RNA virus. An RNA virus (i.e., a retrovirus) for transferring a nucleic acid into a cell is referred to herein as a transducing chimeric retrovirus. Exogenous genetic material contained within the retrovirus is incorporated into the genome of the transduced cell. A cell that has been transduced with a chimeric DNA virus (e.g., an adenovirus carrying a cDNA encoding a therapeutic agent), will not have the exogenous genetic material incorporated into its genome but will be capable of expressing the exogenous genetic material that is retained extrachromosomally within the cell.

The expression systems that may be used for purposes of the invention include but are not limited to mammalian cell systems (e.g., COS, CHO, BHK, 293, 3T3)

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion an "enhancer" is simply any non-translated DNA sequence which works contiguous with the coding sequence (in cis) to change the basal transcription level dictated by the promoter. The exogenous genetic material may be introduced into the cell genome immediately downstream from the promoter so that the promoter and coding sequence are operatively linked so as to permit transcription of the coding sequence. A retroviral expression vector may include an exogenous promoter element to control transcription of the inserted exogenous gene. Such exogenous promoters include both constitutive and inducible promoters.

Naturally occurring constitutive promoters control the expression of essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent (e.g., transcription under control of the metallothionein promoter is greatly increased in the presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified cell. If the gene encoding the therapeutic agent is under the control of an inducible promoter, delivery of the therapeutic agent in situ is triggered by exposing the genetically modified cell in situ to conditions for permitting transcription of the therapeutic agent, e.g., by intraperitoneal injection of specific inducers of the inducible promoters which control transcription of the agent. For example, in situ expression by genetically modified cells of a therapeutic agent encoded by a gene under the control of the metallothionein promoter, is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene, (i.e., whether the promoter is constitutive or inducible, strong or weak); (2) the number of copies of the exogenous gene that are inserted into the cell; (3) the number of transduced/transfected cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the therapeutic agent by the genetically modified cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid encoding the therapeutic agent, the expression vector may include a selection gene, for example, a neomycin resistance gene, for facilitating selection of cells that have been transfected or transduced with the expression vector. Alternatively, the cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the scope of one of ordinary skill in the art without undue experimentation.

The therapeutic agent can be targeted for delivery to an extracellular, intracellular or membrane location. If it is desirable for the gene product to be secreted from the cells, the expression vector is designed to include an appropriate secretion "signal" sequence for secreting the therapeutic gene product from the cell to the extracellular milieu. If it is desirable for the gene product to be retained within the cell, this secretion signal sequence is omitted. In a similar manner, the expression vector can be constructed to include "retention" signal sequences for anchoring the therapeutic agent within the cell plasma membrane. For example, all membrane proteins have hydrophobic transmembrane regions, which stop translocation of the protein in the membrane and do not allow the protein to be secreted. The construction of an expression vector including signal sequences for targeting a gene product to a particular location is deemed to be within the scope of one of ordinary skill in the art without the need for undue experimentation.

The selection and optimization of a particular expression vector for expressing a specific gene product in an isolated cell is accomplished by obtaining the gene, potentially with one or more appropriate control regions (e.g., promoter, insertion sequence); preparing a vector construct comprising the vector into which is inserted the gene; transfecting or transducing cultured cells in vitro with the vector construct; and determining whether the gene product is present in the cultured cells. In certain embodiments, a virus from the adeno-associated virus family is used. In certain embodiments, an expression vector for gene therapy based on AAV8 is used.

Thus, as will be apparent to one of ordinary skill in the art, a variety of suitable viral expression vectors are available for transferring exogenous genetic material into cells. The selection of an appropriate expression vector to express a therapeutic agent for a particular condition amenable to gene replacement therapy and the optimization of the conditions for insertion of the selected expression vector into the cell, are within the scope of one of ordinary skill in the art without the need for undue experimentation.

In an alternative embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (ProMega, Madison, Wis.). However, the efficiency of transfection by these methods is highly dependent on the nature of the target cell and accordingly, the conditions for optimal transfection of nucleic acids into cells using the above-mentioned procedures must be optimized. Such optimization is within the scope of one of ordinary skill in the art without the need for undue experimentation.

Although, for convenience, reference is made herein to any of AAV1, AAV2, AAV4, AAV5 or AAV8, it is to be understood that mutations in the homologous region of other AAV serotype capsids are also encompassed by the invention. As used herein, the term "wild type" refers to the native AAV sequence without mutation in aa 587-595 (using AAV8 numbering) of the capsid protein. However, it is not intended that only naturally occurring AAV be the source of the wild type sequence. Useful herein are non-naturally occurring AAV, including, without limitation, recombinant, modified or altered, chimeric, hybrid, synthetic, artificial, etc., AAV. This includes AAV with mutations in regions of the capsid other than in aa 587-595, provided they are used as the "starting sequence" for generating the mutant capsid described herein.

Disclosed herein is a system and method of delivering a gene product to a retinal epithelial cell of a subject. The method includes administering to the individual a subject rAAV virion as described above. The methods generally involve introducing a subject rAAV virion into the eye of an individual, where the rAAV virion enters a retinal cell in the eye and where the gene product encoded by the heterologous polynucleotide present in the rAAV virion is produced in the retinal cell. The eye can be one that has impaired vision and/or that has an ocular disease (e.g. retinal degeneration, retinal dystrophy, macular degeneration, or macular dystrophy). Alternatively, the eye can be one that is at elevated risk of developing impaired vision and/or an ocular disease. Introduction of a subject rAAV virion into the eye of an individual can be carried out by intraocular injection, by intravitreal injection, by intravitreal implant, subretinal injection, suprachoroidal administration, intravenous administration, or by any other convenient mode or route of administration known in the art.

In retinal gene therapy, AAV is capable of "transducing" RPE cells by entering the cells and expressing the therapeutic DNA sequence. Because the cells of the retina are non-dividing, AAV can continue to persist and provide expression of the therapeutic DNA sequence over a long time period that can last several years.

A further aspect of the invention is a method of administering the virus vector and/or virus capsid to subjects. Administration of the virus vectors and/or capsids according to the present invention to a human subject or an animal in need thereof can be by any means known in the art. Optionally, the virus vector and/or capsid is delivered in a treatment-effective or prevention-effective dose in a pharmaceutically acceptable carrier.

In some cases, a subject AAV virion, when introduced (e.g., via intravitreal injection) into an eye of an individual, provides for high level production of the heterologous gene product encoded by the AAV in the eye. For example, a heterologous polypeptide encoded by the AAV can be produced in the eye at a level of from about 1 μg to about 50 μg, or greater than 50 μg. As another example, a heterologous polypeptide encoded by the AAV can be produced in the vitreous fluid of the eye at a level of from about 100 μg/mL to about 5000 μg/mL vitreous fluid, e.g., from about 100 μg/mL to about 500 μg/mL, from about 500 μg/mL to about 1000 μg/mL, from about 1000 μg/mL to about 2000 μg/mL, from about 2000 μg/mL to about 3000 μg/mL, from about 3000 μg/mL to about 4000 μg/mL, or from about 4000 μg/mL to about 5000 μg/mL. In some cases, a polypeptide encoded by the AAV can be produced in the vitreous fluid of the eye at a level of greater than 5000 μg/mL vitreous fluid.

In some cases, a subject AAV virion, when introduced (e.g., via intravitreal injection) into an eye of an individual, provides for production of the heterologous gene product encoded by the AAV in at least about 10%, at least about 15%, at least about 20%, at least about 25%, at least about 30%, at least about 35%, at least about 40%, at least about 50% at least about 60%, at least about 70%, at least about 80%, or more than 80%, of the Muller cells in the eye.

In some embodiments, a subject AAV virion, when introduced (e.g., via intravitreal injection) into an eye of an individual, provides for production of the heterologous gene product encoded by the AAV for a period of time from about 2 days to about 6 months, e.g., from about 2 days to about 7 days, from about 1 week to about 4 weeks, from about 1 month to about 2 months, or from about 2 months to about 6 months. In some embodiments, a subject AAV virion, when introduced (e.g., via intravitreal injection) into an eye of an individual, provides for production of the heterologous gene product encoded by the AAV for a period of time of more than 6 months, e.g., from about 6 months to 20 years or more, or greater than 1 year, e.g., from about 6 months to about 1 year, from about 1 year to about 2 years, from about 2 years to about 5 years, from about 5 years to about 10 years, from about 10 years to about 15 years, from about 15 years to about 20 years, or more than 20 years.

The gene product can be a polypeptide or a nucleic acid. Nucleic acid gene products include, e.g., an interfering RNA (e.g., an shRNA, an siRNA, and the like), a ribozyme, an antisense RNA, and an aptamer, as described above.

Pharmaceutical Compositions

Another embodiment is a pharmaceutical composition. The pharmaceutical composition can include the above-described polypeptides and a pharmaceutically acceptable carrier. The pharmaceutical composition can be used for treating a condition amenable to gene replacement therapy. The exogenous genetic material can include a heterologous gene that encodes a therapeutic agent for treating the ailment or condition. The pharmaceutical composition can also contain an amount of polypeptides sufficient to deliver a therapeutically effective dose of the therapeutic agent to the patient.

In one embodiment, the recombinant AAV (rAAV) containing the desired transgene and cell-specific promoter for use in the target ocular cells as detailed above is optionally assessed for contamination by conventional methods and then formulated into a pharmaceutical composition intended for subretinal or intravitreal injection. Such formulation involves the use of a pharmaceutically and/or physiologically acceptable vehicle or carrier, particularly one suitable for administration to the eye, e.g., by subretinal injection, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In certain embodiments of the methods described herein, the pharmaceutical composition described above is administered to the subject by subretinal injection. In other embodiments, the pharmaceutical composition is administered by intravitreal, suprachoroidal or orbital injection. Other forms of administration that may be useful in the methods described herein include, but are not limited to, direct delivery to a desired organ (e.g., the eye), oral, inhalation, intranasal, intratracheal, intravenous, intramuscular, subcutaneous, intradermal, and other parental routes of administration. Routes of administration may be combined, if desired.

Furthermore, in certain embodiments it is desirable to perform non-invasive retinal imaging and functional studies to identify areas of specific ocular cells to be targeted for therapy. In these embodiments, clinical diagnostic tests are employed to determine the precise location(s) for one or more subretinal injection(s). These tests may include ophthalmoscopy, electroretinography (ERG) (particularly the b-wave measurement), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, etc. These, and other desirable tests, are described in International Patent Application No. PCT/US2013/022628. In view of the imaging and functional studies, in some embodiments, one or more injections are performed in the same eye in order to target different areas of retained bipolar cells. The volume and viral titer of each injection are determined individually, as further described below, and may be the same or different from other injections performed in the same, or contralateral, eye. In another embodiment, a single, larger volume injection is made in order to treat the entire eye. In one embodiment, the volume and concentration of the rAAV composition is selected so that only a specific region of ocular cells is impacted. In another embodiment, the volume and/or concentration of the rAAV composition is a greater amount, in order reach larger portions of the eye, including non-damaged ocular cells.

The composition can be delivered in a volume of from about 0.1 µL to about 1 mL, including all numbers within the range, depending on the size of the area to be treated, the viral titer used, the route of administration, and the desired effect of the method. In one embodiment, the volume is about 50 µL. In another embodiment, the volume is about 70 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 250 µL. In another embodiment, the volume is about 300 µL. In another embodiment, the volume is about 450 µL. In another embodiment, the volume is about 500 µL. In another embodiment, the volume is about 600 µL. In another embodiment, the volume is about 750 µL. In another embodiment, the volume is about 850 µL. In another embodiment, the volume is about 1000 µL.

An effective concentration of a recombinant adeno-associated virus carrying a nucleic acid sequence encoding the desired transgene under the control of the cell-specific promoter sequence desirably ranges from about $10^7$ to $10^{13}$ vector genomes per milliliter (vg/mL) (also called genome copies/mL (GC/mL)). The rAAV infectious units are measured as described in S. K. McLaughlin et al, 1988 J. Virol., 62:1963, which is incorporated herein by reference. Preferably, the concentration in the retina is from about $1.5 \times 10^9$ vg/mL to about $1.5 \times 10^{12}$ vg/mL, and more preferably from about $1.5 \times 10^9$ vg/mL to about $1.5 \times 10^{11}$ vg/mL. In one embodiment, the effective concentration is about $1.4 \times 10^8$ vg/mL. In one embodiment, the effective concentration is about $3.5 \times 10^{10}$ vg/mL. In another embodiment, the effective concentration is about $5.6 \times 10^{11}$ vg/mL. In another embodiment, the effective concentration is about $5.3 \times 10^{12}$ vg/mL. In yet another embodiment, the effective concentration is about 1.5×10¹² vg/mL. In another embodiment, the effective concentration is about 1.5×10¹³ vg/mL. In one embodiment, the effective dosage (total genome copies delivered) is from about 10⁷ to 10¹³ vector genomes. It is desirable that the lowest effective concentration of virus be utilized in order to reduce the risk of undesirable effects, such as toxicity, retinal dysplasia and detachment. Still other dosages and administration volumes in these ranges may be selected by the attending physician, taking into account the physical state of the subject, preferably human, being treated, the age of the subject, the particular ocular disorder and the degree to which the disorder, if progressive, has developed. For extra-ocular delivery, the dosage will be increased according to the scale-up from the retina. Intravenous delivery, for example may require doses on the order of 1.5×10¹³ vg/kg.

A "therapeutically effective amount" will fall in a relatively broad range that can be determined through experimentation and/or clinical trials. Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. For example, for in vivo injection, e.g., injection directly into the eye, a therapeutically effective dose will be on the order of from about 10⁶ to about 10¹⁵ of the rAAV virions, e.g., from about 10⁸ to 10¹² rAAV virions. For example, for in vivo injection, e.g., injection directly into the eye, a therapeutically effective dose will be on the order of from about 10⁶ to about 10¹² infectious units, e.g., from about 10⁸ to about 10¹² infectious units. Other effective dosages can be readily established by one of ordinary skill in the art through routine trials establishing dose response curves. In an embodiment, exemplary doses for achieving therapeutic effects are titers of at least about 10⁵, 10⁶, 10⁷, 10⁸, 10⁹, 10¹⁰, 10¹¹, 10¹², 10¹³, 10¹⁴, 10¹⁵ transducing units, optionally about 10⁸ to about 10¹³ transducing units.

In some cases, a therapeutically effective amount of a subject rAAV virion is an amount that, when administered to an individual (e.g., administered via intravitreal injection into an eye (e.g., a visually impaired eye; an eye having an ocular disease; an eye that is at risk of developing an ocular disease) of the individual) in one or more doses, is effective to slow the progression of retinal degeneration in the individual. For example, a therapeutically effective amount of a subject rAAV virion can be an amount that, when administered to an individual (e.g., administered via intravitreal injection to an individual) in one or more doses, is effective to slow the progression of retinal degeneration by at least about 15%, at least about 20%, at least about 25%, at least about 30%, at least about 40%, at least about 50%, at least about 60%, at least about 70%, at least about 80%, or more than 80%, compared to the progression of retinal degeneration in the absence of treatment with the rAAV virion.

In some cases, a therapeutically effective amount of a subject rAAV virion is an amount that, when administered to an individual (e.g., administered via intravitreal injection into an eye of the individual) in one or more doses, is effective to improve vision in the individual. For example, a therapeutically effective amount of a subject rAAV virion can be an amount that, when administered to an individual (e.g., administered via intravitreal injection into an eye of the individual) in one or more doses, is effective to improve vision by at least about 15%, at least about 20%, at least about 25%, at least about 30%, at least about 40%, at least about 50%, at least about 60%, at least about 70%, at least about 80%, or more than 80%, compared to the individual's vision in the absence of treatment with the rAAV virion.

In another embodiment, a therapeutically effective amount of a subject rAAV virion can be an amount that, when administered to an individual (e.g., administered via intravitreal injection into an eye of the individual) in one or more doses, is effective to improve vision by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% compared to the individual's vision in the absence of treatment with the rAAV virion.

In another embodiment, a therapeutically effective amount of a subject rAAV virion can be an amount that, when administered to an individual (e.g., administered via intravitreal injection into an eye of the individual) in one or more doses, is effective to improve vision by no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, no more than 50%, no more than 51%, no more than 52%, no more than 53%, no more than 54%, no more than 55%, no more than 56%, no more than 57%, no more than 58%, no more than 59%, no more than 60%, no more than 61%, no more than 62%, no more than 63%, no more than 64%, no more than 65%, no more than 66%, no more than 67%, no more than 68%, no more than 69%, no more than 70%, no more than 71%, no more than 72%, no more than 73%, no more than 74%, no more than 75%, no more than 76%, no more than 77%, no more than 78%, no more than 79%, no more than 80%, no more than 81%, no more than 82%, no more than 83%, no more than 84%, no more than 85%, no more than 86%, no more than 87%, no more than 88%, no more than 89%, no more than 90%, no more than 91%, no more than 92%, no more than 93%, no more than 94%, no more than 95%, no more than 96%, no more than 97%, no more than 98%, no more than 99% or no more than 100% compared to the individual's vision in the absence of treatment with the rAAV virion.

In another embodiment, a therapeutically effective amount of a subject rAAV virion can be an amount that, when administered to an individual (e.g., administered via intravitreal injection into an eye of the individual) in one or more doses, is effective to improve vision by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or at least 100% compared to the individual's vision in the absence of treatment with the rAAV virion.

In some cases, a therapeutically effective amount of a subject rAAV virion is an amount that, when administered to an individual (e.g., administered via intravitreal injection into an eye of the individual) in one or more doses, is effective to decrease the rate of vision loss in an eye with impaired vision.

Improvement of clinical symptoms are monitored by one or more methods known to one skilled in the art, for example, tests of functional vision, such as visual acuity, visual field, contrast sensitivity, color vision, mobility, and light sensitivity. Clinical symptoms may also be monitored by anatomical or physiological means, such as indirect ophthalmoscopy, fundus photography, fluorescein angiography, optical coherence tomography, electroretinography (full-field, multifocal, or other), external eye examination, slit lamp biomicroscopy, applanation tonometry, pachymetry, autorefaction, or other measures of functional vision.

In particular embodiments, more than one administration (e.g., two, three, four, five, six, seven, eight, nine, 10, etc., or more administrations) may be employed to achieve the desired level of gene expression over a period of various intervals, e.g., hourly, daily, weekly, monthly, yearly, etc. Dosing can be single dosage or cumulative (serial dosing), and can be readily determined by one skilled in the art. For instance, treatment of a disease or disorder may comprise a one-time administration of an effective dose of a pharmaceutical composition virus vector disclosed herein. Alternatively, treatment of a disease or disorder may comprise multiple administrations of an effective dose of a virus vector carried out over a range of time periods, such as, e.g., once daily, twice daily, thrice daily, once every few days, or once weekly. The timing of administration can vary from individual to individual, depending upon such factors as the severity of an individual's symptoms. For example, an effective dose of a virus vector disclosed herein can be administered to an individual once every six months for an indefinite period of time, or until the individual no longer requires therapy. A person of ordinary skill in the art will recognize that the condition of the individual can be monitored throughout the course of treatment and that the effective amount of a virus vector disclosed herein that is administered can be adjusted accordingly.

In an embodiment, the period of administration of a virus vector is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Multiple doses of a subject rAAV virion can be administered to an individual in need thereof. Where multiple doses are administered over a period of time, an active agent is administered once a month to about once a year, from about once a year to once every 2 years, from about once every 2 years to once every 5 years, or from about once every 5 years to about once every 10 years, over a period of time. For example, a subject rAAV virion is administered over a period of from about 3 months to about 2 years, from about 2 years to about 5 years, from about 5 years to about 10 years, from about 10 years to about 20 years, or more than 20 years. The actual frequency of administration, and the actual duration of treatment, depends on various factors.

As an example, a subject method of treating an ocular disorder can include administering an initial dose of a subject rAAV virion; and administering at least a second dose (a subsequent dose) of the rAAV virion. Where two or more subsequent doses are administered, the subsequent dose(s) can be separated in time from each other by at least one month, at least 3 to 6 months, at least 6 months to 1 year, at least 1 year to 5 years, at least 5 years to 10 years, at least 10 years to 20 years, or more than 20 years.

Other ocular diseases that can be prevented, ameliorated or treated using the method described herein include acute macular neuroretinopathy; macular telangiectasia; Behcet's disease; choroidal neovascularization; diabetic eye disease; uveitis; histoplasmosis; macular degenerations, such as age-related macular degeneration, Sorsby's macular dystrophy, early or intermediate (dry) macular degeneration, or a form of advanced macular degeneration, such as exudative macular degeneration or geographic atrophy; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative and non-proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal effusion; a posterior ocular condition caused by or influenced by an ocular laser treatment; posterior ocular conditions caused by or influenced by a photodynamic therapy, photocoagulation, radiation retinopathy; epiretinal membrane disorders; central or branch retinal vein occlusion; central or branch artery occlusion, anterior ischemic optic neuropathy, diabetic retinal dysfunction; retinitis pigmentosa; retinoschisis; and glaucoma.

In an embodiment, a patient is administered an AAV that has the BMI1 gene within its genome by intravitreal, intravenous, subretinal, or retrobulbar. In a further embodiment, administration of the BMI1 containing AAV increases the expression of BMI1 in the retinal ganglion cells. This increased protection results in a reduction in the severity of glaucoma, ischemic optic neuropathies and/or retinopathies.

In another embodiment, the subject has shown clinical signs of an ocular disorder. Clinical signs of an ocular disorder can include decreased peripheral vision, decreased central (reading) vision, decreased night vision, loss of color perception, reduction in visual acuity, decreased photoreceptor function, and pigmentary changes. In one embodiment, the subject shows degeneration of the outer nuclear layer (ONL). In another embodiment, the subject has been diagnosed with an ocular disorder. In yet another embodiment, the subject has not yet shown clinical signs of an ocular disorder.

In one embodiment, the subject has become symptomatic for the ocular disorder. In another embodiment, the subject has 10% or more photoreceptor damage/loss. In another embodiment, the subject has 20% or more photoreceptor damage/loss. In another embodiment, the subject has 30% or more photoreceptor damage/loss. In another embodiment, the subject has 40% or more photoreceptor damage/loss. In another embodiment, the subject has 50% or more photoreceptor damage/loss. In another embodiment, the subject has 60% or more photoreceptor damage/loss. In another embodiment, the subject has 70% or more photoreceptor damage/loss. In another embodiment, the subject has 80% or more photoreceptor damage/loss. In another embodiment, the subject has 90% or more photoreceptor damage/loss. In another embodiment, the subject's bipolar cell circuitry to ganglion cells and optic nerve remains intact.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

Delivery of Viruses

In another aspect, the present invention provides a method for delivery of a transgene to a host which involves transfecting or infecting a selected host cell with a recombinant viral vector generated with the AAV9/HU.14 sequences (or functional fragments thereof) of the invention. Methods for delivery are well known to those of skill in the art and are not a limitation of the present invention.

In one desirable embodiment, the invention provides a method for AAV-mediated delivery of a transgene to a host. This method involves transfecting or infecting a selected host cell with a recombinant viral vector containing a selected transgene under the control of sequences that direct expression thereof and AAV9 capsid proteins.

Optionally, a sample from the host may be first assayed for the presence of antibodies to a selected AAV source (e.g., a serotype). A variety of assay formats for detecting neutralizing antibodies are well known to those of skill in the art. The selection of such an assay is not a limitation of the present invention. See, e.g., Fisher et al, Nature Med., 3(3):306-312 (March 1997) and W. C. Manning et al, Human Gene Therapy, 9:477-485 (Mar. 1, 1998). The results of this assay may be used to determine which AAV vector containing capsid proteins of a particular source are preferred for delivery, e.g., by the absence of neutralizing antibodies specific for that capsid source.

In one aspect of this method, the delivery of vector with AAV capsid proteins of the invention may precede or follow delivery of a gene via a vector with a different AAV capsid protein. Thus, gene delivery via rAAV vectors may be used for repeat gene delivery to a selected host cell. Desirably, subsequently administered rAAV vectors carry the same transgene as the first rAAV vector, but the subsequently administered vectors contain capsid proteins of sources (and preferably, different serotypes) which differ from the first vector. For example, if a first vector has AAV9/HU.14 capsid proteins, subsequently administered vectors may have capsid proteins selected from among the other AAV, optionally, from another serotype or from another clade.

Optionally, multiple rAAV vectors can be used to deliver large transgenes or multiple transgenes by co-administration of rAAV vectors concatamerize in vivo to form a single vector genome. In such an embodiment, a first AAV may carry an expression cassette which expresses a single transgene (or a subunit thereof) and a second AAV may carry an expression cassette which expresses a second transgene (or a different subunit) for co-expression in the host cell. A first AAV may carry an expression cassette which is a first piece of a polycistronic construct (e.g., a promoter and transgene, or subunit) and a second AAV may carry an expression cassette which is a second piece of a polycistronic construct (e.g., transgene or subunit and a polyA sequence). These two pieces of a polycistronic construct concatamerize in vivo to form a single vector genome that co-expresses the transgenes delivered by the first and second AAV. In such embodiments, the rAAV vector carrying the first expression cassette and the rAAV vector carrying the second expression cassette can be delivered in a single pharmaceutical composition. In other embodiments, the two or more rAAV vectors are delivered as separate pharmaceutical compositions which can be administered substantially simultaneously, or shortly before or after one another.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. US-2004-0013645-AI). The virus vectors and/or virus capsids disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or capsids may likewise be produced with any solid particulate medicament aerosol generator, by techniques known in the pharmaceutical art.

The above-described recombinant vectors may be delivered to host cells according to published methods. The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

The vectors can be administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the eye (optionally via the hepatic artery) or lung), oral, inhalation, intranasal, intratracheal, intraarterial, intraocular, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 0.1 mL to about 100 mL of solution containing concentrations of from about 1×109 to 1×1016 genomes of the virus vector. A preferred human dosage for delivery to large organs (e.g., liver, muscle, heart and lung) may be about 5×1016 to 5×1013 AAV genomes per 1 kg, at a volume of about 1 to 100 mL. A preferred dosage for delivery to eye is generally about 5×109 to 5×1012 genome copies, at a volume of about 0.1 mL to 1 mL. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention.

Examples of therapeutic products and immunogenic products for delivery by the AAV-containing vectors of the invention are provided below. These vectors may be used for a variety of therapeutic or vaccinal regimens, as described herein. Additionally, these vectors may be delivered in combination with one or more other vectors or active ingredients in a desired therapeutic and/or vaccinal regimen.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Retinitis pigmentosa, by comparison, is characterized by retinal degeneration. In representative embodiments, retinitis pigmentosa can be treated by intraocular (e.g., intravitreal) administration or other delivery method of a delivery vector encoding one or more neurotrophic factors.

Age-related macular degeneration involves both angiogenesis and retinal degeneration. In an embodiment, this disorder can be treated by administering the inventive deliver vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other aspects of this embodiment, a virus vector, including an AAV, reduces the severity of an eye disease or disorder by, e.g., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or at least 100%.

In other aspects of this embodiment, a virus vector, including an AAV, reduces the severity of an eye disease or disorder by, e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100%.

In other aspects of this embodiment, a virus vector, including an AAV, reduces the severity of an eye disease or disorder by, e.g., no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, no more than 50%, no more than 51%, no more than 52%, no more than 53%, no more than 54%, no more than 55%, no more than 56%, no more than 57%, no more than 58%, no more than 59%, no more than 60%, no more than 61%, no more than 62%, no more than 63%, no more than 64%, no more than 65%, no more than 66%, no more than 67%, no more than 68%, no more than 69%, no more than 70%, no more than 71%, no more than 72%, no more than 73%, no more than 74%, no more than 75%, no more than 76%, no more than 77%, no more than 78%, no more than 79%, no more than 80%, no more than 81%, no more than 82%, no more than 83%, no more than 84%, no more than 85%, no more than 86%, no more than 87%, no more than 88%, no more than 89%, no more than 90%, no more than 91%, no more than 92%, no more than 93%, no more than 94%, no more than 95%, no more than 96%, no more than 97%, no more than 98%, no more than 99% or no more than 100%.

In yet other aspects of this embodiment, a virus vector reduces the severity of a disease or disorder from, e.g., no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, no more than 50%, no more than 51%, no more than 52%, no more than 53%, no more than 54%, no more than 55%, no more than 56%, no more than 57%, no more than 58%, no more than 59%, no more than 60%, no more than 61%, no more than 62%, no more than 63%, no more than 64%, no more than 65%, no more than 66%, no more than 67%, no more than 68%, no more than 69%, no more than 70%, no more than 71%, no more than 72%, no more than 73%, no more than 74%, no more than 75%, no more than 76%, no more than 77%, no more than 78%, no more than 79%, no more than 80%, no more than 81%, no more than 82%, no more than 83%, no more than 84%, no more than 85%, no more than 86%, no more than 87%, no more than 88%, no more than 89%, no more than 90%, no more than 91%, no more than 92%, no more than 93%, no more than 94%, no more than 95%, no more than 96%, no more than 97%, no more than 98%, no more than 99% or no more than 100%.

In yet other aspects of this embodiment, a virus vector reduces the severity of a disease or disorder from, e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100%.

In yet other aspects of this embodiment, a virus vector reduces the severity of a disease or disorder from, e.g., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or at least 100%.

In yet other aspects of this embodiment, a virus vector reduces the severity of a disease or disorder from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A virus vector, including an AAV as disclosed herein may comprise a solvent, emulsion or other diluent in an amount sufficient to dissolve a virus vector disclosed herein. In other aspects of this embodiment, a virus vector including an AAV as disclosed herein may comprise a solvent, emulsion or a diluent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a virus vector, including an AAV as disclosed herein may comprise a solvent, emulsion or other diluent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

Aspects of the present specification disclose, in part, treating an individual suffering from a disease or disorder. As used herein, the term "treating," refers to reducing or eliminating in an individual a clinical symptom of the disease or disorder; or delaying or preventing in an individual the onset of a clinical symptom of a disease or disorder. For example, the term "treating" can mean reducing a symptom of a condition characterized by a disease or disorder, by, e.g., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or at least 100%. The actual symptoms associated with a specific disease or disorder are well known and can be determined by a person of ordinary skill in the art by taking into account factors, including, without limitation, the location of the disease or disorder, the cause of the disease or disorder, the severity of the disease or disorder, and/or the tissue or organ affected by the disease or disorder. Those of skill in the art will know the appropriate symptoms or indicators associated with a specific type of disease or disorder and will know how to determine if an individual is a candidate for treatment as disclosed herein.

In aspects of this embodiment, a therapeutically effective amount of a virus vector, including an AAV as disclosed herein reduces a symptom associated with a disease or disorder by, e.g., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or at least 100%.

In other aspects of this embodiment, a therapeutically effective amount of a virus vector, including an AAV as disclosed herein reduces a symptom associated with a disease or disorder by, e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100%.

In other aspects of this embodiment, a therapeutically effective amount of a virus vector, including an AAV as disclosed herein reduces a symptom associated with a disease or disorder by, e.g., no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, no more than 50%, no more than 51%, no more than 52%, no more than 53%, no more than 54%, no more than 55%, no more than 56%, no more than 57%, no more than 58%, no more than 59%, no more than 60%, no more than 61%, no more than 62%, no more than 63%, no more than 64%, no more than 65%, no more than 66%, no more than 67%, no more than 68%, no more than 69%, no more than 70%, no more than 71%, no more than 72%, no more than 73%, no more than 74%, no more than 75%, no more than 76%, no more than 77%, no more than 78%, no more than 79%, no more than 80%, no more than 81%, no more than 82%, no more than 83%, no more than 84%, no more than 85%, no more than 86%, no more than 87%, no more than 88%, no more than 89%, no more than 90%, no more than 91%, no more than 92%, no more than 93%, no more than 94%, no more than 95%, no more than 96%, no more than 97%, no more than 98%, no more than 99% or no more than 100%.

In other aspects of this embodiment, a therapeutically effective amount of a virus vector, including an AAV as disclosed herein reduces a symptom associated with a disease or disorder by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a virus vector, including an AAV as disclosed herein reduces a symptom associated with disease or disorder by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In one embodiment, a virus vector, including an AAV as disclosed herein is capable of increasing the level and/or amount of a protein encoded in the virus vector that is administered to a patient by, e.g., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or at least 100% as compared to a patient not receiving the same treatment.

In another embodiment, a virus vector, including an AAV as disclosed herein is capable of increasing the level and/or amount of a protein encoded in the virus vector that is administered to a patient by, e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100%.

In a further embodiment, a virus vector, including an AAV as disclosed herein is capable of increasing the level and/or amount of a protein encoded in the virus vector that is administered to a patient by, e.g., no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, no more than 50%, no more than 51%, no more than 52%, no more than 53%, no more than 54%, no more than 55%, no more than 56%, no more than 57%, no more than 58%, no more than 59%, no more than 60%, no more than 61%, no more than 62%, no more than 63%, no more than 64%, no more than 65%, no more than 66%, no more than 67%, no more than 68%, no more than 69%, no more than 70%, no more than 71%, no more than 72%, no more than 73%, no more than 74%, no more than 75%, no more than 76%, no more than 77%, no more than 78%, no more than 79%, no more than 80%, no more than 81%, no more than 82%, no more than 83%, no more than 84%, no more than 85%, no more than 86%, no more than 87%, no more than 88%, no more than 89%, no more than 90%, no more than 91%, no more than 92%, no more than 93%, no more than 94%, no more than 95%, no more than 96%, no more than 97%, no more than 98%, no more than 99% or no more than 100%.

In other aspects of this embodiment, a virus vector, including an AAV is capable of reducing the severity of a disease or disorder in an individual suffering from the disease or disorder by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In aspects of this embodiment, a therapeutically effective amount of a virus vector, including an AAV as disclosed herein increases the amount of protein that is encoded within the virus vector in an individual by, e.g., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or at least 100% as compared to an individual not receiving the same treatment.

In further aspects of this embodiment, a therapeutically effective amount of a virus vector, including an AAV as disclosed herein increases the amount of protein that is encoded within the virus vector in an individual by, e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100%.

In other aspects of this embodiment, a therapeutically effective amount of a virus vector, including an AAV as disclosed herein increases the amount of protein that is encoded within the virus vector in an individual by, e.g., no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, no more than 50%, no more than 51%, no more than 52%, no more than 53%, no more than 54%, no more than 55%, no more than 56%, no more than 57%, no more than 58%, no more than 59%, no more than 60%, no more than 61%, no more than 62%, no more than 63%, no more than 64%, no more than 65%, no more than 66%, no more than 67%, no more than 68%, no more than 69%, no more than 70%, no more than 71%, no more than 72%, no more than 73%, no more than 74%, no more than 75%, no more than 76%, no more than 77%, no more than 78%, no more than 79%, no more than 80%, no more than 81%, no more than 82%, no more than 83%, no more than 84%, no more than 85%, no more than 86%, no more than 87%, no more than 88%, no more than 89%, no more than 90%, no more than 91%, no more than 92%, no more than 93%, no more than 94%, no more than 95%, no more than 96%, no more than 97%, no more than 98%, no more than 99% or no more than 100%.

In other aspects of this embodiment, a therapeutically effective amount of a virus vector, including an AAV as disclosed herein reduces the severity of a disease or disorder or maintains the severity of a disease or disorder in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a virus vector, including an AAV as disclosed herein reduces or maintains the severity of a disease or disorder in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

A virus vector is administered to an individual or a patient. An individual or a patient is typically a human being, but can be an animal, including, but not limited to, dogs, cats, birds, cattle, horses, sheep, goats, reptiles and other animals, whether domesticated or not.

In an embodiment, diseases of the eye, including the retina, and RPE cells can be treated using an AAV, wherein the AAV comprises a recipient AAV that can be any AAV serotype and a donor capsid that is selected from one or more of AAV1, AAV2, AAV3, AAV4, AAV5, AAV7, AAV8, AAV9 or AAV10. In one embodiment, the recipient AAV is an AAV2 and the donor capsid that is selected from one or more of AAV1, AAV2, AAV3, AAV4, AAV5, AAV7, AAV8, AAV9 or AAV10. In another embodiment, the recipient AAV is AAV3 and the donor capsid is selected from AAV1, AAV2, AAV3, AAV4, AAV5, AAV7, AAV8, AAV9 or AAV10.

According to another aspect, a method for forming the above-described pharmaceutical composition is provided. The method includes introducing an expression vector for expressing a heterologous gene product into a cell to form a genetically modified cell and placing the genetically modified cell in a pharmaceutically acceptable carrier.

While the invention is primarily described for treating an eye ailment such as retinal degeneration, retinal dystrophy, macular degeneration or macular dystrophy, it is understood that the invention is not so limited and can be used to assist with other ailments.

Aspects of the present specification disclose, in part, treating an individual suffering from a retinopathy. As used herein, the term "treating," refers to reducing or eliminating in an individual a clinical symptom of the retinopathy; or delaying or preventing in an individual the onset of a clinical symptom of the retinopathy. For example, the term "treating" can mean reducing a symptom of a condition characterized by a retinopathy, including, but not limited to, vision, by, e.g., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or at least 100%. The actual symptoms associated with cancer are well known and can be determined by a person of ordinary skill in the art. Those of skill in the art will know the appropriate symptoms or indicators associated with a specific type of retinopathy and will know how to determine if an individual is a candidate for treatment as disclosed herein.

In another aspect, a pharmaceutical composition disclosed herein reduces the severity of a symptom of a disorder associated with a retinopathy. In aspects of this embodiment, a pharmaceutical composition disclosed herein reduces the severity of a symptom of a disorder associated with a retinopathy by, e.g., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or at least 100%.

In aspects of this embodiment, a pharmaceutical composition disclosed herein reduces the severity of a symptom of a disorder associated with a retinopathy by, e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100%.

In aspects of this embodiment, a pharmaceutical composition disclosed herein reduces the severity of a symptom of a disorder associated with a retinopathy by, e.g., no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, no more than 50%, no more than 51%, no more than 52%, no more than 53%, no more than 54%, no more than 55%, no more than 56%, no more than 57%, no more than 58%, no more than 59%, no more than 60%, no more than 61%, no more than 62%, no more than 63%, no more than 64%, no more than 65%, no more than 66%, no more than 67%, no more than 68%, no more than 69%, no more than 70%, no more than 71%, no more than 72%, no more than 73%, no more than 74%, no more than 75%, no more than 76%, no more than 77%, no more than 78%, no more than 79%, no more than 80%, no more than 81%, no more than 82%, no more than 83%, no more than 84%, no more than 85%, no more than 86%, no more than 87%, no more than 88%, no more than 89%, no more than 90%, no more than 91%, no more than 92%, no more than 93%, no more than 94%, no more than 95%, no more than 96%, no more than 97%, no more than 98%, no more than 99% or no more than 100%.

In other aspects of this embodiment, a pharmaceutical composition disclosed herein reduces the severity of a symptom of a disorder associated with a retinopathy by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In aspects of this embodiment, a therapeutically effective amount of a pharmaceutical composition disclosed herein reduces a symptom associated with retinopathy by, e.g., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or at least 100%.

In aspects of this embodiment, a therapeutically effective amount of a pharmaceutical composition disclosed herein reduces a symptom associated with retinopathy by, e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100%.

In aspects of this embodiment, a therapeutically effective amount of a pharmaceutical composition disclosed herein reduces a symptom associated with retinopathy by, e.g., no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, no more than 50%, no more than 51%, no more than 52%, no more than 53%, no more than 54%, no more than 55%, no more than 56%, no more than 57%, no more than 58%, no more than 59%, no more than 60%, no more than 61%, no more than 62%, no more than 63%, no more than 64%, no more than 65%, no more than 66%, no more than 67%, no more than 68%, no more than 69%, no more than 70%, no more than 71%, no more than 72%, no more than 73%, no more than 74%, no more than 75%, no more than 76%, no more than 77%, no more than 78%, no more than 79%, no more than 80%, no more than 81%, no more than 82%, no more than 83%, no more than 84%, no more than 85%, no more than 86%, no more than 87%, no more than 88%, no more than 89%, no more than 90%, no more than 91%, no more than 92%, no more than 93%, no more than 94%, no more than 95%, no more than 96%, no more than 97%, no more than 98%, no more than 99% or no more than 100%.

In other aspects of this embodiment, a therapeutically effective amount of a pharmaceutical composition disclosed herein reduces a symptom associated with retinopathy by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a pharmaceutical composition disclosed herein reduces a symptom associated with retinopathy by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, a therapeutically effective amount of a pharmaceutical composition disclosed herein generally is in the range of about 0.001 mg/kg to about 100 mg/kg and administered, for example, every 3, 5, 7, 10 or 14 days.

In aspects of this embodiment, an effective amount of a pharmaceutical composition disclosed herein may be, e.g., at least 0.001 mg/kg, at least 0.01 mg/kg, at least 0.1 mg/kg, at least 1.0 mg/kg, at least 5.0 mg/kg, at least 10 mg/kg, at least 15 mg/kg, at least 20 mg/kg, at least 25 mg/kg, at least 30 mg/kg, at least 35 mg/kg, at least 40 mg/kg, at least 45 mg/kg, or at least 50 mg/kg and administered, for example, every 3, 5, 7, 10 or 14 days. In other aspects of this embodiment, an effective amount of a pharmaceutical composition disclosed herein may be in the range of, e.g., about 0.001 mg/kg to about 10 mg/kg, about 0.001 mg/kg/day to about 15 mg/kg, about 0.001 mg/kg to about 20 mg/kg, about 0.001 mg/kg to about 25 mg/kg, about 0.001 mg/kg to about 30 mg/kg, about 0.001 mg/kg to about 35 mg/kg, about 0.001 mg/kg to about 40 mg/kg, about 0.001 mg/kg to about 45 mg/kg, about 0.001 mg/kg to about 50 mg/kg, about 0.001 mg/kg to about 75 mg/kg, or about 0.001 mg/kg to about 100 mg/kg and administered, for example, every 3, 5, 7, 10 or 14 days. In yet other aspects of this embodiment, an effective amount of a pharmaceutical composition disclosed herein may be in the range of, e.g., about 0.01 mg/kg to about 10 mg/kg, about 0.01 mg/kg to about 15 mg/kg, about 0.01 mg/kg to about 20 mg/kg, about 0.01 mg/kg to about 25 mg/kg, about 0.01 mg/kg to about 30 mg/kg, about 0.01 mg/kg to about 35 mg/kg, about 0.01 mg/kg to about 40 mg/kg, about 0.01 mg/kg to about 45 mg/kg, about 0.01 mg/kg to about 50 mg/kg, about 0.01 mg/kg to about 75 mg/kg, or about 0.01 mg/kg to about 100 mg/kg and administered, for example, every 3, 5, 7, 10 or 14 days. In still other aspects of this embodiment, an effective amount of a pharmaceutical composition disclosed herein may be in the range of, e.g., about 0.1 mg/kg to about 10 mg/kg, about 0.1 mg/kg to about 15 mg/kg, about 0.1 mg/kg to about 20 mg/kg, about 0.1 mg/kg to about 25 mg/kg, about 0.1 mg/kg to about 30 mg/kg, about 0.1 mg/kg to about 35 mg/kg, about 0.1 mg/kg to about 40 mg/kg, about 0.1 mg/kg to about 45 mg/kg, about 0.1 mg/kg to about 50 mg/kg, about 0.1 mg/kg to about 75 mg/kg, or about 0.1 mg/kg to about 100 mg/kg and administered, for example, every 3, 5, 7, 10 or 14 days.

Dosing can be single dosage or cumulative (serial dosing), and can be readily determined by one skilled in the art. For instance, treatment of a retinopathy may comprise a one-time administration of an effective dose of a pharmaceutical composition disclosed herein. Alternatively, treatment of a retinopathy may comprise multiple administrations of an effective dose of a pharmaceutical composition carried out over a range of time periods, such as, e.g., once daily, twice daily, thrice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

A pharmaceutical composition or retinopathy therapeutic is administered to an individual. An individual is typically a human being, but can be an animal, including, but not limited to, dogs, cats, birds, cattle, horses, sheep, goats, reptiles and other animals, whether domesticated or not. Typically, any individual who is a candidate for treatment is a candidate with some form of retinopathy.

In one aspect, a pharmaceutical composition disclosed herein reduces a symptom of a disorder associated with a retinopathy. In aspects of this embodiment, a pharmaceutical composition disclosed herein reduces a symptom of a disorder associated with a retinopathy by, e.g., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or at least 100%.

In another aspect, a pharmaceutical composition disclosed herein reduces a symptom of a disorder associated with a retinopathy. In aspects of this embodiment, a pharmaceutical composition disclosed herein reduces a symptom of a disorder associated with a retinopathy by, e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100%.

In another aspect, a pharmaceutical composition disclosed herein reduces a symptom of a disorder associated with a retinopathy. In aspects of this embodiment, a pharmaceutical composition disclosed herein reduces a symptom of a disorder associated with a retinopathy by, e.g., no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, no more than 50%, no more than 51%, no more than 52%, no more than 53%, no more than 54%, no more than 55%, no more than 56%, no more than 57%, no more than 58%, no more than 59%, no more than 60%, no more than 61%, no more than 62%, no more than 63%, no more than 64%, no more than 65%, no more than 66%, no more than 67%, no more than 68%, no more than 69%, no more than 70%, no more than 71%, no more than 72%, no more than 73%, no more than 74%, no more than 75%, no more than 76%, no more than 77%, no more than 78%, no more than 79%, no more than 80%, no more than 81%, no more than 82%, no more than 83%, no more than 84%, no more than 85%, no more than 86%, no more than 87%, no more than 88%, no more than 89%, no more than 90%, no more than 91%, no more than 92%, no more than 93%, no more than 94%, no more than 95%, no more than 96%, no more than 97%, no more than 98%, no more than 99% or no more than 100%.

In other aspects of this embodiment, a pharmaceutical composition disclosed herein reduces a symptom of a disorder associated with a retinopathy by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Figure 1B:
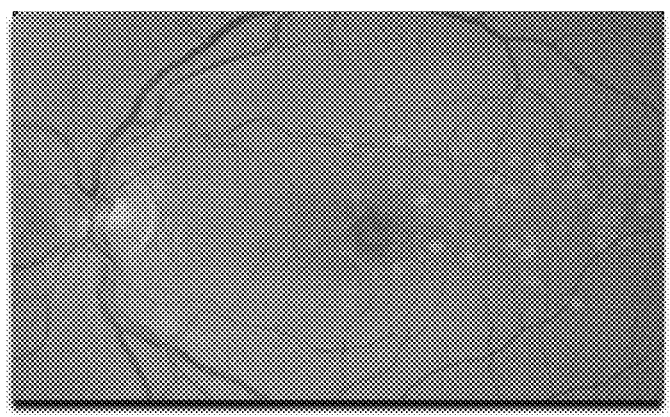
Figure 1C:
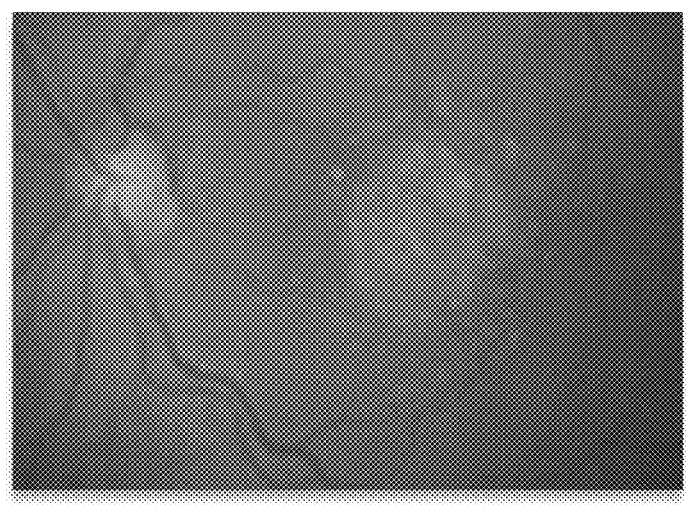

FIG. 1 provides pictures comparing a retina from a young human to that taken from an older human. FIG. 1A shows a picture of a healthy young retina. A young human healthy retina contains a high level of antioxidants. It also replaces dead or dying cells in a timely manner. A healthy young retina does not contain drusen and is able to repair DNA damage. FIG. 1B shows a picture of an older retina, which contains low levels of antioxidants and is minimally capable of replacing injured cells. Older retina's also have a reduced ability to clear drusen. In this image, there is moderate dry macular degeneration. FIG. 1C shows an older human retina wherein the patient is suffering from advanced atrophic macular degeneration, or geographic atrophy. The macular degeneration results in inflammation and retinal death, which is seen in the large "hole" in the retina near the center of the picture in FIG. 1C.

Figure 2A:
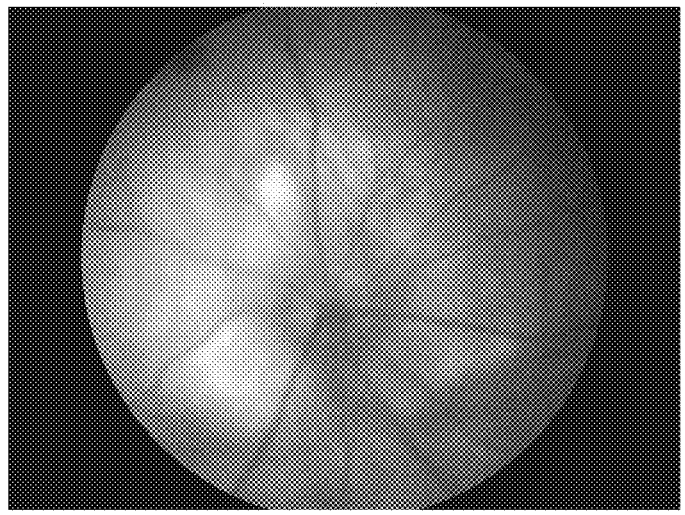
FIGS. 2A-2C show a picture of a normal retinal structure (FIG. 2A), an image of normal retinal structure on OCT (Optical Coherence Tomography) retinal imaging (FIG. 2B) and a stained cross-section showing a normal retinal structure (FIG. 2C); each showing a retinal structure with no toxicity and histopathology.
Figure 2B:
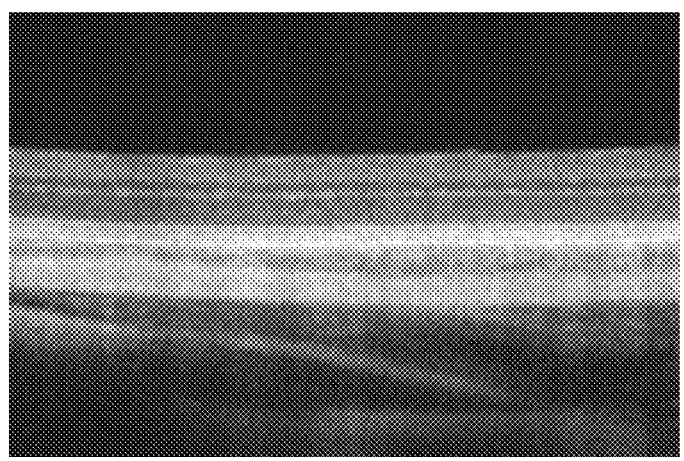
Figure 2C:
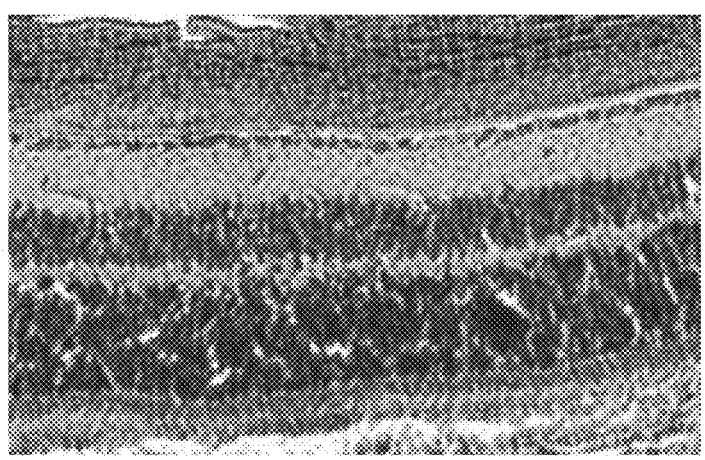

FIG. 2A demonstrates a normal retinal structure as seen through an image taken of a mouse eye treated with AAV5.BMI1. FIGS. 2B and 2C demonstrate the normal histopathology after treatment with our therapy, that is identical to a normal mouse eye. As can be seen in FIG. 2C, the cellular structure is consistent and fluid across the whole picture with no noticeable cellular damage or holes in the retina.

EXAMPLES

The following non-limiting examples are provided for illustrative purposes only in order to facilitate a more complete understanding of representative embodiments now contemplated. These examples are intended to be a mere subset of all possible contexts in which the components of the formulation may be combined. Thus, these examples should not be construed to limit any of the embodiments described in the present specification, including those pertaining to the type and amounts of components of the formulation and/or methods and uses thereof.

Example 1

Method of Treatment of Retinal Degeneration using AAV.

In retinal gene therapy, AAV is capable of "transducing" RPE cells by entering the cells and expressing the therapeutic DNA sequence. Because the cells of the retina are non-dividing, AAV can continue to persist and provide expression of the therapeutic DNA sequence over a long time period that can last several years.

According to one embodiment, the target cells are transformed or otherwise genetically modified in vivo. The cells from the patient are transformed (i.e., transduced) in vivo with a vector containing exogenous genetic material for expressing a heterologous (e.g., recombinant) gene encoding a therapeutic agent and the therapeutic agent is delivered in situ.

AAV is capable of transducing multiple cell types within the retina, including RPE cells. AAV serotype 8 can be administered in one of two routes: intravitreal or subretinal. Using the intravitreal route, AAV is injected in the vitreous humour of the eye. Using the subretinal route, AAV is injected underneath the retina, taking advantage of the potential space between the photoreceptors and RPE layer. Although this is more invasive than the intravitreal route, the fluid is absorbed by the RPE and photoreceptors and the retina flattens in approximately 14 days without significant complications. Subretinal AAV is preferred because the therapy is less likely to trigger an immune reaction. Other serotypes (e.g. 1, 2, 5, 7, 8, and 9) may also be used to transduce RPE cells.

In this example, a patient presents signs and/or symptoms of Age-Related Macular Degeneration (AMD). For example, the patient may experience gradual loss of ability to see objects clearly, shapes of objects that appear distorted and/or loss of clear color vision.

AAV-mediated gene therapy is used to target the affected retinal pigment epithelium (RPE) cells, photoreceptors, other inner and outer retinal cells, and ganglion cells. An AAV virion can is introduced by intravitreal injection into the eye(s) of the patient. Thereafter, the expression of BMI1 protein in the RPE cells is monitored. The patient's vision is also monitored. One or more subsequent injections can follow the initial injection.

For example, a therapeutically effective amount of a pharmaceutical composition disclosed herein generally is in the range of about $1 \times 10^8$, about $2 \times 10^8$, about $3 \times 10^8$, about $4 \times 10^8$, about $5 \times 10^8$, about $6 \times 10^8$, about $7 \times 10^8$, about $8 \times 10^8$, about $9 \times 10^8$, about $10 \times 10^8$, about $1 \times 10^9$, about $2 \times 10^9$, about, $4 \times 10^9$, about $5 \times 10^9$, about $6 \times 10^9$, about $7 \times 10^9$, about $8 \times 10^9$, about $9 \times 10^9$, about $10 \times 10^9$, about $1 \times 10^{10}$, about $2 \times 10^{10}$, about $3 \times 10^{10}$, about $4 \times 10^{10}$, about $5 \times 10^{10}$, about $6 \times 10^{10}$, about $7 \times 10^{10}$, about $8 \times 10^{10}$, about $9 \times 10^{10}$, 1 about $10 \times 10^{10}$, about $1 \times 10^{11}$, about $2 \times 10^{11}$, about $3 \times 10^{11}$, about $4 \times 10^{11}$, about $5 \times 10^{11}$, about $6 \times 10^{11}$, about $7 \times 10^{11}$, about $8 \times 10^{11}$, about $9 \times 10^{11}$, about $10 \times 10^{11}$, about $1 \times 10^{12}$, about $2 \times 10^{12}$, about $3 \times 10^{12}$, about $4 \times 10^{12}$, about $5 \times 10^{12}$, about $6 \times 10^{12}$, about $7 \times 10^{12}$, about $8 \times 10^{12}$, about $9 \times 10^{12}$, about $10 \times 10^{12}$, about $1 \times 10^{13}$, about $2 \times 10^{13}$, about $3 \times 10^{13}$, about $4 \times 10^{13}$, about $5 \times 10^{13}$, about, $7 \times 10^{13}$, about $8 \times 10^{13}$, about $9 \times 10^{13}$, about $10 \times 10^{13}$, about $1 \times 10^{14}$, about $2 \times 10^{14}$, about $3 \times 10^{14}$, about $4 \times 10^{14}$, about $5 \times 10^{14}$, about $6 \times 10^{14}$, about $7 \times 10^{14}$, about $8 \times 10^{14}$, about $9 \times 10^{14}$ or about $10 \times 10^{14}$ AAV virions per dose.

For example, a therapeutically effective amount of a pharmaceutical composition disclosed herein generally is in the range of about $1\times10^8$, about $2\times10^8$, about $3\times10^8$, about $4\times10^8$, about $5\times10^8$, about $6\times10^8$, about $7\times10^8$, about $8\times10^8$, about $9\times10^8$, about $10\times10^8$, about $1\times10^9$, about $2\times10^9$, about, $4\times10^9$, about $5\times10^9$, about $6\times10^9$, about $7\times10^9$, about $8\times10^9$, about $9\times10^9$, about $10\times10^9$, about $1\times10^{10}$, about $2\times10^{10}$, about $3\times10^{10}$, about $4\times10^{10}$, about $5\times10^{10}$, about $6\times10^{10}$, about $7\times10^{10}$, about $8\times10^{10}$, about $9\times10^{10}$, 1 about $10\times10^{10}$, about $1\times10^{11}$, about $2\times10^{11}$, about $3\times10^{11}$, about $4\times10^{11}$, about $5\times10^{11}$, about $6\times10^{11}$, about $7\times10^{11}$, about $8\times10^{11}$, about $9\times10^{11}$, about $10\times10^{11}$, about $1\times10^{12}$, about $2\times10^{12}$, about $3\times10^{12}$, about $4\times10^{12}$, about $5\times10^{12}$, about $6\times10^{12}$, about $7\times10^{12}$, about $8\times10^{12}$, about $9\times10^{12}$, about $10\times10^{12}$, about $1\times10^{13}$, about $2\times10^{13}$, about $3\times10^{13}$, about $4\times10^{13}$, about $5\times10^{13}$, about, $7\times10^{13}$, about $8\times10^{13}$, about $9\times10^{13}$, about $10\times10^{13}$, about $1\times10^{14}$, about $2\times10^{14}$, about $3\times10^{14}$, about $4\times10^{14}$, about $5\times10^{14}$, about $6\times10^{14}$, about $7\times10^{14}$, about $8\times10^{14}$, about $9\times10^{14}$ or about $10\times10^{14}$ AAV vg/eye.

For example, a therapeutically effective amount of a pharmaceutical composition disclosed herein generally is in the range of at least $1\times10^8$, at least $2\times10^8$, at least $3\times10^8$, at least $4\times10^8$, at least $5\times10^8$, at least $6\times10^8$, at least $7\times10^8$, at least $8\times10^8$, at least $9\times10^8$, at least $10\times10^8$, at least $1\times10^9$, at least $2\times10^9$, about, $4\times10^9$, at least $5\times10^9$, at least $6\times10^9$, at least $7\times10^9$, at least $8\times10^9$, at least $9\times10^9$, at least $10\times10^9$, at least $1\times10^{10}$, at least $2\times10^{10}$, at least $3\times10^{10}$, at least $4\times10^{10}$, at least $5\times10^{10}$, at least $6\times10^{10}$, at least $7\times10^{10}$, at least $8\times10^{10}$, at least $9\times10^{10}$, 1 at least $10\times10^{10}$, at least $1\times10^{11}$, at least $2\times10^{11}$, at least $3\times10^{11}$, at least $4\times10^{11}$, at least $5\times10^{11}$, at least $6\times10^{11}$, at least $7\times10^{11}$, at least $8\times10^{11}$, at least $9\times10^{11}$, at least $10\times10^{11}$, at least $1\times10^{12}$, at least $2\times10^{12}$, at least $3\times10^{12}$, at least $4\times10^{12}$, at least $5\times10^{12}$, at least $6\times10^{12}$, at least $7\times10^{12}$, at least $8\times10^{12}$, at least $9\times10^{12}$, at least $10\times10^{12}$, at least $1\times10^{13}$, at least $2\times10^{13}$, at least $3\times10^{13}$, at least $4\times10^{13}$, at least $5\times10^{13}$, about, $7\times10^{13}$, at least $8\times10^{13}$, at least $9\times10^{13}$, at least $10\times10^{13}$, at least $1\times10^{14}$, at least $2\times10^{14}$, at least $3\times10^{14}$, at least $4\times10^{14}$, at least $5\times10^{14}$, at least $6\times10^{14}$, at least $7\times10^{14}$, at least $8\times10^{14}$, at least $9\times10^{14}$ or at least $10\times10^{14}$ AAV virions per dose.

For example, a therapeutically effective amount of a pharmaceutical composition disclosed herein generally is in the range of at least $1\times10^8$, at least $2\times10^8$, at least $3\times10^8$, at least $4\times10^8$, at least $5\times10^8$, at least $6\times10^8$, at least $7\times10^8$, at least $8\times10^8$, at least $9\times10^8$, at least $10\times10^8$, at least $1\times10^9$, at least $2\times10^9$, about, $4\times10^9$, at least $5\times10^9$, at least $6\times10^9$, at least $7\times10^9$, at least $8\times10^9$, at least $9\times10^9$, at least $10\times10^9$, at least $1\times10^{10}$, at least $2\times10^{10}$, at least $3\times10^{10}$, at least $4\times10^{10}$, at least $5\times10^{10}$, at least $6\times10^{10}$, at least $7\times10^{10}$, at least $8\times10^{10}$, at least $9\times10^{10}$, 1 at least $10\times10^{10}$, at least $1\times10^{11}$, at least $2\times10^{11}$, at least $3\times10^{11}$, at least $4\times10^{11}$, at least $5\times10^{11}$, at least $6\times10^{11}$, at least $7\times10^{11}$, at least $8\times10^{11}$, at least $9\times10^{11}$, at least $10\times10^{11}$, at least $1\times10^{12}$, at least $2\times10^{12}$, at least $3\times10^{12}$, at least $4\times10^{12}$, at least $5\times10^{12}$, at least $6\times10^{12}$, at least $7\times10^{12}$, at least $8\times10^{12}$, at least $9\times10^{12}$, at least $10\times10^{12}$, at least $1\times10^{13}$, at least $2\times10^{13}$, at least $3\times10^{13}$, at least $4\times10^{13}$, at least $5\times10^{13}$, about, $7\times10^{13}$, at least $8\times10^{13}$, at least $9\times10^{13}$, at least $10\times10^{13}$, at least $1\times10^{14}$, at least $2\times10^{14}$, at least $3\times10^{14}$, at least $4\times10^{14}$, at least $5\times10^{14}$, at least $6\times10^{14}$, at least $7\times10^{14}$, at least $8\times10^{14}$, at least $9\times10^{14}$ or at least $10\times10^{14}$ AAV vg/eye.

For example, a therapeutically effective amount of a pharmaceutical composition disclosed herein generally is in the range of no more than $1\times10^8$, no more than $2\times10^8$, no more than $3\times10^8$, no more than $4\times10^8$, no more than $5\times10^8$, no more than $6\times10^8$, no more than $7\times10^8$, no more than $8\times10^8$, no more than $9\times10^8$, no more than $10\times10^8$, no more than $1\times10^9$, no more than $2\times10^9$, about, $4\times10^9$, no more than $5\times10^9$, no more than $6\times10^9$, no more than $7\times10^9$, no more than $8\times10^9$, no more than $9\times10^9$, no more than $10\times10^9$, no more than $1\times10^{10}$, no more than $2\times10^{10}$, no more than $3\times10^{10}$, no more than $4\times10^{10}$, no more than $5\times10^{10}$, no more than $6\times10^{10}$, no more than $7\times10^{10}$, no more than $8\times10^{10}$, no more than $9\times10^{10}$, 1 no more than $10\times10^{10}$, no more than $1\times10^{11}$, no more than $2\times10^{11}$, no more than $3\times10^{11}$, no more than $4\times10^{11}$, no more than $5\times10^{11}$, no more than $6\times10^{11}$, no more than $7\times10^{11}$, no more than $8\times10^{11}$, no more than $9\times10^{11}$, no more than $10\times10^{11}$, no more than $1\times10^{12}$, no more than $2\times10^{12}$, no more than $3\times10^{12}$, no more than $4\times10^{12}$, no more than $5\times10^{12}$, no more than $6\times10^{12}$, no more than $7\times10^{12}$, no more than $8\times10^{12}$, no more than $9\times10^{12}$, no more than $10\times10^{12}$, no more than $1\times10^{13}$, no more than $2\times10^{13}$, no more than $3\times10^{13}$, no more than $4\times10^{13}$, no more than $5\times10^{13}$, about, $7\times10^{13}$, no more than $8\times10^{13}$, no more than $9\times10^{13}$, no more than $10\times10^{13}$, no more than $1\times10^{14}$, no more than $2\times10^{14}$, no more than $3\times10^{14}$, no more than $4\times10^{14}$, no more than $5\times10^{14}$, no more than $6\times10^{14}$, no more than $7\times10^{14}$, no more than $8\times10^{14}$, no more than $9\times10^{14}$ or no more than $10\times10^{14}$ AAV virions per dose.

For example, a therapeutically effective amount of a pharmaceutical composition disclosed herein generally is in the range of no more than $1\times10^8$, no more than $2\times10^8$, no more than $3\times10^8$, no more than $4\times10^8$, no more than $5\times10^8$, no more than $6\times10^8$, no more than $7\times10^8$, no more than $8\times10^8$, no more than $9\times10^8$, no more than $10\times10^8$, no more than $1\times10^9$, no more than $2\times10^9$, about, $4\times10^9$, no more than $5\times10^9$, no more than $6\times10^9$, no more than $7\times10^9$, no more than $8\times10^9$, no more than $9\times10^9$, no more than $10\times10^9$, no more than $1\times10^{10}$, no more than $2\times10^{10}$, no more than $3\times10^{10}$, no more than $4\times10^{10}$, no more than $5\times10^{10}$, no more than $6\times10^{10}$, no more than $7\times10^{10}$, no more than $8\times10^{10}$, no more than $9\times10^{10}$, 1 no more than $10\times10^{10}$, no more than $1\times10^{11}$, no more than $2\times10^{11}$, no more than $3\times10^{11}$, no more than $4\times10^{11}$, no more than $5\times10^{11}$, no more than $6\times10^{11}$, no more than $7\times10^{11}$, no more than $8\times10^{11}$, no more than $9\times10^{11}$, no more than $10\times10^{11}$, no more than $1\times10^{12}$, no more than $2\times10^{12}$, no more than $3\times10^{12}$, no more than $4\times10^{12}$, no more than $5\times10^{12}$, no more than $6\times10^{12}$, no more than $7\times10^{12}$, no more than $8\times10^{12}$, no more than $9\times10^{12}$, no more than $10\times10^{12}$, no more than $1\times10^{13}$, no more than $2\times10^{13}$, no more than $3\times10^{13}$, no more than $4\times10^{13}$, no more than $5\times10^{13}$, about, $7\times10^{13}$, no more than $8\times10^{13}$, no more than $9\times10^{13}$, no more than $10\times10^{13}$, no more than $1\times10^{14}$, no more than $2\times10^{14}$, no more than $3\times10^{14}$, no more than $4\times10^{14}$, no more than $5\times10^{14}$, no more than $6\times10^{14}$, no more than $7\times10^{14}$, no more than $8\times10^{14}$, no more than $9\times10^{14}$ or no more than $10\times10^{14}$ AAV vg/eye.

For the gene therapy methods, a person having ordinary skill in the art of molecular biology and gene therapy would be able to determine, without undue experimentation, the appropriate dosages, and routes of administration of the expression vector used in the novel methods of the disclosure.

Example 2

Method of Treatment of Retinal Dystrophy Using AAV.

In this example, a patient presents signs and/or symptoms of Retinal Dystrophy. For example, Retinitis pigmentosa, the most common retinal dystrophy, is an example of such a genetic ailment. The patient may experience symptoms such as difficulty seeing at night and a loss of peripheral vision.

As described above, AAV-mediated gene therapy is used to target the affected retinal pigment epithelium (RPE) cells. An AAV virion is introduced by intravitreal injection into the eye(s) of the patient. Thereafter, the expression of BMI1 protein in the RPE cells is monitored. The patient's vision is also monitored. One or more subsequent injections can follow the initial injection.

Example 3

Method of Treatment of Macular Degeneration Using AAV.

In this example, a patient presents signs and/or symptoms of Macular Degeneration. A patient who experiences age-related macular degeneration may have blind spots in the center of vision. As it gets worse, central vision can be lost.

As described above, AAV-mediated gene therapy is used to target the affected retinal pigment epithelium (RPE) cells. An AAV virion can is introduced by intravitreal, subretinal and/or suprachoroidal injection into the eye(s) of the patient. Thereafter, the expression of BMI1 protein in the RPE cells is monitored. The patient's vision is also monitored. One or more subsequent injections can follow the initial injection.

Example 4

Method of Treatment of Macular Dystrophy Using AAV.

In this example, a patient presents signs and/or symptoms of Macular Dystrophy. A patient who experiences vitelliform macular dystrophy may experience progressive vision loss. The condition causes a fatty yellow pigment (lipofuscin) to build up in cells underlying the macula. Over time, the abnormal accumulation of this substance can damage cells that are critical for clear central vision. As a result, the patient can lose central vision, and their eyesight may become blurry or distorted.

As described above, AAV-mediated gene therapy is used to target the affected retinal pigment epithelium (RPE) cells. An AAV virion can is introduced by intravitreal injection into the eye(s) of the patient. Thereafter, the expression of BMI1 protein in the RPE cells is monitored. The patient's vision is also monitored. One or more subsequent injections can follow the initial injection.

Example 5

Evaluating Cellular Senescence in Wild-Type Versus BMI1 Overexpressed Cells In Vitro In this example, an RPE cell line, such as ARPE-19 or an IPS derived RPE cell line, is cultured in vitro and used to distinguish the difference in cellular senescence between RPE cells where a BMI1/AAV virion is introduced to the cell such that the RPE cell over expresses BMI1 versus RPE cells that are not introduced to a BMI1/AAV virion. Following introduction of the virion, it is found that the RPE cells treated with the BMI/AAV virion express BM/1 at levels that exceed those of untreated RPE cells. It is also found that the increased production of BM/1 results in a loss of senescence as compared to RPE cells that did not have the BM/1/AAV virion introduced into the RPE cell. As senescence is associated with retinal cell death, a loss of senescence would be associated with reduced retinal cell death and a reduction in macular degeneration.

Example 6

Evaluating Cellular Death in Wild-Type Versus BMI1 Overexpressed Cells In Vitro

In this example, an RPE cell line, such as ARPE-19 or an IPS derived RPE cell line, is cultured in vitro and used to distinguish the difference in the rate of cellular death between RPE cells where a BMI1/AAV virion is introduced to the cell such that the RPE cell over expresses BMI versus RPE cells that are not introduced to a BMI1/AAV virion. Following introduction of the virion, it is found that the RPE cells treated with the BMI/AAV virion express BMI1 at levels that exceed those of untreated RPE cells. It is also found that the increased production of BMI1 results in a reduction in cellular death when compared to RPE cells that did not have the BMI1/AAV virion introduced into the RPE cell. As a reduction in cellular death is associated with a reduction in the instance of macular degeneration and the loss of retinal function. Further, it is determined that the cells into which the BM/1/AAV virion is introduced proliferate at a greater rate than those cells that do not have the virion introduced.

Example 7

Evaluating Cellular Recovery from Oxidative Stress Death in Wild-Type Versus BMI1 Overexpressed Cells In Vitro In this example, an RPE cell line, such as ARPE-19 or an IPS derived RPE cell line, is cultured in vitro and used to distinguish the difference in cellular recovery from cellular stress, including oxidative stress, which leads to an increase in the rate of apoptosis. Cellular stress is induced in one experiment where a BMI1/AAV virion is introduced to the cell such that the RPE cell over expresses BMI1 versus RPE cells that are not introduced to a BMI1/AAV virion. Cellular stress is induced by the introduction of lactate into the medium in which the cells are grown. We measured the rate of cellular death between RPE cells where a BMI1/AAV virion is introduced to the cell such that the RPE cell over expresses BMI1 versus RPE cells that are not introduced to a BMI1/AAV virion. Following introduction of the lactate, it is found that the RPE cells treated with the BMI1/AAV virion that express BMI1 at levels that exceed those of untreated RPE cells recover from the oxidative stress induced by lactate quicker than those RPE cells where the virion is not introduced. It is also found that the increased production of BMI1 results in a reduction in cellular death resulting from oxidative stress when compared to RPE cells that did not have the BMI1/AAV virion introduced into the RPE cell. As a reduction in cellular death is associated with a reduction in the instance of macular degeneration and the loss of retinal function. Further, it is determined that the cells into which the BM/1/AAV virion is introduced proliferate at a greater rate than those cells that do not have the virion introduced. It is understood that stress can be induced by other means other than the introduction of lactate into the cellular medium.

Example 8

Evaluating macular degeneration in a murine animal model following the introduction of a BMI1/AAV virion that results in an increase in BMI1 expression.

In this example, a mouse model for macular degeneration is used. A BMI1/AAV virion is introduced subretinally into the mouse eye. Over time, the mice are evaluated for retinal degeneration. The eyes of the mice are examined to determine whether the photoreceptors and outer nuclear cells in mice where a BMI1/AAV virion was introduced are healthier and suffer less death (and hence, macular degeneration) than those same cells in a mouse where the BMI1/AAV virion is not introduced. Following examination of the eyes of the mice, it is found that the photoreceptors and outer nuclear cells of the mice where the BM/1/AAV virion is introduced into the eye were healthier and less likely to die than those where the BM/1/AAV virion is not introduced.

Example 9

Figure 3A:
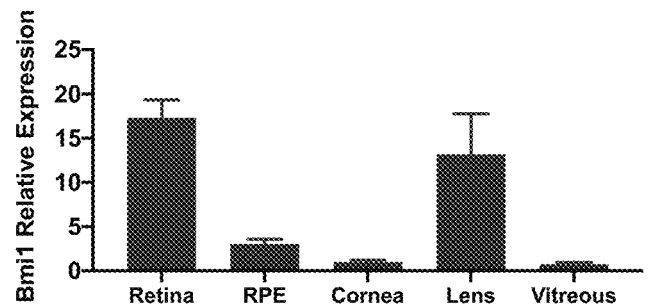
FIG. 3A shows mRNA expression in different regions of the human eye from donor eye tissues.
Figure 3B:
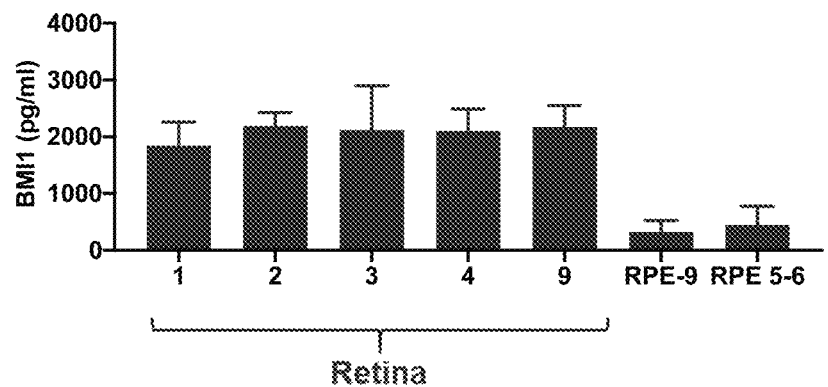
FIG. 3B shows protein expression in particular regions of the retina and RPE-choroid layers of the donor human eye.

In this example BMI1 mRNA and protein expression were measured in different portions of the eye. As found in FIG. 3A, BMI1 mRNA expression is found principally in the retina and lens and less so in the RPE. Expression of BMI1 mRNA is lowest in the cornea and vitreous solution. In FIG. 3B, the location of BMI1 retinal expression was found to be relatively evenly expressed throughout the retina as denoted by the different retinal regions identified in FIG. 3C. A similar result is shown for the RPE in FIG. 3B based on the results from the samples taken at the center, middle and periphery of the eye.

Figure 3C:
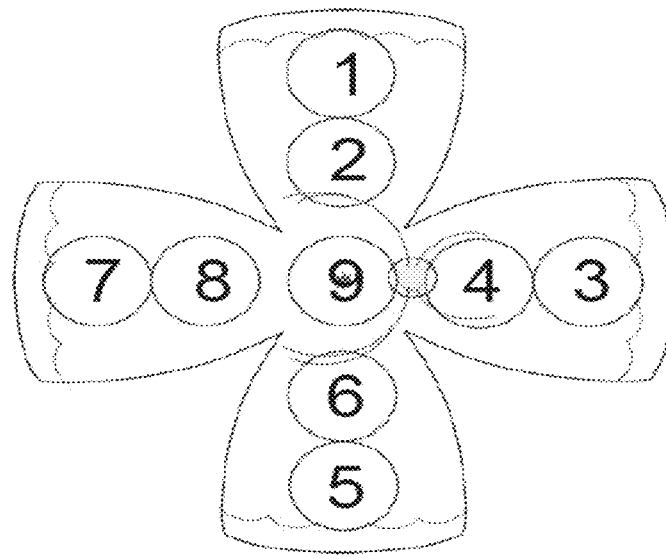
FIG. 3C shows the different regions of the eye, with each region identified by a particular number.

FIG. 3C provides a schematic of the eye denoting the different regions by a numerical representation. In FIG. 3C the region denoted by the number 9 constitutes the macula. Numbers 2, 4, 6, and 8 represent the mid-periphery of the retina. Numbers 1, 3, 5 and 7 constitute the far periphery of the retina. For purposes of this Example 9, samples to determine relative expression in FIG. 3B were taken from the region of the eye set forth in FIG. 3C.

Example 10; Biodistribution of BMI1 in Human Eyes

Background: The following describes the determination of the amount of BMI1 protein in the human eye. It also describes the determination of the BMI1 gene expression level in the eye. In both cases, the amount of protein and gene expression level of BMI1 was determined based on their ocular biodistribution.

Methodology: Human donor eyes were obtained from One Legacy Foundation. The human donor eyes (average age 64 years old) were maintained in optimal conditions until receipt. Upon arrival the eyes were dissected and separated into different tissue fractions comprising the cornea, lens, vitreous, Iris, retina, and RPE-choroid layer. Each of the different tissue fractions were flash frozen in liquid nitrogen and then were processed for RNA and protein extraction. Total mRNA was extracted from tissues using Trizol (Thermo Fisher Scientific) according to the manufacturer's instructions. The quantity and quality of the mRNA was determined using a NanoDrop spectrophotometer (NanoDrop Technologies). First-strand cDNA synthesis was performed by a reaction of 1.0 µg of total mRNA with a random primer, using the Maxima Reverse Transcriptase Kit (Thermo Fisher Scientific). Conventional RT-PCR (qRT-PCR) was performed using the TaqMan Fast Advanced Master Mix (Thermo Fisher Scientific). qPCR was performed on a total of 20 µl of mixture solution in 96-well plates using the QuantStudio 6 Pro system (Thermo Fisher Scientific). Each 20 µl of reaction mixture contained 10 µl of SYBR Green Master (Thermo Fisher Scientific), 0.5 µM primers, and diluted cDNA. Real-time PCR quantifications were run in triplicate for each sample, the average was determined, and PCR products were quantified using the QuantStudio 6 Pro software. Expression levels were normalized to GAPDH levels. Gene-fold changes of BMI1 were normalized to the Cornea gene expression. The sequence of the primers used are listed in Table 1.

TABLE 1

List of primers forward (F) and reverse (R) used for qPCR analysis for human (h), pig (sc) and mouse (m).

| Primer | Sequence (5'→3') |
|---|---|
| qh.Bax-F | CATATAACCCCGTCAACGCAG |
| qh.Bax-R | GCAGCCGCCACAAACATAC |
| qh.BcI2-F | ATCGCCCTGTGGATGACTGAGT |
| qh.BcI2-R | GCCAGGAGAAATCAAACAGAGGC |
| qh.Gapdh-F | AGGTCGGTGAACGGATTTG |
| qh.Gapdh-R | TGTAGACCATGTAGTTGAGGTCA |
| qh.Gpx1-F | CAATCAGTTCGGACACCAGGAG |
| qh.Gpx1-R | TCTCACCATTCACTTCGCACTTC |
| qh.Gpx3-F | CTTCTTCTTGTTGAGCTGGACTC |
| qh.Gpx3-R | CTGTGGAGGTCACTGTAGACT |
| qh.BMI1-F | GGTACTTCATTGATGCCACAACC |
| qh.BMI1-R | CTGGTCTTGTGAACTTGGACATC |
| qh.p21-F | AGTATGCCGTCGTCTGTTCG |
| qh.p21-R | GACTGCAAGACAGCGACAAG |
| qh.p53-F | GGTTCCTGCCCCAGGATGTTG |
| qh.p53-R | GGAACATCTCGAAGCGCTCA |
| qh.Sod1-F | CTCACTCTCAGGAGACCATTGC |
| qh.Sod1-R | CCACAAGCCAAACGACTTCCAG |
| qh.Sod2-F | CTGGACAAACCTCAGCCCTAAC |
| qh.Sod2-R | AACCTGAGCCTTGGACACCAAC |
| qh.Vegfa-F | AGATCGAGTACATCTTCAAGCCATC |
| qh.Vegfa-R | CGTCATTGCAGCAGCCC |
| qm.Gapdh-F | GGGTGTGAACCACGAGAAATATG |
| qm.Gapdh-R | GCAGTGATGGCATGGACTGT |
| qm.Gpx1-F | AGTCCACCGTGTATGCCTTCT |
| qm.Gpx1-R | GAGACGCGACATTCTCAATGA |
| qm.BMI1-F | AAATCCCCACTTAATGTGTGTCC |
| qm.BMI1-R | CTTGCTGGTCTCCAAGTAACG |
| qm.p16-F | TGTTGAGGCTAGAGAGGATCTTG |
| qm.p16-R | CGAATCTGCACCGTAGTTGAGC |
| qm.p21-F | TCGCTGTCTTGCACTCTGGTGT |
| qm.p21-R | CCAATCTGCGCTTGGAGTGATAG |
| qm.p53-F | CTGGTTAGTCCTGAGACAGAGG |
| qm.p53-R | AGATGCAGCCAAACACAGGCAC |

TABLE 1-continued

List of primers forward (F) and reverse (R) used for qPCR analysis for human (h), pig (sc) and mouse (m).

| Primer | Sequence (5'→3') |
|---|---|
| qm.Sod1-F | GGTGAACCAGTTGTGTTGTCAGG |
| qm.Sod1-R | ATGAGGTCCTGCACTGGTACAG |
| qm.Sod2-F | CAGACCTGCCTTACGACTATGG |
| qm.Sod2-R | CTCGGTGGCGTTGAGATTGTT |
| qm.Vegfa-F | CTGCCGTCCGATTGAGACC |
| qm.Vegfa-R | CCCCTCCTTGTACCACTGTC |
| qsc.Bmi1-F | CGTGTATTGTGCGTTACCTGGA |
| qsc.Bmi1-R | TTCAGTAGTGGTCTGGTTTTGT |

Eye samples were analysed to determine the level of BMI1 protein using a standard indirect Enzyme-Linked Immunosorbent Assay (ELISA). A protein extract was prepared in a RIPA Lysis and Extraction Buffer (Thermo Fisher Scientific) supplemented with the Halt™ Phosphatase Inhibitor and the Halt™ Protease inhibitor cocktail (Thermo Fisher Scientific). Protein concentration was measured using the Micro BCA™ Protein Assay Kit (Thermo Fisher Scientific). This was done by first loading triplicate samples of a 2 ug/ml of protein extract into a 96 well plate. Human recombinant BMI1 (Origene) was used as a control and to prepare a standard curve for protein level. A polyclonal anti-BMI1 antibody (Bethyl Laboratories) was used as the first antibody in the ELISA. The actual detection reaction was performed using the ELISA Buffer Kit (Thermo Fisher Scientific) following the manufacturer's instructions.

Figure 4A:
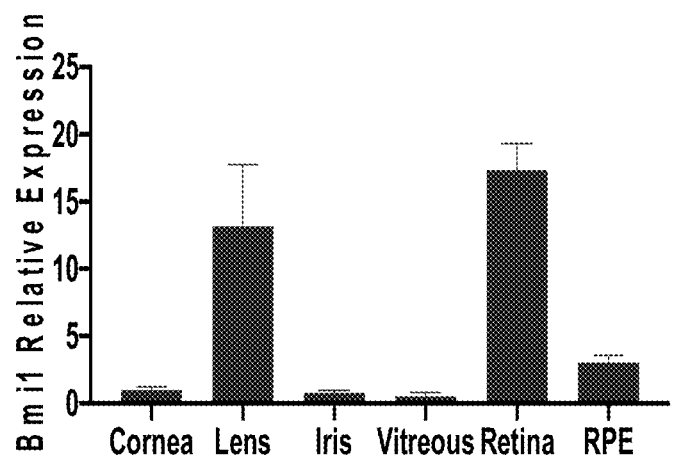
FIG. 4A shows the mRNA expression from the cornea, lens, iris, vitreous, retina and RPE-choroid of human donors' eyes based on qRT-PCR that was performed for the human BMI1 gene, wherein the human GAPDH gene expression was used as a control. Values are expressed as mean±SD. Values are normalized to the cornea expression of BMI1 in human eyes.
Figure 4B:
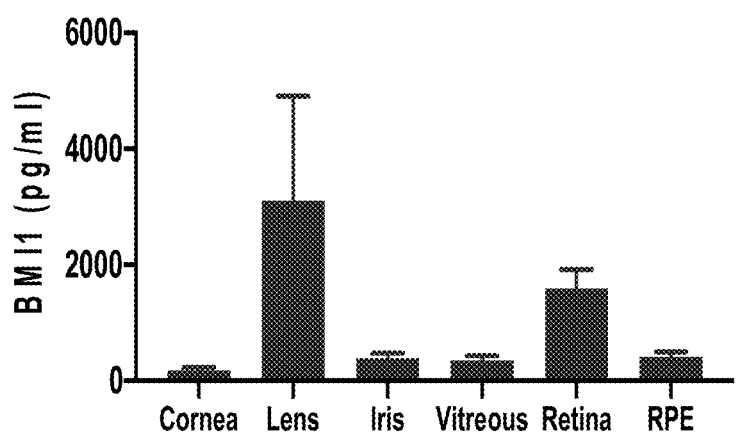
FIG. 4B shows the protein expression using an indirect ELISA for protein extracted from the cornea, lens, iris, vitreous, retina and RPE of human donors' eyes. The ELISA was performed using a commercial anti rabbit antibody against BMI1. Human recombinant BMI1 was using for the standard curve. Values are expressed as mean±SD.

Results: FIG. 4A shows the results from the determination of mRNA levels of the BMI1 gene in the human eye. What is seen is that the BMI1 gene expression is found principally detected in the lens and the retina. As shown in FIG. 4B, the mRNA levels correlate with the location of the highest expression of the BMI1 protein.

Example 11: Biodistribution of BMI1 in Pig Eyes

Background: The following describes the determination of the dose of the BMI1 protein, the level of gene expression, and ocular biodistribution of our investigational young pig eyes.

Methodology: Young pig eyes were obtained from Fist Visiontech, Inc. The pig eye specimens were maintained to ensure optimal recovery of biomaterials following receipt of the pig eyes by our facility. Upon arrival, the eyes were dissected to obtain cornea, lens, vitreous, Iris, retina, and RPE-choroid layer. The tissues were flash frozen in liquid nitrogen and then were processed for RNA and protein extraction.

Total mRNA was extracted from tissues using Trizol (Thermo Fisher Scientific) according to the manufacturer's instructions. The quantity and quality of the mRNA was determined using a NanoDrop spectrophotometer (Nano-Drop Technologies). First-strand cDNA synthesis was performed by a reaction of 1.0 µg of total mRNA with a random primer, using the Maxima Reverse Transcriptase Kit (Thermo Fisher Scientific). Conventional RT-PCR (qRT-PCR) was performed using the TaqMan Fast Advanced Master Mix (Thermo Fisher Scientific). qPCR was performed on a total of 20 µl of mixture solution in 96-well plates using the QuantStudio 6 Pro system (Thermo Fisher Scientific). Each 20 µl of reaction mixture contained 10 µl of SYBR Green Master (Thermo Fisher Scientific), 0.5 µM primers, and diluted cDNA. Real-time PCR quantifications were run in triplicate for each sample, the average was determined, and PCR products were quantified using the QuantStudio 6 Pro software. Expression levels were normalized to GAPDH levels. Gene-fold changes of BMI1 were normalized to the Cornea gene expression. The sequence of the primers used for are listed in Table 1. BMI1 mRNA quantification was performed as described.

For Western Blot analysis of BMI1 samples were analysed for the expression levels of BMI1 and β-Actin by standard immunoblot techniques. Briefly, cell extract aliquots were subjected to SDS gel electrophoresis in 4%-12% polyacrylamide gels, electrophoretically transferred onto nitrocellulose membrane using iBLOT system (Thermo Fisher Scientific) and probed with rabbit anti-BMI1 (1:1,000; Bethyl Laboratories) or mouse anti-β-Actin (1:5,000; R&D Systems) antibodies. Anti-rabbit and anti-mouse horseradish peroxidase (Thermo Fisher Scientific) was used for detection and all immunoreactions were visualized by enhanced chemiluminescence using Super Signal West Pico Plus (Thermo Fisher Scientific). More particularly, a protein extract was prepared in a RIPA Lysis and Extraction Buffer (Thermo Fisher Scientific) supplemented with the Halt™ Phosphatase Inhibitor and the Halt™ Protease inhibitor cocktail (Thermo Fisher Scientific). Protein concentration was measured using the Micro BCA™ Protein Assay Kit (Thermo Fisher Scientific). This was done by first loading triplicate samples of a 2 ug/ml of protein extract into a 96 well plate. Human recombinant BMI1 (Origene) was used as a control and to prepare a standard curve for protein level. A polyclonal anti-BMI1 antibody (Bethyl Laboratories) was used as the first antibody in the ELISA. The actual detection reaction was performed using the ELISA Buffer Kit (Thermo Fisher Scientific) following the manufacturer's instructions.

Figure 5A:
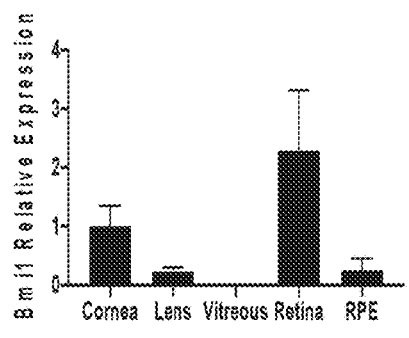
FIG. 5A shows the total mRNA that was extracted from the cornea, lens, vitreous, retina and RPE-choroid of pig eyes following qRT-PCR using primers for pig BMI1. GAPDH was used as a control gene. Values are expressed as mean±SD. Values are normalized to the cornea expression of BMI1 in pig eyes.
Figure 5B:
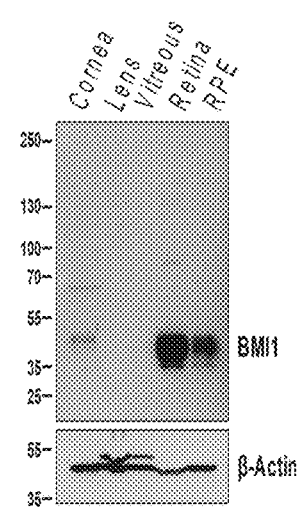
FIG. 5B shows a Western Blot analysis for BMI1 protein extracted from the cornea, lens, vitreous, retina and RPE-choroid of pig eyes. BMI1 anti-rabbit antibody was used to detect BMI1, and β-actin was used as a loading control. Numbers indicates the KDa of the standard.
Figure 5C:
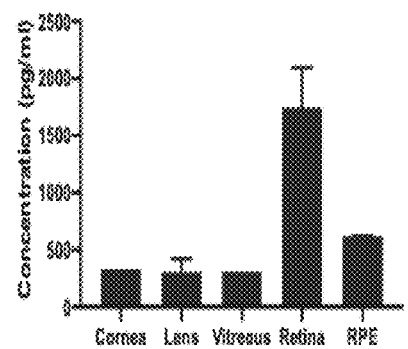
FIG. 5C shows the results of an indirect ELISA that was performed using a protein extract from the cornea, lens, iris, vitreous, retina and RPE of pig eyes. The ELISA was performed using a commercial anti-rabbit antibody against BMI1. Human recombinant BMI1 was using for the standard curve. Values are expressed as mean±SD.

Results: As shown in FIG. 5A mRNA levels of BMI1 are highly detected in the retina and to a lesser extent the cornea of young pig eyes. Similar expression patterns were found for BMI1 protein in young pig eyes. As shown the western blot (FIG. 5B), protein expression of BMI1 was pronounced in the retina and found to a lesser degree in the RPE-choroid and cornea. This is also shown based on the concentration of BMI1 in each type of tissue in the young pig eyes where the highest level of BMI1 expression was found in the retina (FIG. 5C).

Example 12: BMI1 is Downregulated in Aged Mice

Background: In this example, we evaluated whether expression of BMI1 mRNA was downregulated in an aged retina. To make this determination, we evaluated the mRNA and protein levels of BMI1 in young and old mice.

Methodology: Nine week and 90-week-old C57BL6/J mice were obtained from The Jackson Laboratory. Eyes from these mice were enucleated and the retina was dissected from the right eyes of the mice. The tissue was flash frozen in liquid nitrogen and then was processed for RNA and protein extraction.

Total mRNA was extracted from tissues using Trizol (Thermo Fisher Scientific) according to the manufacturer's instructions. The quantity and quality of the mRNA was determined using a NanoDrop spectrophotometer (Nano-Drop Technologies). First-strand cDNA synthesis was performed by a reaction of 1.0 µg of total mRNA with a random primer, using the Maxima Reverse Transcriptase Kit (Thermo Fisher Scientific). Conventional RT-PCR (qRT-PCR) was performed using the TaqMan Fast Advanced Master Mix (Thermo Fisher Scientific). qPCR was performed on a total of 20 µl of mixture solution in 96-well plates using the QuantStudio 6 Pro system (Thermo Fisher Scientific). Each 20 µl of reaction mixture contained 10 µl of SYBR Green Master (Thermo Fisher Scientific), 0.5 µM primers, and diluted cDNA. Real-time PCR quantifications were run in triplicate for each sample, the average was determined, and PCR products were quantified using the QuantStudio 6 Pro software. Expression levels were normalized to GAPDH levels. Gene-fold changes of BMI1 were normalized to the Cornea gene expression. The sequence of the primers used for are listed in Table 1.

Eyes samples were analysed to determine the level of BMI1 protein using a standard indirect Enzyme-Linked Immunosorbent Assay (ELISA). A protein extract was prepared in a RIPA Lysis and Extraction Buffer (Thermo Fisher Scientific) supplemented with the Halt™ Phosphatase Inhibitor and the Halt™ Protease inhibitor cocktail (Thermo Fisher Scientific). Protein concentration was measured using the Micro BCA™ Protein Assay Kit (Thermo Fisher Scientific). This was done by first loading triplicate samples of a 2 ug/ml of protein extract into a 96 well plate. Human recombinant BMI1 (Origene) was used as a control and to prepare a standard curve for protein level. A polyclonal anti-BMI1 antibody (Bethyl Laboratories) was used as the first antibody in the ELISA. The actual detection reaction was performed using the ELISA Buffer Kit (Thermo Fisher Scientific) following the manufacturer's instructions.

For histological analysis, the left eyes were embedded in OCT and frozen in isopentane cooled by liquid nitrogen. The tissue was sectioned on a cryostat (Leica) with section slices of 10 µm followed by Hematoxylin-Eosin (H&E) staining for morphological observation of the retinal layers. ONL and total retina thickness were measured using the Image J software.

Figure 6A:
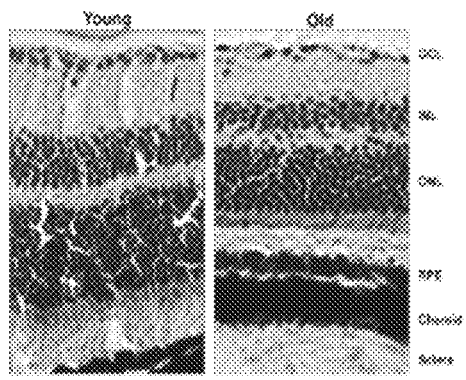
FIG. 6A shows a representative image following an H&E staining of a retina obtained from young and old C57BL6J mice. The different layers are indicated at the right of the image.
Figure 6B:
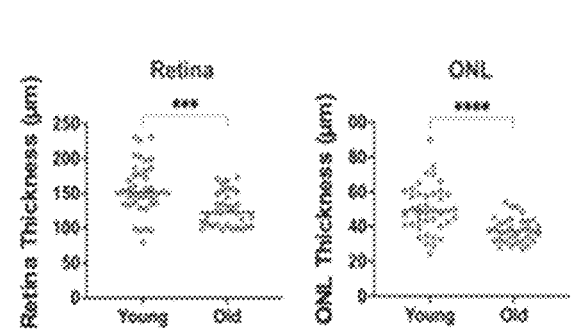
FIG. 6B shows the quantification of retina and ONL thickness from the H&E images shown in FIG. 6A. Values are expressed as mean±SD. *P value<0.001, **P value<0.0001 (One-way ANOVA).
Figure 6C:
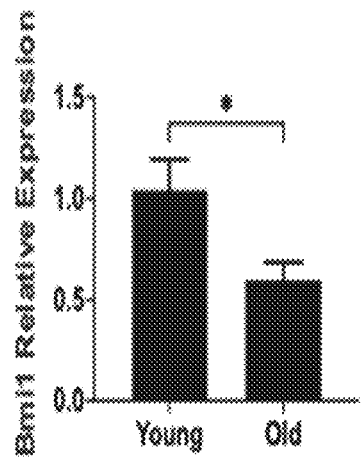
FIG. 6C shows total BMI1 mRNA that was extracted from the cornea, lens, vitreous, retina and RPE of pig eyes following qRT-PCR using primers for the pig BMI1 gene. GAPDH was used as a control gene. Values are expressed as mean±SD. Values are normalized to the cornea expression of BMI1 in human eyes. *P value<0.05 (One-way ANOVA).
Figure 6D:
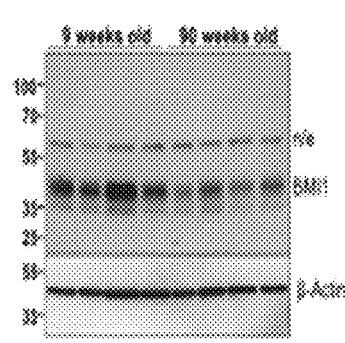
FIG. 6D shows a Western Blot analysis for protein extracted from the cornea, lens, vitreous, retina and RPE-choroid of pig eyes. BMI1 anti-rabbit antibody was using to detect BMI1 protein, and β-actin was used as a loading control. Numbers indicates the KDa of the standard.
Figure 6E:
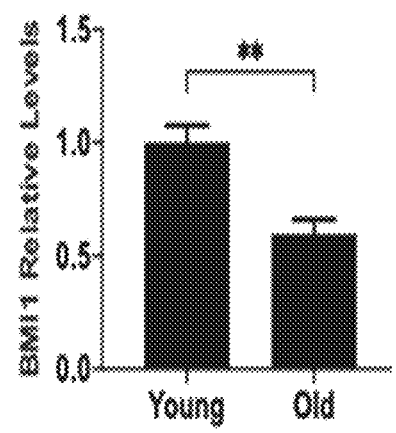
FIG. 6E shows a densitometric quantification of western blot bands form FIG. 6D, with BMI1 protein level values normalized against a β-actin control. Values represent the total retina and RPE and are expressed as mean±SD. **P value<0.01 (One-way ANOVA).

Results: As shown in FIGS. 6A and 6B, the thickness of the retina and ONL layers decrease as the mice age. As shown FIGS. 6A and 6B, the retina and ONL layers in the old mice (90 weeks old) were thinner than those found in a young mouse (9 weeks old). Analysis of BMI1 mRNA expression levels finds a similar difference, wherein young mice retina and ONL layers had a higher BMI1 mRNA level than those of older mice (FIG. 6C). Protein expression of BMI1 in the retina and ONL layers tracked with BMI1 mRNA expression levels, with greater amounts of BMI1 protein found in the retina and ONL layers of young mice when compared to the expression of BMI1 protein in the retina and ONL layers of older mice (FIG. 6D). FIG. 6E shows the quantification of the densitometry of the bands shown in FIG. 6D, wherein the values were normalized by the loading control β-Actin. As shown in FIG. 6E, BMI1 protein expression is higher in young mice when compared to older mice.

Example 13: Dosing Studies of AAV5.BMI1 in Balb/c Mice

Background: The optimal dose of AAV5.BMI1 was determined by subretinal delivery in Balb/c mice.

Methodology: 6-week-old Balb/c mice were obtained from The Jackson Laboratory. For all experiments, mice were anaesthetized using Isofluorane. Following anaesthetizing the mice, the pupils of all animals were dilated using topical 1% tropicamide and 2.5% phenylepherine. AAV5.BMI1 was injected into the subretinal space of the eye with the tip of a 10-mm 33-gauge hypodermic needle mounted on a 10 µl syringe (Hamilton). 1 µl of vector suspension was then injected subretinally at a dose rage of $1 \times 10^7$ or $5 \times 10^{10}$ vg/eye. Control animals were injected with 1 µl of Saline solution (NaCl 0.9%). All animals received chloramphenicol 1% eye ointment to the cornea. The mice were euthanized 4 weeks after the injection and eyes were enucleated and the retina was dissected in the right eyes. The tissue was flash frozen in liquid nitrogen and then was processed for mRNA and protein extraction.

Total mRNA was extracted from tissues using Trizol (Thermo Fisher Scientific) according to the manufacturer's instructions. The quantity and quality of the mRNA was determined using a NanoDrop spectrophotometer (Nano-Drop Technologies). First-strand cDNA synthesis was performed by a reaction of 1.0 µg of total mRNA with a random primer, using the Maxima Reverse Transcriptase Kit (Thermo Fisher Scientific). Conventional RT-PCR (qRT-PCR) was performed using the TaqMan Fast Advanced Master Mix (Thermo Fisher Scientific). qPCR was performed on a total of 20 µl of mixture solution in 96-well plates using the QuantStudio 6 Pro system (Thermo Fisher Scientific). Each 20 µl of reaction mixture contained 10 µl of SYBR Green Master (Thermo Fisher Scientific), 0.5 µM primers, and diluted cDNA. Real-time PCR quantifications were run in triplicate for each sample, the average was determined, and PCR products were quantified using the QuantStudio 6 Pro software. Expression levels were normalized to GAPDH levels. Gene-fold changes of BMI1 were normalized to the Cornea gene expression. The sequence of the primers used for are listed in Table 1.

Eyes samples were analysed to determine the level of BMI1 protein using a standard indirect Enzyme-Linked Immunosorbent Assay (ELISA). A protein extract was prepared in a RIPA Lysis and Extraction Buffer (Thermo Fisher Scientific) supplemented with the Halt™ Phosphatase Inhibitor and the Halt™ Protease inhibitor cocktail (Thermo Fisher Scientific). Protein concentration was measured using the Micro BCA™ Protein Assay Kit (Thermo Fisher Scientific). This was done by first loading triplicate samples of a 2 ug/ml of protein extract into a 96 well plate. Human recombinant BMI1 (Origene) was used as a control and to prepare a standard curve for protein level. A polyclonal anti-BMI1 antibody (Bethyl Laboratories) was used as the first antibody in the ELISA. The actual detection reaction was performed using the ELISA Buffer Kit (Thermo Fisher Scientific) following the manufacturer's instructions.

For histological analysis, the left eyes were embedded in OCT and frozen in isopentane cooled by liquid nitrogen. The tissue was sectioned on a cryostat (Leica) with section slices of 10 µm followed by Hematoxylin-Eosin (H&E) staining for morphological observation of the retinal layers. ONL and total retina thickness were measured using the Image J software.

Figure 7A:
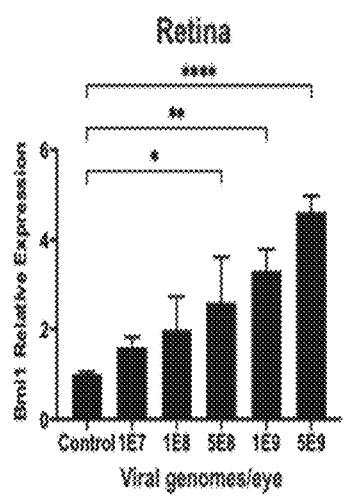
FIG. 7A shows the quantity of total mRNA that was extracted from the retina of control and AAV5.BMI1 transduced mice eyes following qRT-PCR that was performed using primers for the mouse BMI1 gene. GAPDH was used as a control gene. Values are expressed as mean±SD. Values are normalized to the control levels of BMI1 in control mice. *P value<0.5 P value<0.01, **P value<0.0001 (One-way ANOVA).
Figure 7B:
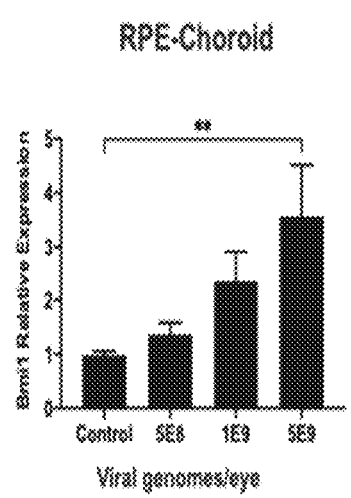
FIG. 7B shows the quantity of total mRNA that was extracted from the RPE-choroid of control and AAV5.BMI1 transduced mice eyes following qRT-PCR that was performed using primers for the mouse BMI1 gene. GAPDH was used as a control gene. Values are expressed as mean±SD. Values are normalized to the control levels of BMI1 in control mice. **P value<0.01 (One-way ANOVA).
Figure 7C:
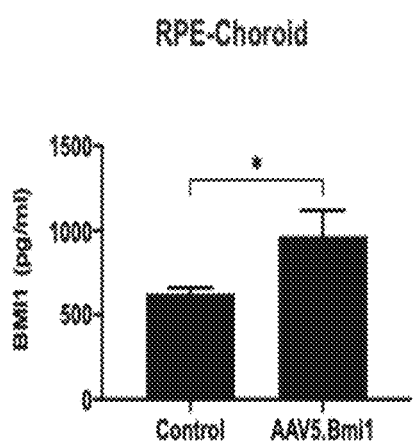
FIG. 7C shows the results from an indirect ELISA that was performed using protein extract from the RPE-Choroid of control and AAV5.BMI1 transduced mice eyes. The ELISA was performed using a commercial anti-rabbit antibody against BMI1. Human recombinant BMI1 was used for the standard curve. Values are expressed as mean±SD. *P value<0.05 (t-student).
Figure 7D:
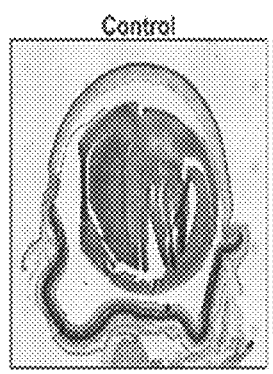
FIGS. 7D-7F show representative images following the H&E staining of an eye section obtained from a control (FIG. 7C) and AAV5.BMI1 transduced mice eyes ($1\times10^9$ (FIG. 7D) and $1\times10^{10}$ vg/eye (FIG. 7E)).
Figure 7E:
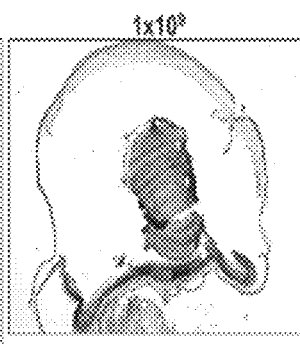
Figure 7F:

Results: As shown in FIGS. 7A (retina) and 7B (RPE-choroid), the mRNA levels of BMI1 increase with increased dosages of AAV5. More particularly, BMI1 mRNA levels increased as the dosage of AAV5.BMI1 increased from $5 \times 10^8$ to $1 \times 10^9$ and finally $5 \times 10^9$ vg/eye. mRNA levels at all dosages were greater following administration of AAV5.BMI1 than the control (FIGS. 7A and 7B). When AAV5.BMI1 was administered at a dose of $5 \times 10^9$ vg/eye of AAV5.BMI1, there was a statistically significant increase of BMI1 protein on RPE-choroid when compared to the control (FIG. 7C). FIGS. 7D, 7E and 7F each show that no alteration of the ocular histology was found in either the control (FIG. 7D), an eye that received $1\times10^9$ vg/eye of AAV5.BMI1 (FIG. 7E) or an eye that received 5×109 vg/eye of AAV5.BMI1 (FIG. 7F).

Example 14: Effect of BMI1 in an AMD Model of Retinal Degeneration Induced by Sodium Iodate Background: The ability of BMI1 to protect the retina from damage induced by NaIO3 in vivo was evaluated in a pilot study.

Methodology: For this work, 6-week-old Balb/c mice were obtained from The Jackson Laboratory. One mouse per group was injected subretinally with 1×109 vg/eye of AAV5.BMI1 and saline. For all experiments, mice were anaesthetized using Isofluorane. Following anaesthetizing the mice, the pupils of each of the mice were dilated using topical 1% tropicamide and 2.5% phenylepherine. AAV5.BMI1 was injected into the subretinal space of the eye with the tip of a 10-mm 33-gauge hypodermic needle mounted on a 10 µl syringe (Hamilton). 1 µl of vector suspension was then injected subretinally at a dose rage of $1\times10^7$ or $5\times10^{10}$ vg/eye. Control mice were injected with 1 µl of Saline solution (NaCl 0.9%). All mice had chloramphenicol 1% eye ointment applied to the cornea. The mice were euthanized 4 weeks after the injection and eyes were enucleated and the retina was dissected in the right eyes. The tissue was flash frozen in liquid nitrogen and then was processed for mRNA extraction. After the subretinal injection of saline and AAV5.BMI1, mice were injected intraperitoneally with $NaIO_3$ (50 mg/Kg). The mice without NaIO3 injection were used as control group. The control mice were also euthanized 4 weeks after the injection and eyes were enucleated and the retina was dissected in the right eyes.

Total mRNA was extracted from tissues using Trizol (Thermo Fisher Scientific) according to the manufacturer's instructions. The quantity and quality of the mRNA was determined using a NanoDrop spectrophotometer (Nano-Drop Technologies). First-strand cDNA synthesis was performed by a reaction of 1.0 µg of total mRNA with a random primer, using the Maxima Reverse Transcriptase Kit (Thermo Fisher Scientific). Conventional RT-PCR (qRT-PCR) was performed using the TaqMan Fast Advanced Master Mix (Thermo Fisher Scientific). qPCR was performed on a total of 20 µl of mixture solution in 96-well plates using the QuantStudio 6 Pro system (Thermo Fisher Scientific). Each 20 µl of reaction mixture contained 10 µl of SYBR Green Master (Thermo Fisher Scientific), 0.5 µM primers, and diluted cDNA. Real-time PCR quantifications were run in triplicate for each sample, the average was determined, and PCR products were quantified using the QuantStudio 6 Pro software. Expression levels were normalized to GAPDH levels. Gene-fold changes of BMI1 were normalized to the Cornea gene expression. The sequence of the primers used for are listed in Table 1.

For histological analysis, the left eyes were embedded in OCT and frozen in isopentane cooled by liquid nitrogen. The tissue was sectioned on a cryostat (Leyca) with section slices of 10 µm followed by Hematoxylin-Eosin (H&E) staining for morphological observation of the retinal layers. ONL and total retina thickness were measured using the Image J software. For Rhodopsin staining, 10 µm cryosections of the eye were fixed in 4% Paraformaldehyde (PFA). Rinsed three times in Phosphate Buffer Saline (PBS) for 5 minutes, they were permeabilized in PBS-0.2% Triton X-100 for 15 minutes, retinal sections were incubated in IHC/ICC Blocking Buffer—High Protein (Thermo Fisher Scientific) for 60 minutes, and then, they were incubated with Blocking Buffer containing the mouse B630 anti-rhodopsin antibody 1:500 (Novus Biologicals) over night at 4 C in a humidified chamber. The retinal sections were washed with PBS four times and incubated with Alexa conjugated goat anti-mouse antibody (Thermo Fisher Scientific) for 1 hour at room temperature. DAPI (1:10,000 dilution) was applied for 5 minutes to stain the nuclei. Sections were mounted with the Fluoromount G mounting solution (Thermo Fisher Scientific). Immunofluorescence images were then taken by a EVOS Cell Imaging System (Thermo Fisher Scientific).

Figure 8A:
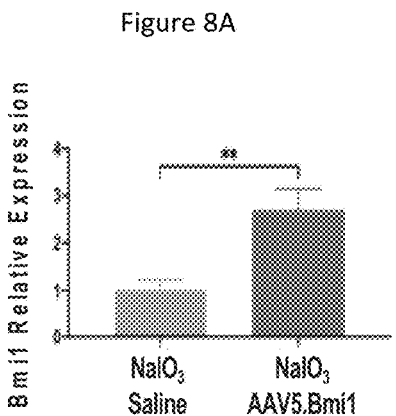
FIG. 8A shows the relative expression levels of BMI1 mRNA in the retina of a control that received $NaIO_3$-saline and a retina treated with $NaIO_3$ and was transduced with AAV5.BMI1 for 4 weeks. mRNA was amplified using qRT-PCR with primers for the mouse BMI1 gene. GAPDH was used as a control. Values are expressed as mean±SD. Values are normalized to the control levels of BMI1 levels in $NaIO_3$-saline treated eyes. **P value<0.01 (unpaired t-test).
Figures 8B, 8C, 8D:
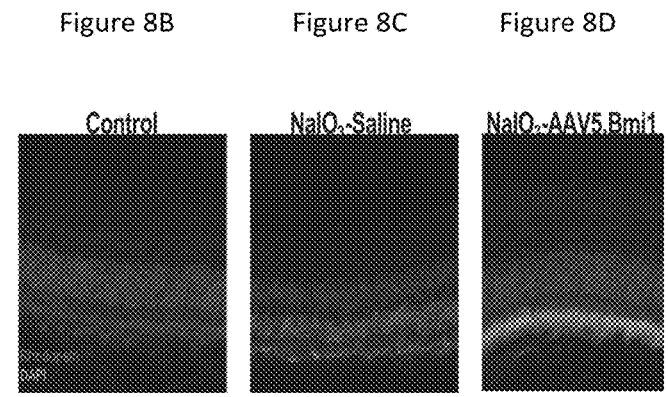
FIGS. 8B-8D shows the results from indirect immuno-fluorescence using Rhodopsin-stained eye sections that were obtained from eyes that received no injection (FIG. 8B), an eye that received $NaIO_3$-saline (FIG. 8C) and an eye that received $NaIO_3$-AA5.BMI1 (FIG. 8D). Nuclei are label with DAPI.
Figures 8E, 8F, 8G, 8H:
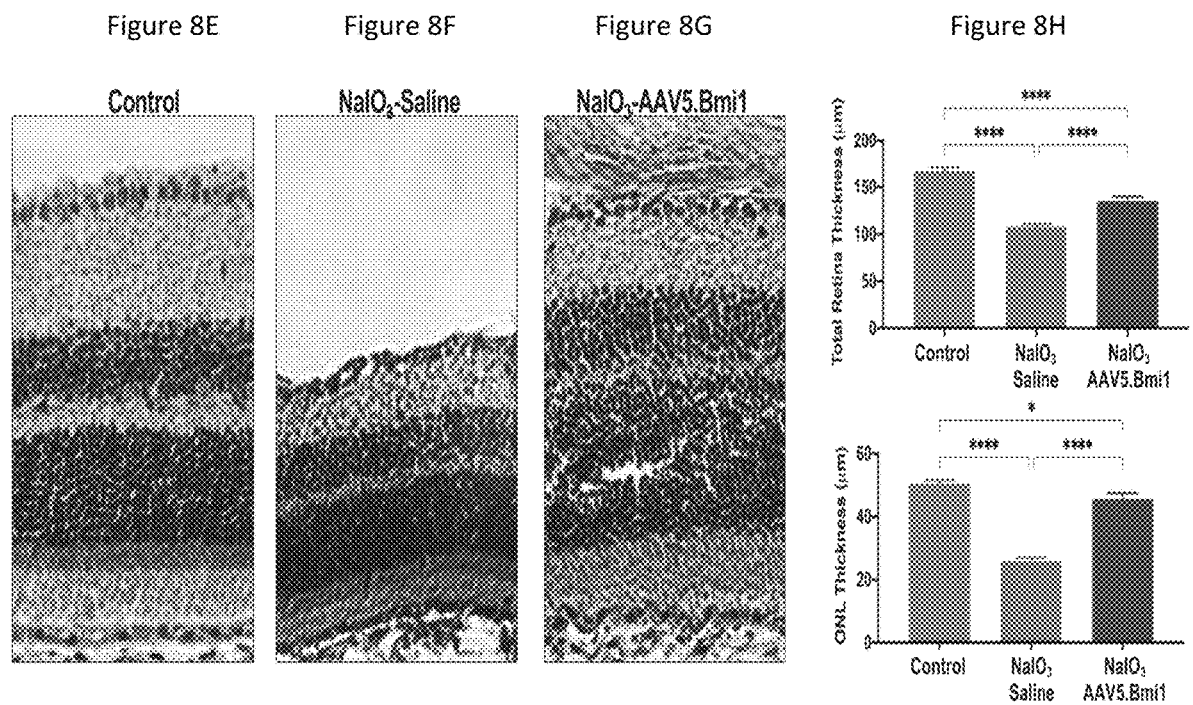
FIG. 8E-8G shows representative images of an H&E stained eye section obtained from a control (FIG. 8E), $NaIO_3$-saline treated (FIG. 8F) and $NaIO_3$-AA5.BMI1 treated group (FIG. 8G).
FIG. 8H shows the results from the measurement of the thickness of a retina (upper graph) and ONL (lower graph) that was quantified using the H&E images shown in FIG. 8E-8G. Values are expressed as mean±SD. *P value<0.05, ****P value<0.0001 (One-way ANOVA).

Results: FIG. 8A shows an increase in mRNA expression in the $NaIO_3$-AAV5.BMI1 mouse compared to the control ($NaIO_3$-Saline) mouse. As can be seen in FIG. 8A, the efficient transduction of the AAV in mouse retina resulted in an increase in $NaIO_3$ damaged eyes. FIGS. 8B, 8C and 8D show the photoreceptor (rods) in a control mouse (no $NaIO_3$) (FIG. 8B), a mouse that received $NaIO_3$-saline (FIG. 8C) and a mouse that received $NaIO_3$ and AAV5.BMI1 (FIG. 8D). As seen, recovery occurred in the $NaIO_3$-AAV5.BMI1 mice (FIG. 8D) when compared to the $NaIO_3$-saline mice (FIGS. 8B and 8C). In FIGS. 8E-8G, the eye sections of the control, $NaIO_3$-saline and the $NaIO_3$-AAV5.BMI1 mice were immunostained with rhodopsin to visualize the rods cells that are present in the photoreceptor layer of the retina. The histological analysis shown in FIGS. 8E-8G shows that $NaIO_3$ induced a decrease in the retinal thickness of the two control groups (FIGS. 8E and 8F) when compared to the mouse treated with $NaIO_3$ and AAV5.BMI1 (FIG. 8G). In the AAV5.BMI1 group, it is seen that the retinal thickness and ONL thickness has been restored—when FIG. 8E is compared to FIG. 8G. This result is confirmed in FIG. 8H, which shows that the retina and ONL thickness of the AAV5.BMI1 group was similar to the control mouse that did not receive $NaIO_3$.

Example 15: BMI1 Protects from Retinal Degeneration in an AMD Model Induced by Sodium Iodate Background: To corroborate the data obtained in the prior Example, the ability of BMI1 to protect the retina from damage induced by $NaIO_3$ in vivo was evaluated in a larger group of mice.

Methodology: For this work, 6-week-old Balb/c mice were obtained from The Jackson Laboratory. The AAV BMI1 treated mice were injected subretinally with 1×109 vg/eye of AAV5.BMI1 (n=20) and saline (n=11). For all experiments, mice were anaesthetized using Isofluorane. Following anaesthetizing the mice, the pupils of all animals were dilated using topical 1% tropicamide and 2.5% phenylephrine. AAV5.BMI1 was injected into the subretinal space of the eye with the tip of a 10-mm 33-gauge hypodermic needle mounted on a 10 µl syringe (Hamilton). 1 µl of vector suspension was then injected subretinally at a dose rage of $1\times10^7$ or $5\times10^{10}$ vg/eye. Control animals were injected with 1 µl of Saline solution (NaCl 0.9%). All animals received chloramphenicol 1% eye ointment to the cornea. 4 weeks after the subretinal injection of saline and AAV5.BMI1, mice were injected intraperitoneally with $NaIO_3$ (50 mg/Kg). Mice without NaIO3 injection were used as control group (n=4). In vivo imaging was performed 1 week after $NaIO_3$ injection with a spectral domain optical coherence tomography (OCT) device modified for use in mice (Spectralis Multiline, Heidelberg Engineering GmbH, Heidelberg, Germany). Mice were anaesthetized using Isofluorane. The pupils were dilated with a mixture of tropicamide and phenylephrine. Artificial tears were used throughout the procedure to maintain corneal hydration and clarity. 25 linear β-scans, each the average of 9 frames were obtained and used to quantify outer retinal thickness.

Figure 9:
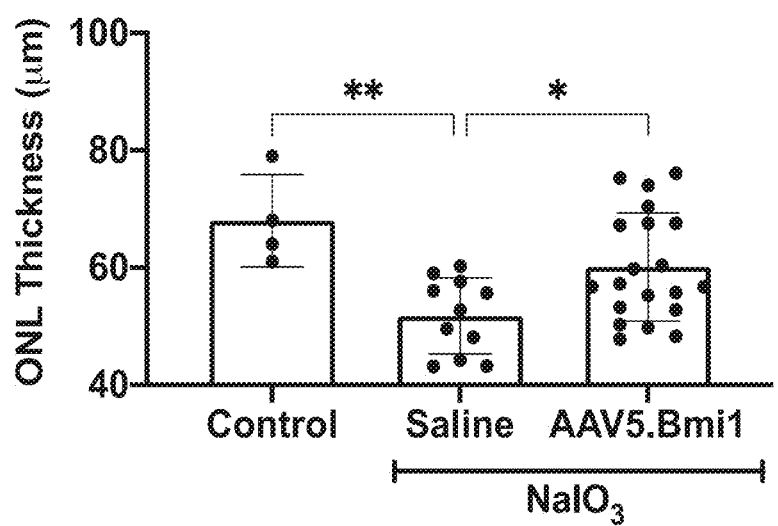
FIG. 9 shows the results from the measurement of the thickness of ONL that was quantified using OCT scanning in control mice, $NaIO_3$ mice injected with Saline and $NaIO_3$ mice injected with AAV5.BMI1 Values are expressed as mean±SD. *P value<0.05, P value<0.01 **P value<0.0001 (One-way ANOVA).

Results: FIG. 9 shows the decrease in ONL thickness in mice treated with $NaIO_3$ and the effect of BMI1 in the AAV BMI1 treated mice to prevent this degeneration.

Example 16: BMI1 Protects from Retinal Degeneration in Light Induced Retinopathy Model Background: To corroborate the data obtained in the sodium iodate model we evaluated the ability of BMI1 to protect mice from light induced retinopathy (LIR) in vivo.

Methodology: For this work, 6-week-old Balb/c mice were obtained from The Jackson Laboratory. The mice were injected subretinally with $1\times10^9$ vg/eye of AAV5.BMI1 (n=15) and saline (n=7). For all experiments, mice were anaesthetized using Isofluorane. Following anaesthetizing the mice, the pupils of all animals were dilated using topical 1% tropicamide and 2.5% phenylephrine. AAV5.BMI1 was injected into the subretinal space of the eye with the tip of a 10-mm 33-gauge hypodermic needle mounted on a 10 μl syringe (Hamilton). 1 μl of vector suspension was then injected subretinally at a dose rage of $1\times10^7$ or $5\times10^{10}$ vg/eye. Control animals were injected with 1 μl of Saline solution (NaCl 0.9%). All animals received chloramphenicol 1% eye ointment to the cornea. 4 weeks after the subretinal injection of saline and AAV5.BMI1, mice were induced with retinal degeneration via exposure to intense white LED light (LIR). 1% cyclopentolate hydrochloride and 2.5% phenylephrine was used in combination for the dilation of mice pupils. Upon a 45-minute dark adaptation, the mice were individually placed in aluminium foil-wrapped containers with direct exposure to 6,000 K and 12,000-15,000 lux light for 2 hours to induce degeneration of photo receptors. Temperature inside the container was kept constant using the mini-fans. Following the intense light exposure, the mice were placed back into the normal 12-hour light/dark cycle. In vivo imaging was performed 1 week after $NaIO_3$ injection with a spectral domain optical coherence tomography (OCT) device modified for use in mice (Spectralis Multiline, Heidelberg Engineering GmbH, Heidelberg, Germany). Mice were anaesthetized using Isofluorane. The pupils were dilated with a mixture of tropicamide and phenylephrine. Artificial tears were used throughout the procedure to maintain corneal hydration and clarity. 25 linear B-scans, each the average of 9 frames were obtained and used to quantify outer retinal thickness.

Figure 10:
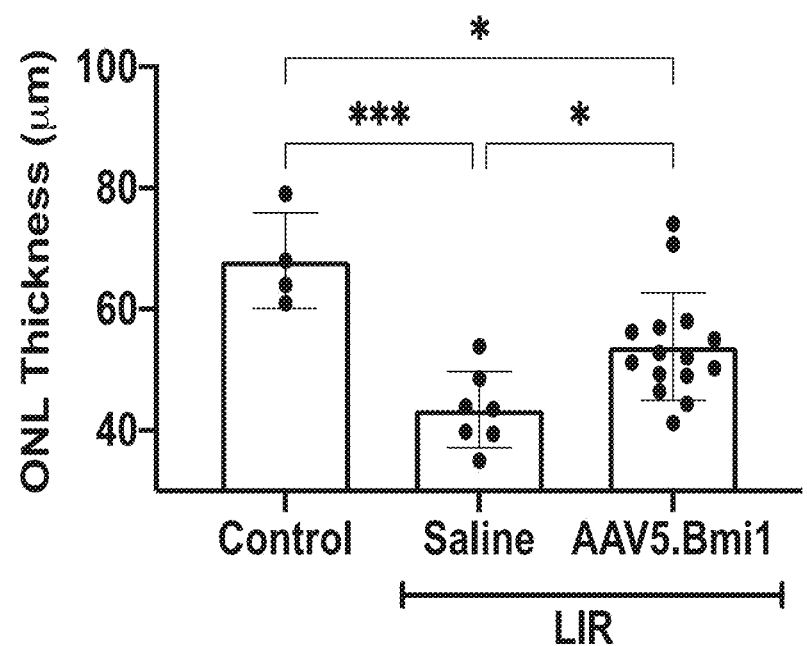
FIG. 10 shows the results from the measurement of the thickness of ONL that was quantified using OCT scanning in control mice, LIR mice injected with Saline and LIR mice injected with AAV5.BMI1. Values are expressed as mean±SD. *P value<0.05, P value<0.01 **P value<0.0001 (One-way ANOVA).

Results: FIG. 10 shows the decrease in ONL thickness in control mice subject to LIR and the effect of BMI1 administered in an AAV in the treated mice to prevent this degeneration.

Example 17: AAVrh10.BMI1 Transduced Efficiently Human Retinal Explants

Background: Evaluation of the ability of an AAVrh10.BMI1 to transduce a human retina.

Methodology: Two human donor eyes were obtained from One Legacy Foundation (Los Angeles, Calif.). The specimens were kept in optimal conditions until the delivery to our facility. Upon arrival the eyes were dissected to obtain a 5 mm diameter retinal explant using a dermal punch. The retinal explants were washed in Hanks' Balanced Salt Solution (HBSS) and then were incubated in a 37° C. 5% $CO_2$ incubator in explant medium (Neurobasa™), a medium supplemented with B-27 Supplement and N-2 Supplement, 200 mM Glutamine and Antibiotic-Antimycotic). AAV5.BMI1 was added to the explant medium ($1\times10^{11}$ vg/ml) and the explants were incubated for 5 days. One retinal explant for each donor was not transduced and was used as control.

Total mRNA was extracted from tissues using Trizol (Thermo Fisher Scientific) according to the manufacturer's instructions. The quantity and quality of the mRNA was determined using a NanoDrop spectrophotometer (NanoDrop Technologies). First-strand cDNA synthesis was performed by a reaction of 1.0 μg of total mRNA with a random primer, using the Maxima Reverse Transcriptase Kit (Thermo Fisher Scientific). Conventional RT-PCR (qRT-PCR) was performed using the TaqMan Fast Advanced Master Mix (Thermo Fisher Scientific). qPCR was performed on a total of 20 μl of mixture solution in 96-well plates using the QuantStudio 6 Pro system (Thermo Fisher Scientific). Each 20 μl of reaction mixture contained 10 μl of SYBR Green Master (Thermo Fisher Scientific), 0.5 μM primers, and diluted cDNA. Real-time PCR quantifications were run in triplicate for each sample, the average was determined, and PCR products were quantified using the QuantStudio 6 Pro software. Expression levels were normalized to GAPDH levels. Gene-fold changes of BMI1 were normalized to the retina gene expression. The sequence of the primers used for are listed in Table 1.

Figure 11:
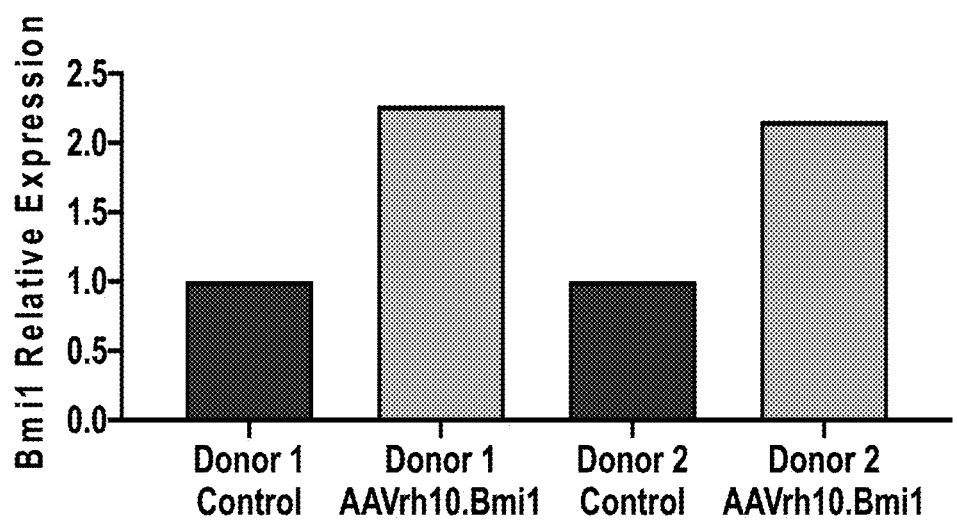
FIG. 11 shows the results following extraction of total mRNA from the retina of human donors' eyes that were treated with AAVrh10.BMI1 for five days. The mRNA was subjected to qRT-PCR using primers for a human BMI1 gene. Human GAPDH was used as a control. Values are expressed as mean±SD. Values are normalized to the retina expression of BMI1 without AAV transduction.

Results: As shown in FIG. 11. mRNA levels of BMI1 increased by approximately 2-fold in retinal explants that had been transduced with AAVrh10.BMI1.

Example 18: Effect of BMI1 in Cell Proliferation, Cell Viability and Cell Toxicity In Vitro Methodology: ARPE-19 cells were grown at 5% $CO_2$/37° C. in DMEM-F12 media supplemented with 10% FBS until the cells reached confluency. This was followed by the cells being transduced with 1×109 vg in a 50 μL medium/well that contained AAV5.BMI-1 or AAV5.BMI1-shRNA for 72 hours. Cell viability was measured in transfected cells treated for 15 hours with different doses of $NaIO_3$ (Sigma). The assessment of mitochondrial damage was performed using a 3-(4,5-dimethylthiazol-2-yl)-2,5-diphenyl tetrazolium bromide (MTT) assay (Thermo Fisher Scientific). After stimulation, the cells were washed with PBS and incubated with 20 μl of stock MTT solution for 4 hours. This was followed by the addition of 200 μl DMSO to each well. Then the plates were shaken for 15 minutes on a plate shaker at room temperature. Cell viability was determined by measuring the optical density at 570 nm using an ELISA plate reader. Cell toxicity was measured in AAV transfected cells treated with different concentrations of tert-Butyl hydroperoxide (tBH). Briefly, cells were seeded in 96-well plates. Then 72 hours after the transduction with BMI-1 and BMI-1 shRNA the culture media were replaced with serum-free media containing tBH at indicated concentrations and incubated for 15 hours. Toxicity was determined by measuring the cytoplasmic lactate dehydrogenase enzyme in conditioned media with CyQUANT™ LDH Cytotoxicity Assay (Thermo Fisher Scientific). The absorbance was measured using an ELISA microplate reader.

Figure 12A:
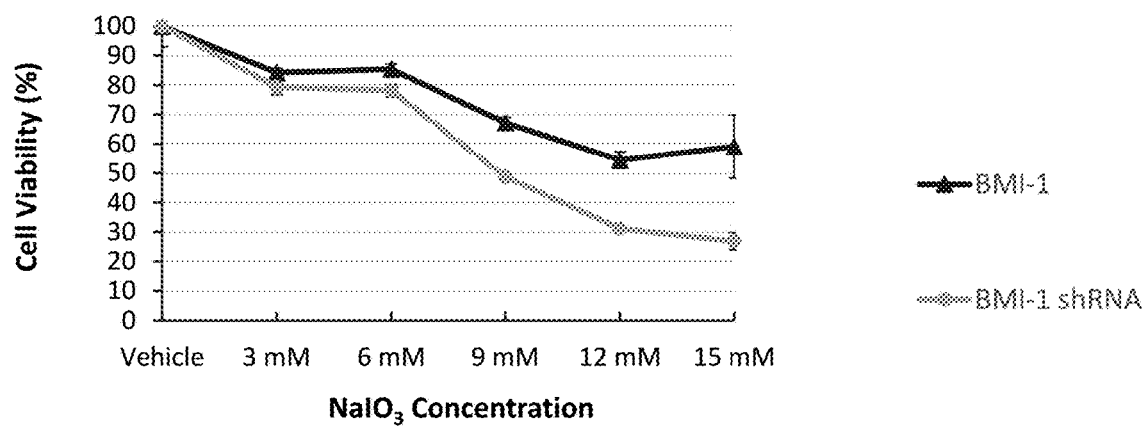
FIG. 12A shows that ARPE-19 cells with overexpressed BMI1 had significantly increased cell viability (P<0.001) with $NaIO_3$ exposure compared with knock-down BMI1 expression by shRNA. Values represent mean±SD.
Figure 12B:
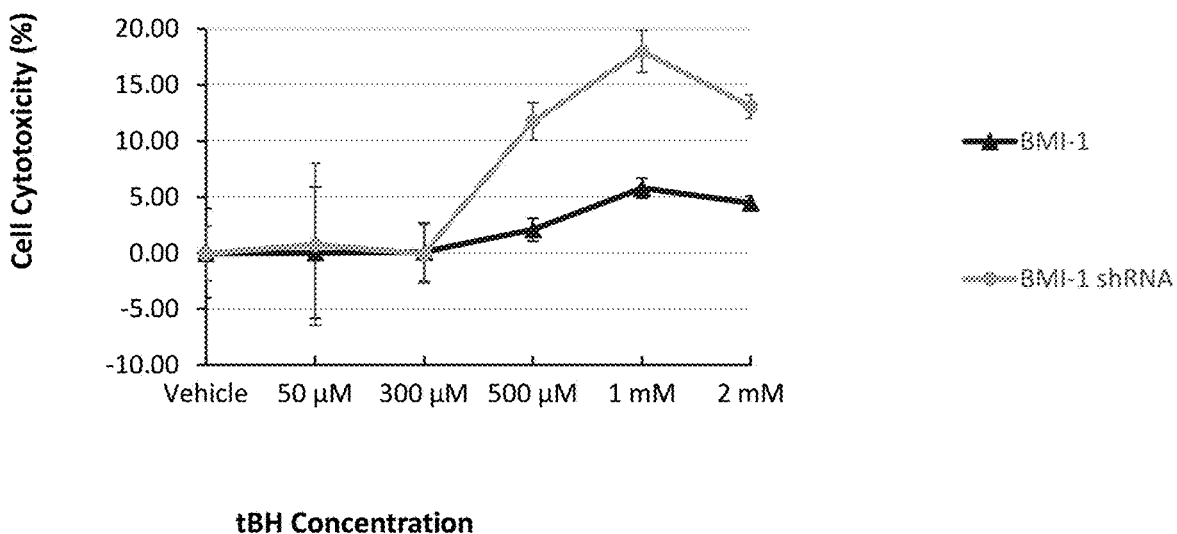
FIG. 12B shows LDH level, a measure of cytotoxicity, is significantly higher in BMI1 shRNA cells compared to cells treated with BMI1 overexpression. Values represent mean±SD.

Results: FIG. 12A shows that ARPE-19 cells with overexpressed BMI1 had significantly increased cell viability with $NaIO_3$ exposure compared with cells where BMI1 expression was knocked-down by shRNA. FIG. 12B shows the LDH level, which is a measure of cytotoxicity. In FIG. 12B, it is seen that cytotoxicity was significantly higher in BMI1 shRNA cells compared to cells treated with BMI1 overexpression.

Example 19: AAV5. Bmi1 Infection in ARPE-19 Cells Changed the Expression of Genes Involved in Multiple Cellular Pathways Background: A gene expression analysis was undertaken to determine the molecular mechanisms that are involved in the genetic pathways of BMI1 function in ARPE-19 cells. These mechanisms include cellular proliferation/apoptosis/senescence.

Methodology: ARPE-19 cells were cultured and maintained in Dulbecco's Modified Eagle's Medium (DMEM) (Gibco) supplemented with 10% FBS (Invitrogen) and 1% penicillin/streptomycin (Invitrogen). The cells were plated at a density of $0.5 \times 10^6$ cells per well in 35 mm six-well plates. Twelve hours later the cells were infected with either AAV5.NM201 (treated group) or AAV5.GFP (control group) at a range of 2500-60000 MOI. Forty-eight hours following viral infection, the confluent monolayers were exposed to the oxidative stress using tert-butyl hydroperoxide (tBH) (Invitrogen) for 1 hour. Then, total mRNA was extracted from the cells using Trizol (Thermo Fisher Scientific) according to the manufacturer's instructions. The quantity and quality of the mRNA was determined using a NanoDrop spectrophotometer (NanoDrop Technologies). First-strand cDNA synthesis was performed by a reaction of 1.0 µg of total mRNA with a random primer, using the Maxima Reverse Transcriptase Kit (Thermo Fisher Scientific). Conventional RT-PCR (qRT-PCR) was performed using the TaqMan Fast Advanced Master Mix (Thermo Fisher Scientific). qPCR was performed on a total of 20 µl of mixture solution in 96-well plates using the QuantStudio 6 Pro system (Thermo Fisher Scientific). Each 20 µl of reaction mixture contained 10 µl of SYBR Green Master (Thermo Fisher Scientific), 0.5 µM primers, and diluted cDNA. Real-time PCR quantifications were run in triplicate for each sample, the average was determined, and PCR products were quantified using the QuantStudio 6 Pro software. Expression levels were normalized to GAPDH levels. The sequence of the primers used are listed in Table 1.

Figure 13A:
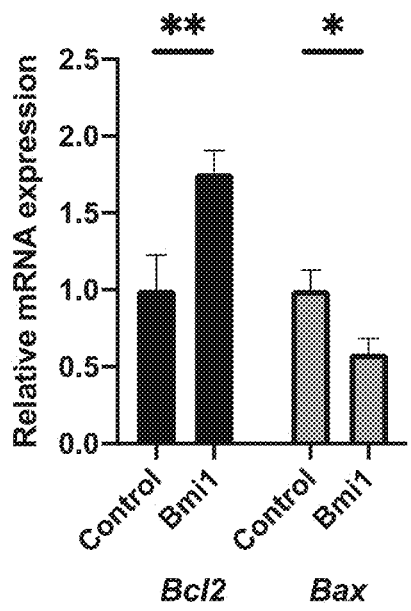
FIG. 13A is the quantification graph of the mRNA expression change in Bcl2 and Bax genes, involved in cellular apoptosis, via qRT-PCR analysis upon transduction of AAV5.BMI1 (Bmi1) in ARPE-19 cells. Values are normalized to the mRNA levels of ARPE-19 cells without transduction (Control). *P value<0.05, **P value<0.01 (unpaired t-test).
Figure 13B:
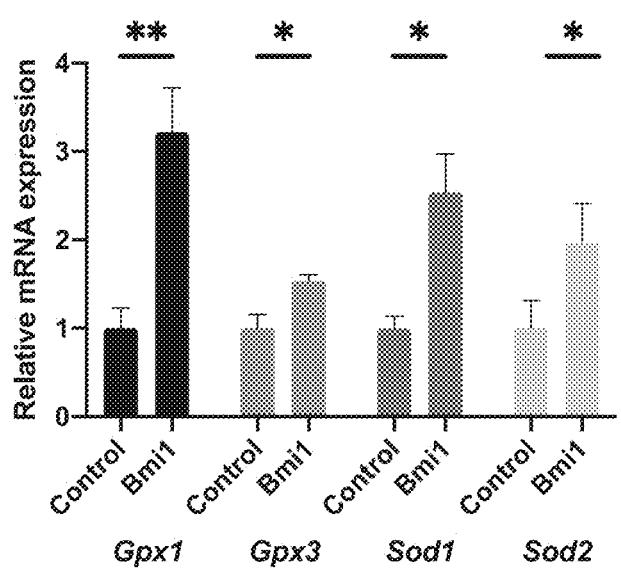
FIG. 13B is the quantification graph of the mRNA expression change in Gpx1, Gpx3, Sod1, and Sod2, involved in cellular resistance to oxidative stress, via qRT-PCR analysis upon transduction of AAV5.BMI1 (Bmi1) in ARPE-19 cells. Values are normalized to the mRNA levels of ARPE-19 cells without transduction (Control). *P value<0.05, **P value<0.01 (unpaired t-test).
Figure 13C:
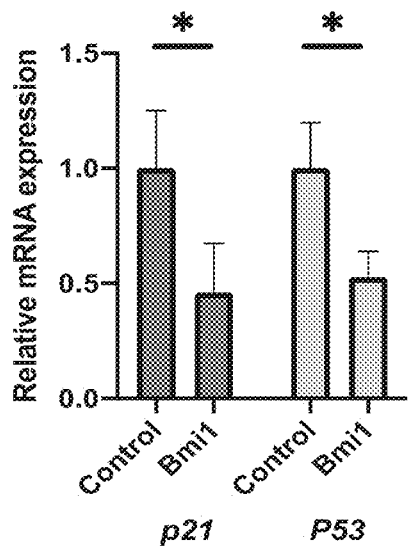
FIG. 13C is the quantification graph of the mRNA expression change in P21 and p53, involved in cellular senescence to oxidative stress, via qRT-PCR analysis upon transduction of AAV5.BMI1 (Bmi1) in ARPE-19 cells. Values are normalized to the mRNA levels of ARPE-19 cells without transduction (Control). *P value<0.05 (unpaired t-test).
Figure 13D:
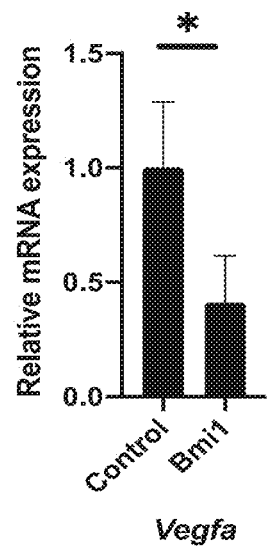
FIG. 13D is the quantification graph of the mRNA expression change in Vegfa, involved in inflammatory response, via qRT-PCR analysis upon transduction of AAV5.Bmi1 (Bmi1) in ARPE-19 cells. Values are normalized to the mRNA levels of ARPE-19 cells without transduction (Control). *P value<0.05 (unpaired t-test).

Results: FIG. 13A-13D shows that the overexpression of BMI1 via AAV5.Bmi1 increased the Bcl2/Bax ratio (FIG. 13A), which correlated in a reduction in apoptosis of the ARPE-19 cells. BMI1 also upregulated the mRNA expression of Gpx1, Gpx3, Sod1, and Sod2 (FIG. 13B), which correlated with resistance of the treated group cells to oxidative stress in ARPE-19 cells. In addition, the treated group of cells had downregulated the mRNA expression of p21, p53 (FIG. 13C), and Vegfa (FIG. 13D). This correlated with a reduction of cellular senescence and inflammatory response in the ARPE-19 cells.

Example 20: Subretinal Injection of AAV5. Bmi1 in Balb/c Mice Changed the Expression of Genes Involved in Multiple Cellular Pathways Background: The work disclosed in this example was undertaken to determine the molecular mechanisms that are involved in the genetic pathways of BMI1 expression in the eyes of a mouse. This was done through a gene expression analysis to evaluate the requirement for a cellular proliferation/apoptosis/senescence network.

Methodology: 6-week-old Balb/c mice were obtained from The Jackson Laboratory. For all experiments, mice were anaesthetized using Isofluorane. Following anaesthetizing the mice, the pupils of all animals were dilated using topical 1% tropicamide and 2.5% phenylephrine. AAV5.BMI1 was injected into the subretinal space of the eye with the tip of a 10-mm 33-gauge hypodermic needle mounted on a 10 µl syringe (Hamilton). 1 µl of vector suspension was then injected subretinally at a dose rage of $1 \times 10^7$ or $5 \times 10^{10}$ vg/eye. Control animals were injected with 1 µl of Saline solution (NaCl 0.9%). All animals received chloramphenicol 1% eye ointment which was applied to the cornea. The mice were euthanized 4 weeks after the injection and eyes were enucleated and the retina was dissected in the right eyes. The tissue was flash frozen in liquid nitrogen and then was processed for mRNA and protein extraction. Then total mRNA was extracted from the cells using Trizol (Thermo Fisher Scientific) according to the manufacturer's instructions. The quantity and quality of the mRNA was determined using a NanoDrop spectrophotometer (NanoDrop Technologies). First-strand cDNA synthesis was performed by a reaction of 1.0 µg of total mRNA with a random primer, using the Maxima Reverse Transcriptase Kit (Thermo Fisher Scientific). Conventional RT-PCR (qRT-PCR) was performed using the TaqMan Fast Advanced Master Mix (Thermo Fisher Scientific). qPCR was performed on a total of 20 µl of mixture solution in 96-well plates using the QuantStudio 6 Pro system (Thermo Fisher Scientific). Each 20 µl of reaction mixture contained 10 µl of SYBR Green Master (Thermo Fisher Scientific), 0.5 µM primers, and diluted cDNA. Real-time PCR quantifications were run in triplicate for each sample, the average was determined, and PCR products were quantified using the QuantStudio 6 Pro software. Expression levels were normalized to GAPDH levels. The sequence of the primers used are listed in Table 1.

Figure 14A:
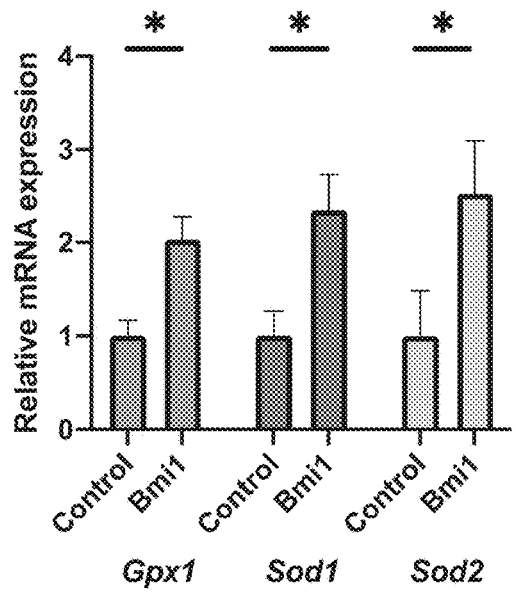
FIG. 14A is the quantification graph of the mRNA expression change in Gpx1, Sod1, and Sod2 involved in cellular resistance to oxidative stress via qRT-PCR analysis upon subretinal injection of AAV5.BMI1 (Bmi1) in Balb/c mice. Values are normalized to the mRNA levels of ARPE-19 cells without transduction (Control). *P value<0.05 (unpaired t-test).
Figure 14B:
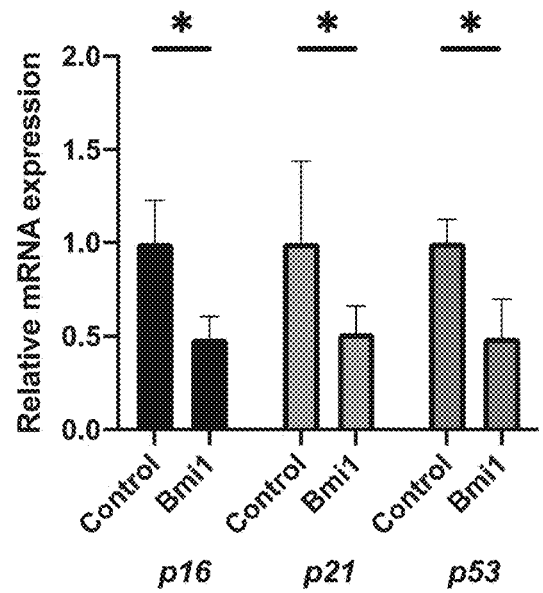
FIG. 14B is the quantification graph of the mRNA expression change in P21 and p53 involved in cellular senescence to oxidative stress via qRT-PCR analysis upon subretinal injection of AAV5.BMI1 (Bmi1) in Balb/c mice. Values are normalized to the mRNA levels of ARPE-19 cells without transduction (Control). *P value<0.05 (unpaired t-test).
Figure 14C:
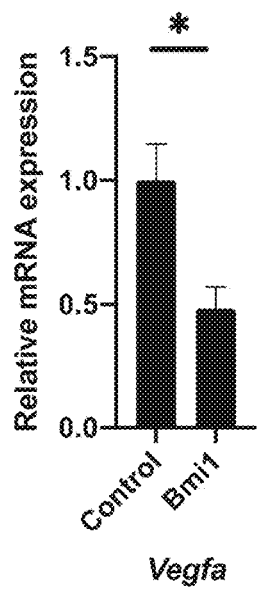
FIG. 14C is the quantification graph of the mRNA expression change in Vegfa involved in inflammatory response of the RPE cells via qRT-PCR analysis upon subretinal injection of AAV5.BMI1 (Bmi1) in Balb/c mice. Values are normalized to the mRNA levels of ARPE-19 cells without transduction (Control). *P value<0.05 (unpaired t-test).

Results: FIG. 14A-14C show that the overexpression of BMI1 following administration of AAV5.NM201 resulted in an upregulation of the mRNA expression of Gpx1, Sod1, and Sod2 (FIG. 14A). This correlated with a resistance to oxidative stress in the AAV5.NM201 treated mouse eyes. Additionally, administration of AAV5.NM201 correlated with the downregulation of the mRNA expression of p16, p21, p53 (FIG. 14B), and Vegfa (FIG. 14C). This downregulation correlated with a reduction of cellular senescence and inflammatory response in mouse eyes.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter. Further, the use of the terms "include," "includes" and "including" means include, includes and or including as well as include, includes and including, but not limited to.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only and is not intended to limit the scope of the present invention, which is defined solely by the claims. Accordingly, the present invention is not limited to that precisely as shown and described.

Although embodiments of the current disclosure have been described comprehensively in considerable detail to cover the possible aspects, those skilled in the art would recognize that other versions of the disclosure are also possible.

While the present invention has been described in terms of particular embodiments and applications, in both summarized and detailed forms, it is not intended that these descriptions in any way limit its scope to any such embodiments and applications, and it will be understood that many substitutions, changes and variations in the described embodiments, applications and details of the method and system illustrated herein and of their operation can be made by those skilled in the art without departing from the spirit of this invention.

What is claimed is:

1. A method of treating a retinopathy in a patient suffering from macular degeneration, the method comprising;
   administering to the patient by intravitreal, subretinal, suprachoroidal and/or sub-internal limiting membrane injection an effective amount of an adeno-associated virus (AAV) encoding a heterologous BMI1 protein into an eye of the patient,
   wherein the AAV is selected from one of serotypes 2, 5, 7, 8, 9 or rh10,
   wherein said administration results in transduction of a retinal pigment epithelium (RPE) cell by the AAV encoding the heterologous BMI1 protein;
   wherein said transduction results in expression of the therapeutically effective amount of the heterologous BMI1 protein in the transduced RPE cell; and
   wherein the expression of the heterologous BMI1 protein in the RPE cell results in a reduction in macular degeneration in the patient suffering from macular degeneration.

2. The method of claim 1, wherein the BMI1 protein is constitutively expressed in the transduced RPE cell.

3. The method of claim 1, wherein the BMI1 protein is expressed with an inducible or constitutive promoter.

4. The method of claim 1, wherein the effective amount of the AAV is about $10^5$, $10^6$, $10^7$, $10^8$, $10^9$, $10^{10}$, $10^{11}$, $10^{12}$, $10^{13}$, $10^{14}$, or $10^{15}$ vg/eye.

5. The method of claim 1, wherein the treatment results in a reduction of progression of macular degeneration by about 15% compared to the progression of macular degeneration in the absence of treatment.

6. The method of claim 1, wherein the treatment improves the vision of the patient by about 15% compared to the same individual in the absence of treatment.

* * * * *

SEQUENCE LISTING

<160> NUMBER OF SEQ ID NOS: 42

<210> SEQ ID NO 1
<211> LENGTH: 21
<212> TYPE: DNA
<213> ORGANISM: artificial
<220> FEATURE:
<223> OTHER INFORMATION: primer qh.Bax-F (Forward)

<400> SEQUENCE: 1
catataaccc cgtcaacgca g                                              21

<210> SEQ ID NO 2
<211> LENGTH: 19
<212> TYPE: DNA
<213> ORGANISM: artificial
<220> FEATURE:
<223> OTHER INFORMATION: qh.Bax-R (Reverse)

<400> SEQUENCE: 2
gcagccgcca caaacatac                                                 19

<210> SEQ ID NO 3
<211> LENGTH: 22
<212> TYPE: DNA
<213> ORGANISM: artificial
<220> FEATURE:
<223> OTHER INFORMATION: qh.Bcl2-F

<400> SEQUENCE: 3
atcgccctgt ggatgactga gt                                             22

<210> SEQ ID NO 4
<211> LENGTH: 23
<212> TYPE: DNA
<213> ORGANISM: artificial
<220> FEATURE:
<223> OTHER INFORMATION: qh.Bcl2-R

<400> SEQUENCE: 4
gccaggagaa atcaaacaga ggc                                            23

```
<210> SEQ ID NO 5
<211> LENGTH: 19
<212> TYPE: DNA
<213> ORGANISM: artificial
<220> FEATURE:
<223> OTHER INFORMATION: qh.Gapdh-F

<400> SEQUENCE: 5
aggtcggtga acggatttg                                                 19

<210> SEQ ID NO 6
<211> LENGTH: 23
<212> TYPE: DNA
<213> ORGANISM: artificial
<220> FEATURE:
<223> OTHER INFORMATION: qh.Gapdh-R

<400> SEQUENCE: 6
tgtagaccat gtagttgagg tca                                            23

<210> SEQ ID NO 7
<211> LENGTH: 22
<212> TYPE: DNA
<213> ORGANISM: artificial
<220> FEATURE:
<223> OTHER INFORMATION: qh.Gpx1-F

<400> SEQUENCE: 7
caatcagttc ggacaccagg ag                                             22

<210> SEQ ID NO 8
<211> LENGTH: 23
<212> TYPE: DNA
<213> ORGANISM: artificial
<220> FEATURE:
<223> OTHER INFORMATION: qh.Gpx1-R

<400> SEQUENCE: 8
tctcaccatt cacttcgcac ttc                                            23

<210> SEQ ID NO 9
<211> LENGTH: 23
<212> TYPE: DNA
<213> ORGANISM: artificial
<220> FEATURE:
<223> OTHER INFORMATION: qh.Gpx3-F

<400> SEQUENCE: 9
cttcttcttg ttgagctgga ctc                                            23

<210> SEQ ID NO 10
<211> LENGTH: 21
<212> TYPE: DNA
<213> ORGANISM: artificial
<220> FEATURE:
<223> OTHER INFORMATION: qh.Gpx3-R

<400> SEQUENCE: 10
ctgtggaggt cactgtagac t                                              21

<210> SEQ ID NO 11
<211> LENGTH: 23
<212> TYPE: DNA
<213> ORGANISM: artificial
<220> FEATURE:
<223> OTHER INFORMATION: qh.BMI1-F
```

<400> SEQUENCE: 11
ggtacttcat tgatgccaca acc                                              23

<210> SEQ ID NO 12
<211> LENGTH: 23
<212> TYPE: DNA
<213> ORGANISM: artificial
<220> FEATURE:
<223> OTHER INFORMATION: qh.BMI1-R

<400> SEQUENCE: 12
ctggtcttgt gaacttggac atc                                              23

<210> SEQ ID NO 13
<211> LENGTH: 20
<212> TYPE: DNA
<213> ORGANISM: artificial
<220> FEATURE:
<223> OTHER INFORMATION: qh.p21-F

<400> SEQUENCE: 13
agtatgccgt cgtctgttcg                                                  20

<210> SEQ ID NO 14
<211> LENGTH: 20
<212> TYPE: DNA
<213> ORGANISM: artificial
<220> FEATURE:
<223> OTHER INFORMATION: qh.p21-R

<400> SEQUENCE: 14
gactgcaaga cagcgacaag                                                  20

<210> SEQ ID NO 15
<211> LENGTH: 21
<212> TYPE: DNA
<213> ORGANISM: artificial
<220> FEATURE:
<223> OTHER INFORMATION: qh.p53-F

<400> SEQUENCE: 15
ggttcctgcc ccaggatgtt g                                                21

<210> SEQ ID NO 16
<211> LENGTH: 20
<212> TYPE: DNA
<213> ORGANISM: artificial
<220> FEATURE:
<223> OTHER INFORMATION: qh.p53-R

<400> SEQUENCE: 16
ggaacatctc gaagcgctca                                                  20

<210> SEQ ID NO 17
<211> LENGTH: 22
<212> TYPE: DNA
<213> ORGANISM: artificial
<220> FEATURE:
<223> OTHER INFORMATION: qh.Sod1-F

<400> SEQUENCE: 17
ctcactctca ggagaccatt gc                                               22

<210> SEQ ID NO 18

```
<211> LENGTH: 22
<212> TYPE: DNA
<213> ORGANISM: artificial
<220> FEATURE:
<223> OTHER INFORMATION: qh.Sod1-R

<400> SEQUENCE: 18
ccacaagcca aacgacttcc ag                                              22

<210> SEQ ID NO 19
<211> LENGTH: 22
<212> TYPE: DNA
<213> ORGANISM: artificial
<220> FEATURE:
<223> OTHER INFORMATION: qh.Sod2-F

<400> SEQUENCE: 19
ctggacaaac ctcagcccta ac                                              22

<210> SEQ ID NO 20
<211> LENGTH: 22
<212> TYPE: DNA
<213> ORGANISM: artificial
<220> FEATURE:
<223> OTHER INFORMATION: qh.Sod2-R

<400> SEQUENCE: 20
aacctgagcc ttggacacca ac                                              22

<210> SEQ ID NO 21
<211> LENGTH: 25
<212> TYPE: DNA
<213> ORGANISM: artificial
<220> FEATURE:
<223> OTHER INFORMATION: qh.Vegfa-F

<400> SEQUENCE: 21
agatcgagta catcttcaag ccatc                                           25

<210> SEQ ID NO 22
<211> LENGTH: 17
<212> TYPE: DNA
<213> ORGANISM: artificial
<220> FEATURE:
<223> OTHER INFORMATION: qh.Vegfa-R

<400> SEQUENCE: 22
cgtcattgca gcagccc                                                    17

<210> SEQ ID NO 23
<211> LENGTH: 23
<212> TYPE: DNA
<213> ORGANISM: artificial
<220> FEATURE:
<223> OTHER INFORMATION: qm.Gapdh-F

<400> SEQUENCE: 23
gggtgtgaac cacgagaaat atg                                             23

<210> SEQ ID NO 24
<211> LENGTH: 20
<212> TYPE: DNA
<213> ORGANISM: artificial
<220> FEATURE:
<223> OTHER INFORMATION: qm.Gapdh-R

<400> SEQUENCE: 24
```

```
gcagtgatgg catggactgt                                               20

<210> SEQ ID NO 25
<211> LENGTH: 21
<212> TYPE: DNA
<213> ORGANISM: artificial
<220> FEATURE:
<223> OTHER INFORMATION: qm.Gpx1-F

<400> SEQUENCE: 25
agtccaccgt gtatgccttc t                                             21

<210> SEQ ID NO 26
<211> LENGTH: 21
<212> TYPE: DNA
<213> ORGANISM: artificial
<220> FEATURE:
<223> OTHER INFORMATION: qm.Gpx1-R

<400> SEQUENCE: 26
gagacgcgac attctcaatg a                                             21

<210> SEQ ID NO 27
<211> LENGTH: 23
<212> TYPE: DNA
<213> ORGANISM: artificial
<220> FEATURE:
<223> OTHER INFORMATION: qm.BMI1-F

<400> SEQUENCE: 27
aaatccccac ttaatgtgtg tcc                                           23

<210> SEQ ID NO 28
<211> LENGTH: 21
<212> TYPE: DNA
<213> ORGANISM: artificial
<220> FEATURE:
<223> OTHER INFORMATION: qm.BMI1-R

<400> SEQUENCE: 28
cttgctggtc tccaagtaac g                                             21

<210> SEQ ID NO 29
<211> LENGTH: 23
<212> TYPE: DNA
<213> ORGANISM: artificial
<220> FEATURE:
<223> OTHER INFORMATION: qm.p16-F

<400> SEQUENCE: 29
tgttgaggct agagaggatc ttg                                           23

<210> SEQ ID NO 30
<211> LENGTH: 22
<212> TYPE: DNA
<213> ORGANISM: artificial
<220> FEATURE:
<223> OTHER INFORMATION: qm.p16-R

<400> SEQUENCE: 30
cgaatctgca ccgtagttga gc                                            22

<210> SEQ ID NO 31
<211> LENGTH: 22
<212> TYPE: DNA
```

```
<213> ORGANISM: artificial
<220> FEATURE:
<223> OTHER INFORMATION: qm.p21-F

<400> SEQUENCE: 31
tcgctgtctt gcactctggt gt                                              22

<210> SEQ ID NO 32
<211> LENGTH: 23
<212> TYPE: DNA
<213> ORGANISM: artificial
<220> FEATURE:
<223> OTHER INFORMATION: qm.p21-R

<400> SEQUENCE: 32
ccaatctgcg cttggagtga tag                                             23

<210> SEQ ID NO 33
<211> LENGTH: 22
<212> TYPE: DNA
<213> ORGANISM: artificial
<220> FEATURE:
<223> OTHER INFORMATION: qm.p53-F

<400> SEQUENCE: 33
ctggttagtc ctgagacaga gg                                              22

<210> SEQ ID NO 34
<211> LENGTH: 22
<212> TYPE: DNA
<213> ORGANISM: artificial
<220> FEATURE:
<223> OTHER INFORMATION: qm.p53-R

<400> SEQUENCE: 34
agatgcagcc aaacacaggc ac                                              22

<210> SEQ ID NO 35
<211> LENGTH: 23
<212> TYPE: DNA
<213> ORGANISM: artificial
<220> FEATURE:
<223> OTHER INFORMATION: qm.Sod1-F

<400> SEQUENCE: 35
ggtgaaccag ttgtgttgtc agg                                             23

<210> SEQ ID NO 36
<211> LENGTH: 22
<212> TYPE: DNA
<213> ORGANISM: artificial
<220> FEATURE:
<223> OTHER INFORMATION: qm.Sod1-R

<400> SEQUENCE: 36
atgaggtcct gcactggtac ag                                              22

<210> SEQ ID NO 37
<211> LENGTH: 22
<212> TYPE: DNA
<213> ORGANISM: artificial
<220> FEATURE:
<223> OTHER INFORMATION: qm.Sod2-F

<400> SEQUENCE: 37
cagacctgcc ttacgactat gg                                              22
```

```
<210> SEQ ID NO 38
<211> LENGTH: 21
<212> TYPE: DNA
<213> ORGANISM: artificial
<220> FEATURE:
<223> OTHER INFORMATION: qm.Sod2-R

<400> SEQUENCE: 38
ctcggtggcg ttgagattgt t                                          21

<210> SEQ ID NO 39
<211> LENGTH: 19
<212> TYPE: DNA
<213> ORGANISM: artificial
<220> FEATURE:
<223> OTHER INFORMATION: qm.Vegfa-F

<400> SEQUENCE: 39
ctgccgtccg attgagacc                                             19

<210> SEQ ID NO 40
<211> LENGTH: 20
<212> TYPE: DNA
<213> ORGANISM: artificial
<220> FEATURE:
<223> OTHER INFORMATION: qm.Vegfa-R

<400> SEQUENCE: 40
cccctccttg taccactgtc                                            20

<210> SEQ ID NO 41
<211> LENGTH: 22
<212> TYPE: DNA
<213> ORGANISM: artificial
<220> FEATURE:
<223> OTHER INFORMATION: qsc.Bmi1-F

<400> SEQUENCE: 41
cgtgtattgt gcgttacctg ga                                         22

<210> SEQ ID NO 42
<211> LENGTH: 22
<212> TYPE: DNA
<213> ORGANISM: artificial
<220> FEATURE:
<223> OTHER INFORMATION: qsc.Bmi1-R

<400> SEQUENCE: 42
ttcagtagtg gtctggtttt gt                                         22
```